United States Patent
Liu et al.

(10) Patent No.: US 11,512,085 B2
(45) Date of Patent: Nov. 29, 2022

(54) HETEROARYL COMPOUND HAVING DRUG ACTIVITY

(71) Applicant: SHANGHAI DUDE MEDICAL TECHNOLOGY CO., LTD, Shanghai (CN)

(72) Inventors: Xin Liu, Shanghai (CN); Zhedong Yuan, Shanghai (CN); Rui Kong, Shanghai (CN); Shan Chen, Shanghai (CN)

(73) Assignee: SHANGHAI DUDE MEDICAL TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 16/724,363

(22) Filed: Dec. 22, 2019

(65) Prior Publication Data

US 2020/0123156 A1  Apr. 23, 2020

Related U.S. Application Data

(63) Continuation of application No. PCT/CN2018/092122, filed on Jun. 21, 2018.

(30) Foreign Application Priority Data

Jun. 22, 2017 (CN) .......................... 201710483538.6

(51) Int. Cl.
*C07D 473/34* (2006.01)
*A61P 35/00* (2006.01)

(52) U.S. Cl.
CPC ............ *C07D 473/34* (2013.01); *A61P 35/00* (2018.01)

(58) Field of Classification Search
CPC ..................................................... C07D 473/34
See application file for complete search history.

(56) References Cited

U.S. PATENT DOCUMENTS

| | | | |
|---|---|---|---|
| 7,919,487 B2 | 4/2011 | Sun et al. | |
| 9,107,924 B2 * | 8/2015 | Buggy | A61K 39/39558 |
| 9,156,847 B2 * | 10/2015 | Pye | C07D 211/56 |
| 2011/0082143 A1 | 4/2011 | Sun et al. | |
| 2014/0378446 A1 | 12/2014 | Chen et al. | |
| 2016/0008366 A1 * | 1/2016 | Sukbuntherng | A61K 9/4866 514/262.1 |

FOREIGN PATENT DOCUMENTS

| | | |
|---|---|---|
| CN | 101674834 A | 3/2010 |
| CN | 103917545 A | 7/2014 |
| CN | 107501270 A | 12/2017 |
| WO | 2014130856 A2 | 8/2014 |
| WO | 2016010926 A1 | 1/2016 |

OTHER PUBLICATIONS

McMahon et al. (2000).*
Pinedo et al. (2000).*
Vippagunta et al. (2001).*

* cited by examiner

*Primary Examiner* — Paul V Ward

(57) ABSTRACT

The present invention provides a class of novel compounds having Btk selective inhibitory activity, better metabolic stability and the like.

5 Claims, 13 Drawing Sheets

DOHH-2

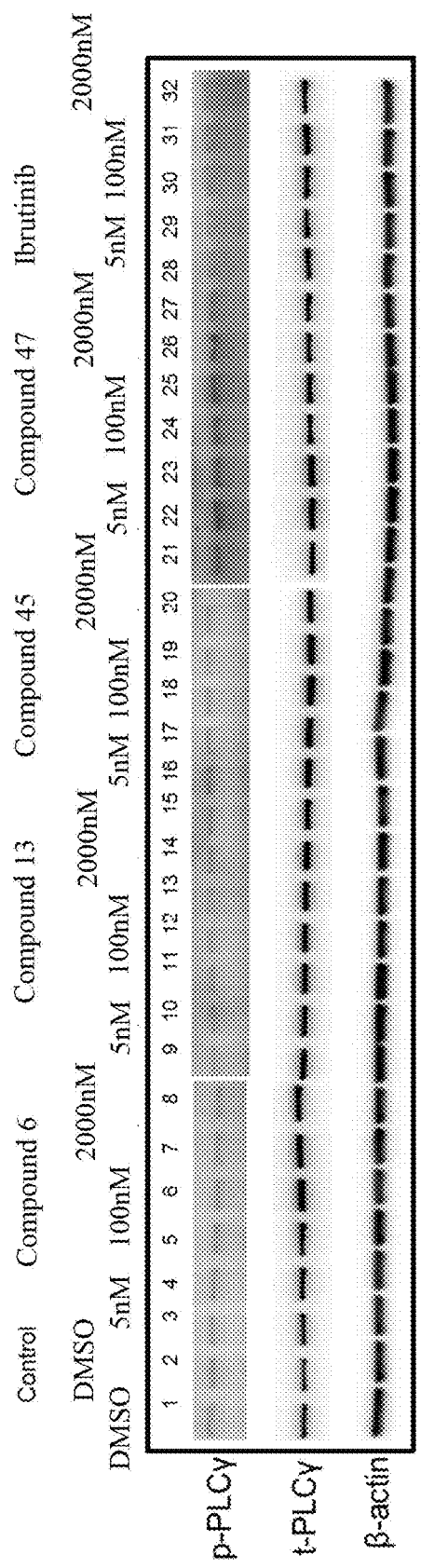
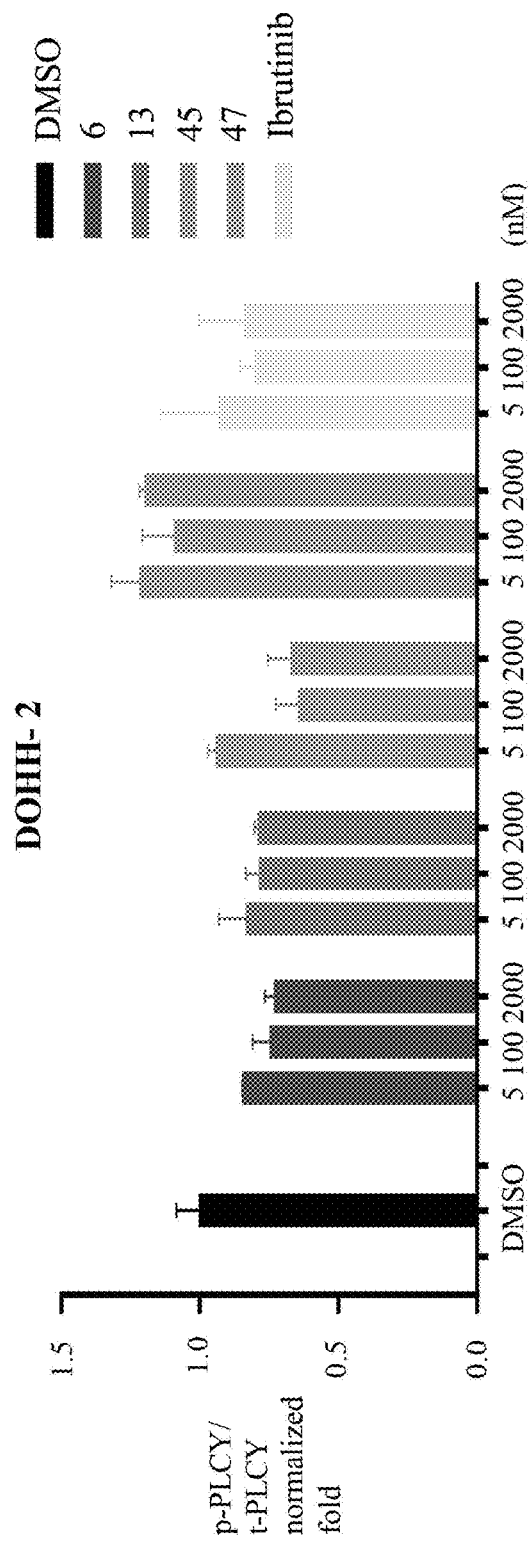
FIG. 8 (A)
FIG. 8 (B)

DOHH-2

HETEROARYL COMPOUND HAVING DRUG ACTIVITY

CROSS-REFERENCE TO RELATED APPLICATIONS

This application is a continuation of International Patent Application No. PCT/CN2018/092122 with a filing date of Jun. 21, 2018, designating the United States, now pending, and further claims priority to Chinese Patent Application No. 201710483538.6 with a filing date of Jun. 22, 2017. The content of the aforementioned applications, including any intervening amendments thereto, are incorporated herein by reference.

TECHNICAL FIELD

The present invention relates to the technical field of heteroaryl compounds having drug activity.

BACKGROUND OF THE PRESENT INVENTION

Bruton tyrosine kinase (called Btk for short hereinafter) belongs to Tec family kinase serving as non-receptor tyrosine kinase, and selectively appears in cells of B cell lines and myeloid cell series. The Btk plays an important role in signal transfer of B cells, and is a factor contributing to survival, differentiation, proliferation and activation of the B cells. Signals of the B cells passing through a B cell antigen receptor (BCR) induce biological response in a wide range, and under a condition that the signal transfer is abnormal, abnormal activation of the B cells and/or formation of pathogenic autoantibodies and the like may be caused. It is considered that the Btk serves as part of a signal transfer pathway for the B cells passing through the BCR. Therefore, as it is known, because of deletion of human Btk genes, abnormal differentiation of the B cells may be induced, so that production of immune globulins is obviously decreased, thereby causing incidence of X-linked agammaglobulinemia (XLA) (referring to non-patent literature 1). As symptoms of the disease, the significant decrease of B cells in peripheral blood and/or the susceptible increase of bacterial infection and the like may be listed. In addition, it is also known that the Btk involves activation of mast cells and/or physiological functions of blood platelet. Therefore, compounds having Btk inhibitory activity are useful for treatment of diseases related to the B cells and/or the mast cells, such as allergic diseases, autoimmune diseases, inflammatory diseases, thromboembolic diseases and cancers (referring to non-patent literature 2).

However, as the prior art of the compounds in the present invention, the following compounds are known.

As the compounds having Btk inhibitory activity, a general formula (A) is known:

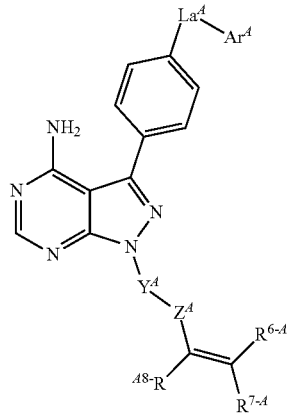

(In the formula, LaA represents CH2, O, NH or S; ArA represents substituted or unsubstituted aryl, or substituted or unsubstituted heteroaryl; YA represents any substituent group selected from alkyl, heteroalkyl, cycloalkyl, heterocycloalkyl, aryl and heteroaryl; ZA represents CO, OCO, NHCO and CS; R7-A and R8-A independently represent H, unsubstituted C1-C4 alkyl, substituted C1-C4 alkyl, unsubstituted C1-C4 heteroalkyl, substituted C1-C4 heteroalkyl, unsubstituted C3-C6 cycloalkyl, substituted C3-C6 cycloalkyl, unsubstituted C2-C6 hetero-cycloalkyl and substituted C2-C6 hetero-cycloalkyl, or the R7-A and R8-A form bonds together; R6-A represents H, substituted or unsubstituted C1-C4 alkyl, substituted or unsubstituted C1-C4 heteroalkyl, C1-C6 alkoxy alkyl, C1-C8 alkyl aminoalkyl, substituted or unsubstituted C3-C6 cycloalkyl and substituted or unsubstituted aryl (wherein definitions of various groups are selected).) The represented compounds are as follows (referring to patent literatures 1, 2 and 3).

In addition, a general formula (B) is known:

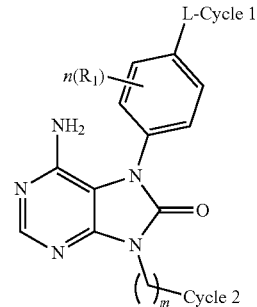

(In the formula, L represents —O—, —S—, —SO—, —SO2-, —NH—, —C(O), —CH2O, —O—CH2-, —CH2- or —CH(OH)—; R1 represents halogen atoms, C1-4 alkyl, C1-4 alkoxy, C1-4 haloalkyl or C1-4 haloalkoxy; cycle 1 represents a 4-7-membered cyclic group which can be substituted by 1-5 substituent groups independently selected from halogen atoms, C1-4 alkyl, C1-4 alkoxy, cyano, C1-4 haloalkyl or C1-4 haloalkoxy, wherein when the number of the substituent groups on the cycle 1 is 2 or more, the substituent groups may form a 4-7-membered cyclic group with atoms forming the cycle 1 bonded to the substituent groups; cycle 2 represents a 4-7-membered saturated heterocycle substituted by 1-3-K-R2; K represents —C(O)—, wherein bonds on the left side are bonded with the cycle 2; R2 represents C2-4 alkenyl or C2-4 alkynyl which can be substituted by 1-5 substituent groups independently selected from NR3R4, halogen atoms, CONR5R6, COR7 and OR8; R3 and R4 respectively independently represent hydrogen atoms or C1-4 alkyl which may be substituted by OR9 or CONR10R11; R3 and R4 may form 4-7-membered nitrogen-containing saturated heterocycles that may be substituted by oxo or hydroxyl with bonded nitrogen atoms; R5 and R6 respectively independently represent hydrogen atoms, C1-4 alkyl or phenyl; R7 represents hydrogen atom or C1-4 alkyl; R8 represents hydrogen atom, C1-4 alkyl, phenyl or benzotriazolyl; R9 represents hydrogen atom and C1-4 alkyl; R10 and R11 respectively independently represent hydrogen atom and C1-4 alkyl; n represents an integer of 0-4; m represents an integer of 0-2; and when n is more than 2, R1 may be the same or different.)

PRIOR ART LITERATURE

Patent Literature

Patent literature 1: special No. 2010-504324 bulletin
Patent literature 2: internationally disclosed No. 2008/121742 brochure
Patent literature 3: internationally disclosed No. 2010/009342 brochure Non-Patent Literature Non-patent literature 1: Nature, Vol 361, Pages 226-233, 1993
Non-patent literature 2: Anticancer Agents in Medicinal Chemistry, Vol 7, No. 6, Pages 624-632, 2007

SUMMARY OF PRESENT INVENTION

The purpose of the present invention is to provide novel compounds having Btk selective inhibitory activity and better metabolic stability.

In order to achieve the above purpose, the technical solution adopted by the present invention is as follows:

A compound Ia, Ib, Ic, Id, Ie, If or Ig of following general formulas, optical isomers or mixtures of the compounds, salts, solvates, N oxides or prodrugs thereof are as follows:

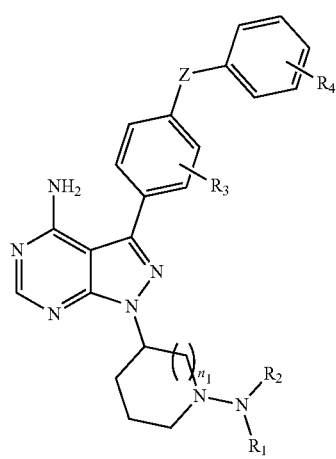

Ia

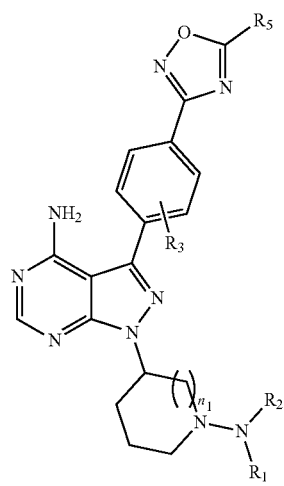

Ib

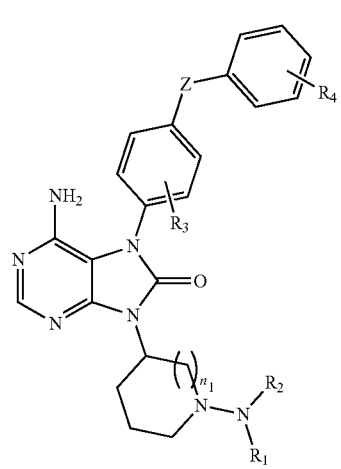

Ic

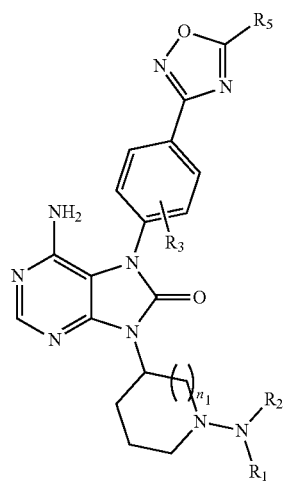

Id

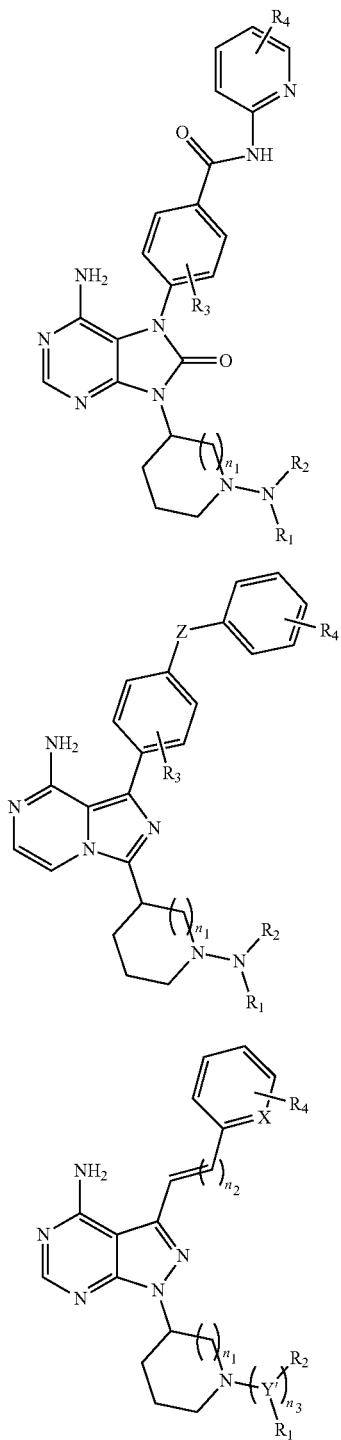

R₁ represents H, substituted or unsubstituted $C_1$-$C_4$ alkyl, and substituted or unsubstituted $C_1$-$C_4$ heteroalkyl;

R₂ represents R₆CO, R₇SO, R₈SO₂ or $C_1$-$C_6$ alkyl substituted by R₉;

R₃ represents H, one or more substituent groups, such as halogens (fluorine, chlorine, bromine and iodine), $C_1$-$C_4$ alkoxy, nitro, cyano, substituted or unsubstituted amino and substituted or unsubstituted alkyl;

R₄ represents H, one or more substituent groups, such as halogens (fluorine, chlorine, bromine and iodine), $C_1$-$C_4$ alkoxy, nitro, cyano, substituted or unsubstituted amino and substituted or unsubstituted alkyl;

R₅ represents substituted or unsubstituted $C_1$-$C_6$ alkyl, substituted or unsubstituted $C_1$-$C_6$ heteroalkyl, substituted or unsubstituted aryl, substituted or unsubstituted heteroaryl, substituted or unsubstituted $C_3$-$C_6$ cycloalkyl and substituted or unsubstituted $C_2$-$C_6$ hetero-cycloalkyl;

R₆ is alkenyl, alkynyl, as well as alkenyl and alkynyl substituted by alkyl, alkenyl, amido or halogens;

R₇ and R₈ are independently selected from $C_2$-$C_6$ alkenyl or $C_2$-$C_6$ alkynyl, and are optionally substituted by one or more groups selected from hydroxyl, $C_1$-$C_4$ alkyl, $C_3$-$C_7$ cycloalkyl, ($C_1$-$C_4$ alkyl) amino, di($C_1$-$C_4$ alkyl) amino, $C_1$-$C_3$ alkoxy, $C_3$-$C_7$ cycloalkoxy, $C_6$-$C_{10}$ aryl or $C_3$-$C_7$ hetero-cycloalkyl, or optionally selected from $C_1$-$C_5$ heteroaryl substituted by one or more groups of halogens or cyano;

R₉ is independently selected from halogen, cyano or $C_2$-$C_6$ alkenyl or $C_2$-$C_6$ alkynyl, and are optionally substituted by one or more groups selected from hydroxyl, $C_1$-$C_4$ alkyl, $C_3$-$C_7$ cycloalkyl, ($C_1$-$C_4$ alkyl) amino, di($C_1$-$C_4$ alkyl) amino, $C_1$-$C_3$ alkoxy, $C_3$-$C_7$ cycloalkoxy, $C_6$-$C_{10}$ aryl, $C_1$-$C_5$ heteroaryl or $C_3$-$C_7$ hetero-cycloalkyl;

Z is $CH_2$, O, NH or S;

$n_1$ represents 0 or 1, $n_2$ represents an integer of 1-4, and $n_3$ represents an integer of 0-1;

X represents nitrogen or carbon and may exist at any position of a benzene ring; and Y represents nitrogen.

Preferably,

R₁ represents H, $C_1$-$C_4$ alkyl and $C_1$-$C_4$ heteroalkyl;

R₂ represents R₆CO, R₇SO, R₈SO₂ or $C_1$-$C_6$ alkyl substituted by R₉; R₆ is alkenyl, alkynyl as well as alkenyl and alkynyl substituted by alkyl, alkenyl, amido or halogens; R₇ and R₈ are independently selected from $C_2$-$C_6$ alkenyl or $C_2$-$C_6$ alkynyl; and R₉ is independently selected from halogen, cyano or $C_2$-$C_6$ alkenyl or $C_2$-$C_6$ alkynyl;

R₃ represents H;

R₄ represents H, halogens (fluorine, chlorine, bromine and iodine), and substituted or unsubstituted alkyl;

R₅ represents substituted or unsubstituted $C_1$-$C_6$ alkyl, substituted or unsubstituted $C_1$-$C_6$ heteroalkyl, substituted or unsubstituted aryl and substituted or unsubstituted heteroaryl;

Z is O;

$n_1$ represents 0 or 1, $n_2$ represents an integer of 1-4, and $n_3$ represents an integer of 0-1;

X represents nitrogen or carbon and may exist at any position of a benzene ring.

In the present patent, the compound Ia, Ib, Ic, Id, Ie, If or Ig of the general formulas is also expressed as a compound represented by general formulas (Ia-Ig), or general formula compounds Ia-Ig.

A drug composition comprises the compounds Ia-Ig with the general formulas, and optical isomers or mixtures of the compounds, salts, solvates, N oxides or prodrugs thereof.

The present invention further provides applications of the compounds Ia-Ig with the general formulas, and the optical isomers or mixtures of the compounds, salts, solvates, N oxides or prodrugs thereof as Btk inhibitor drugs.

The present invention further provides applications of the compounds Ia-Ig with the general formulas, and the optical isomers or mixtures of the compounds, salts, solvates, N oxides or prodrugs thereof as drugs for preventing and/or treating Btk-related diseases, further provides applications as drugs for preventing and/or treating the Btk-related diseases, such as allergic diseases, autoimmune diseases, inflammatory diseases, thromboembolic diseases and cancers, and further provides applications as drugs for preventing and/or treating non-Hodgkin lymphoma.

A drug composition comprising the compounds Ia-Ig with the general formulas, and the optical isomers or mixtures of the compounds, salts, solvates, N oxides or prodrugs thereof serves as B cell activation inhibitors.

A method for preventing and/or treating the Btk-related diseases is to administer an effective dosage of the compounds represented by the above general formulas (Ia-Ig) [1], and the optical isomers or mixtures of the compounds, salts, solvates, N oxides or prodrugs thereof to mammals.

The present invention has beneficial effects as follows:

In addition to the Btk selective inhibitory activity, the novel compound provided by the present invention also has excellent metabolic stability and can avoid hepatotoxicity and the like. Therefore, the compound may serve as a therapeutic agent with excellent safety for treating diseases related to non-Hodgkin lymphoma cells and other B cells and/or mast cells.

In the present invention, "having Btk selective inhibitory activity" refers to having Btk selective inhibitory activity on tyrosine kinase except Btk, particularly Lck (lymphocyte specific protein tyrosine kinase) and LynA (v-yes-1 Yamaguchi sarcoma virus related oncogene homologous subtype A). By virtue of the characteristic, unexpected side effects produced by inhibiting other tyrosine kinases may be avoided. For example, as it is known, retina abnormality (oncogene) is discovered in Lck-deletion mice, (Vol 16, Pages 2351-2356, 1998), so side effects on eyes may be produced while inhibiting the Lck.

In the present invention, the halogen atoms are fluorine, chlorine, bromine and iodine.

In the present invention, C1-C4 alkyl refers to linear or branched C1-C4 alkyl such as methyl, ethyl, propyl, isopropyl, butyl, sec-butyl and tert-butyl.

In the present invention, C1-C4 alkylene refers to methylene, ethylidene, propylidene, butylidene and isomers thereof. In the present invention, C1-C4 alkoxy refers to linear or branched C1-C4 alkoxy such as methoxy, ethyoxyl, propoxy, isopropoxy, butoxy, isobutoxy and tert-butoxy.

In the present invention, C2-C4 alkenyl refers to linear or branched C2-C4 alkenyl such as vinyl, 1-propenyl, 2-propenyl, 1-butenyl, 2-butenyl, 3-butenyl and 1,3-butadienyl. C2-C4 alkynyl refers to linear or branched C2-C4 alkynyl such as acetenyl, 1-propinyl, 2-propinyl, 1-butynyl, 2-butynyl, 3-butynyl and 1,3-dibutynyl.

Isomers

The present invention further comprises all isomers unless otherwise specified. For example, the alkyl comprises linear alkyl and branched alkyl. Further, geometrical isomers (E type, Z type, cis and trans) in double bonds, rings and fused rings, optical isomers (R and S types, alpha and beta configurations, enantiomers and diastereoisomers) produced by presence of unsymmetrical carbon atoms and the like, optical activity bodies (D, L, d and l types) having optical rotation activity, polar materials (high polarity materials and low polarity materials) produced by chromatographic separation, balanced compounds, rotamers, mixtures thereof of any ratios and racemic mixtures are all included in the present invention. In addition, all isomers produced from tautomers are also included in the present invention.

In addition, the optical isomers in the present invention not only include 100% pure optical isomers but also include other optical isomers having purity less than 50%.

In the present invention, unless otherwise specified, symbols well-known to those skilled in the art are as follows:

⋅⋅⋅⋅⋅ represents bonding to one side towards paper (that is, alpha configuration);

▰ represents bonding to the front side of an observer on the paper side (that is, beta configuration);

∕ represents alpha configuration, beta configuration or mixtures thereof of any ratios.

The compounds represented by the general formulas (Ia-Ig) may be converted into corresponding salts by virtue of a known method. The salts are preferably water-soluble. Appropriate salts may be listed as follows: salts of alkali metals (potassium, sodium and the like), salts of alkali earth metals (calcium, magnesium and the like), ammonium salts, pharmaceutically acceptable salts of organic bases (tetramethyl-ammonium, triethylamine, methylamine, dimethylamine, cyclopentylamine, benzylamine, phenylethylamine, piperidine, monoethanolamine, diethanol amine, tris (hydroxymethyl) aminomethane, lysine, arginine and N-Methyl-D-glucamine), acid adduct salts (inorganic acid salts (hydrochloride, hydrobromide, hydriodate, sulfate, phosphate, nitrate and the like), organic acid salts (acetate, trifluoroacetate, lactate, tartrate, oxalate, fumarate, maleate, benzoate, citrate, mesylate, esilate, benzene sulfonate, tosylate, isethionate, glucuronate and gluconate), and the like.

The compounds represented by the general formulas (Ia-Ig) and salts thereof may also be converted into solvates. The solvates are preferably low in toxicity and water-soluble. Appropriate solvates may be listed, for example, as follows: solvates of water and alcohol solvents (such as ethanol).

In addition, the prodrugs of the compounds represented by the general formulas (Ia-Ig) refer to prodrugs that can carry out reactions in organisms by virtue of enzymes and/or gastric acid and then are converted into the compounds represented by the general formulas (Ia-Ig). As the prodrugs of the compounds represented by the general formulas (Ia-Ig), when the compounds represented by the general formulas (Ia-Ig) have hydroxyl, compounds of which the hydroxyl is acylated, alkylated, phosphorylated and boroacylated may be listed.

Applications in Drugs

Because of the Btk selective inhibitory activity, the compounds in the present invention effectively serve as agents for preventing and/or treating Btk-related diseases, that is, diseases related to the B cells and/or mast cells, such as allergic diseases, autoimmune diseases, inflammatory diseases, thromboembolic diseases, cancers and graft-versus-host diseases. In addition, the compounds in the present invention also have the effect of selectively inhibiting activation of the B cells, and thus the compounds can effectively serve as B cell activation inhibitors.

In the present invention, the allergic diseases may be listed as follows: allergy, allergic reaction, allergic conjunctivitis, allergic rhinitis and atopic dermatitis.

In the present invention, the autoimmune diseases may be listed as follows: inflammatory bowel disease, arthritis, lupus, rheumatism, psoriatic arthropathy, arthritis deformans, Still's disease, juvenile arthritis, type I diabetes, myasthenia gravis, hashimoto thyroiditis, ord's thyroiditis, Basedow's disease, Shegrin's syndrome, multiple sclerosis, guillain-barr syndrome, acute epidemic myelo-encephalitis, Addison disease, opsoclonus syndrome, ankylosing spondylitis, antiphospholipid antibody syndrome, hypoplastic anemia, autoimmune hepatitis, coeliac disease, Goodpasture's syndrome, idiopathic thrombocytopenic purpura, optic neuritis, systemic sclerosis, primary biliary cirrhosis, Reiter's disease, Takayasu's arteritis, temporal arteritis, warm antibody type autoimmune hemolytic anemia, Wegener's granulomatosis, chronic eczema, alopecia areata, Behcet's disease, chronic fatigue syndrome, autonomic instability, endometrial disease, interstitial cystitis, myotonia, vulvodynia and systemic lupus erythematosus.

In the present invention, the inflammatory diseases may be listed as follows: asthma, appendicitis, blepharitis, capillary bronchitis, bronchitis, bursitis, cervicitis, cholangitis, cholecystitis, colitis, conjunctivitis, urocystitis, dacryadenitis, dermatitis, dermatomyositis, encephalitis, endocarditis, endometritis, enteritis, epicondylitis, epididymitis, myofascitis, parametritis, gastritis, gastroenteritis, hepatitis, sudoriparous abscess, laryngitis, mastitis, meningitis, myelitis, myocarditis, myositis, nephritis, oaritis, orchitis, osteitis, pancreatitis, parotitis, pericarditis, peritonitis, pharyngitis, pleuritis, phlebitis, pneumonia, proctitis, prostatitis, nephropyelitis, rhinitis, salpingitis, nasosinusitis, stomatitis, synovitis, tendonitis, amygdalitis, uveitis, colpitis, vasculitis and vulvitis.

In the present invention, the thromboembolic diseases may be listed as follows: myocardial infarction, stenocardia, angiogenesis postoperative reocclusion, angiogenesis postoperative restenosis, main artery and coronary artery bypass surgery postoperative reocclusion, main artery and coronary artery bypass surgery postoperative restenosis, cerebral infarction, transient ischemia, peripheral vascular obstruction, pulmonary embolism and deep vein thrombosis.

In the present invention, the cancers include non-Hodgkin's lymphoma, preferably B cell non-Hodgkin's lymphoma that may be listed as follows: Burkitt lymphoma, AIDS related non-Hodgkin lymphoma, marginal zone B cell lymphomas (junction marginal zone B cell lymphomas, extranodal marginal zone B cell lymphomas), splenic marginal zone B cell lymphomas, diffuse large B cell lymphoma, primary effusion lymphoma, lymphomatoid granulomatosis, follicular lymphoma, B cell chronic lymphatic leukemia, B cell prolymphocytic leukemia, lymphocytic leukemia/Waldenstrom's macroglobulinemia, plasmacytoma, mantle cell lymphoma, mediastinal large cell type B cell lymphomas, intravascular large cell B cell lymphoma and hairy cell leukemia. Furthermore, in addition to the non-Hodgkin's lymphoma, the cancers in the present invention include membrane gland endocrine tumors that may be listed as follows: insulinoma, gastrinoma, glucagonoma, somatotropinoma, VIPoma, PPoma and GRFoma.

The compounds in the present invention may be administered separately, but in order to 1) supplement and/or enhance prevention and/or treatment effects of the compounds;

2) improve dynamic absorption of the compounds, reduce the dosage, and/or;

3) alleviate side effects of the compounds, the compounds may also be combined with other drugs to administer as a drug combination.

The drug combination of the compounds in the present invention and the other drugs may be administered in a form of matching with a compatibility agent that comprises two components in one formulation, and may also be prepared into a form of being administered in respective formulations. Conditions of drug administration in the respective formulations include conditions of simultaneous drug administration and drug administration at interval time differences. In addition, drug administration at interval time differences may include steps of administering the compounds in the present invention and administering the other drugs in sequence, and may also include steps of administering the other drugs and administering the compounds in the present invention in sequence. The respective administering methods thereof may be the same or different.

Diseases on which the above drug combination plays prevention and/or treatment effects are not specially limited, as long as the diseases can supplement and/or enhance the prevention and/or treatment effects of the compounds in the present invention.

Other drugs used for supplementing and/or enhancing the prevention and/or treatment effects of the compounds in the present invention on the allergic diseases may be listed as follows: antihistamine drugs, leukotriene antagonists, anti-allergic agents, thromboxane A2 receptor antagonists, thromboxane synthetase inhibitors and sterides.

Other drugs used for supplementing and/or enhancing the prevention and/or treatment effects of the compounds in the present invention on the autoimmune diseases may be listed as follows: immunosuppressors, sterides, disease-modified antirheumatic agents, elastase inhibitors, cannabinoid-2 receptor stimulants, prostaglandin, prostaglandin synthetase inhibitors, phosphodiesterase inhibitors, metalloprotease inhibitors, adhesion molecule inhibitors, anti-TNF-alpha preparations, anti-IL-1 preparations, anti-IL-6 preparations and other anti-cytokine protein formiulations, cytokine inhibitors, non-steroid anti-inflammatory drugs and anti-CD20 antibodies.

Other drugs used for supplementing and/or enhancing the prevention and/or treatment effects of the compounds in the present invention on the inflammatory diseases may be listed as follows: sterides, elastase inhibitors, cannabinoid-2 receptor stimulants, prostaglandin, prostaglandin synthetase inhibitors, phosphodiesterase inhibitors, metalloprotease inhibitors, adhesion molecule inhibitors, antileukotriens, anticholinergic agents, thromboxane A2 receptor antagonists, thromboxane synthetase inhibitors, xanthine derivatives, expectorants, antibacterial agents, antihistamine drugs, anti-cytokine protein preparations, cytokine inhibitors, forskolin formulations, mediator-free inhibitors and non-steroid anti-inflammatory drugs.

Other drugs used for supplementing and/or enhancing the prevention and/or treatment effects of the compounds in the present invention on the thromboembolic diseases may be listed as follows: thrombolytic drugs, heparin, heparin analogues, low molecular weight heparin, warfarin, thrombin inhibitors, factor Xa inhibitors, ADP receptor antagonists and cyclooxygenase inhibitors.

Other drugs used for supplementing and/or enhancing the prevention and/or treatment effects of the compounds in the present invention on the non-Hodgkin's lymphomas may be listed as follows: alkylating agents, metabolic antagonists, anticancer antibiotics, plant alkaloids, hormone drugs, platinum compounds, anti-CD20 antibodies and other anticancer agents.

The examples of the antihistamine drugs may be listed as follows: azelastine hydrochloride, ebastine, epinastine hydrochloride, emedastine difumarate, auranofin, oxatomide, olopatadine hydrochloride, dl-chlorpheniramine maleate, clemastine fumarate, ketotifen fumarate, cimetidine, dramamine, diphenhydramine hydrochloride, cyproheptadine hydyochloride, cetirizine hydrochloride, desloratadine, terfenadine, famotidine, fexofenadine hydrochloride, bepotastine, bepotastine besilate, mizolastine, mequitazine, mometasone furoate, ranitidine, ranitidine hydrochloride, loratadine, promethazine hydrochloride and homochlorcyclizine dihydrochloride.

The examples of the leukotriene antagonists may be listed as follows: pranlukast hydrates, montelukast, zafirlukast, ablukast, pobilukast, sulukast, iralukast, verlukast, ritolukast, innast, pirodomast, tomelukast and doqualast.

The examples of the anti-allergic agents may be listed as follows: amlexanox, azelastine hydrochloride, israpafant, ibudilast, imitrodast, ebastine, epinastine hydrochloride, emedastine difumarate, oxatomide, ozagrel hydrochloride, olopatadine hydrochloride, cromoglicic acid, sodium cromoglycate, ketotifen fumarate, seratrodast, cetirizine hydrochloride, suplatast tosilate, tazanolast, terfenadine, domitroban calcium hydrates, tranilast, nedocromil, fexofenadine, fexofenadine hydrochloride, pemirolast potassium, mequitazine, ramatroban, repirinast and loratadine.

The examples of the thromboxane A2 receptor inhibitors may be listed as follows: seratrodast, domitroban calcium hydrates and ramatroban.

The examples of the thromboxane synthetase inhibitors may be listed as follows: imitrodast sodium and ozagrel hydrochloride.

The examples of the sterides may be listed as follows: amcinonide, hydrocortisone sodium succinate, prednisolone sodium succinate, methylprednisolone sodium succinate, ciclesonide, difluprednate, betamethasone dipropionate, dexamethasone, deflazacort, triamcinolone, triamcinolone acetonide, halcinonide, dexamethasone palmitate, hydrocortisone, flumethasone pivalate, prednisolone tebutate, budesonide, prasterone sulfate, mometasone furoate, fluocinonide, fluocinolone acetonide, flurandrenolide, flunisolide, prednisolone, alomethasone propionate, clobetasol propionate, dexamethasone propionate, diproterone propionate, fluticasone propionate, beclomethasone, betamethasone, methylprednisolone, methylprednisolone suleptanate, methylprednisolone sodium succinate, sodium dexamethasone phosphate, hydrocortisone sodium phosphate, prednisolone sodium phosphate, diflucortolone valerate, dexamethasone valerate, betamethasone valerate, prednisolone valerate acetate, cortisone acetate, diflorasone diacetate, dexamethasone acetate, triamcinolone diacetate, paramethasone acetate, halopredone acetate, fludrocortisone acetate, prednisolone acetate, methylprednisolone acetate, clobetasone butyrate, hydrocortisone butyrate, hydrocortisone butyrate propionate and betamethasone butyrate propionate.

The examples of the immunosuppressors may be listed as follows: azathioprine, ascomycin, everolimus, salazosulfapyridine, cyelosporine, cyclophosphamide, sirolimus, tacrolimus, bucillamine, methotrexate and leflunomide.

The examples of the disease-modified antirheumatic agents may be listed as follows: D-penicillamine, actarit, auranofin, salazosulfapyridine, hydroxychloroquine, bucillamine, methotrexate, leflunomide, lobenzarit disodium, aurothioglucose and gold sodium thiosulfate.

The prostaglandin (called PG for short hereinafter) may be listed as follows: PGE1 formulations (such as alprostadil alpha-cyclodextrin inclusion compounds and alprostadil), PGI2 formulations (such as beraprost sodium), PG receptor stimulants, PG receptor antagonists and the like. The PG receptors may be listed as follows: PGE receptors (EP1, EP2, EP3 and EP4), PGD receptors (DP and CRTH2), PGF receptors (FP), PGI2 receptors (IP), TX receptors (TP) and the like.

The examples of the prostaglandin synthetase inhibitors may be listed as follows: salazosulfapyridine, mesalazine, olsalazine, 4-aminosalicylic acid, auranofin, carprofen, difenpiramide, flunoxaprofen, flurbiprofen, indometacin, ketoprofen, lornoxicam, loxoprofen, meloxicam, oxaprozin, parsalmide, piperson, piroxicam, piroxicam cinnamate, zaltoprofen and pranoprofen.

The examples of the phosphodiacetase inhibitors may be listed as follows: rolipram, cilomilast and roflumilast (BY-217).

The examples of the adhesion molecule inhibitors may be listed as follows: alpha4-integrin antagonists.

The examples of the TNF-alpha formulations may be listed as follows: anti-TNF-alpha antibodies, soluble TNF-alpha receptors, anti-TNF-alpha receptor antibodies, soluble TNF-alpha conjugated proteins, particularly infliximab and etanercept.

The examples of the anti-IL-1 formulations may be listed as follows: anti-IL-1 antibodies, soluble IL-1 receptors, anti-IL-1 Ra and/or IL-1 receptor antibodies, particularly anakinra.

The examples of the anti-IL-6 formulations may be listed as follows: anti-IL-6 antibodies, soluble IL-6 receptors, anti-IL-6 receptor antibodies, particularly tocilizumab.

The examples of the cytokine inhibitors may be listed as follows: suplatast tosilate and T-614.

The examples of the anticholinergic agents may be listed as follows: trihexyphenidyl, trihexyphenidyl hydrochloride, biperiden and biperiden hydrochloride.

The xanthine derivatives may be listed as follows: aminophylline, theophylline, doxofylline, cipamfylline and dihydroxypropyl theophylline.

The expectorants may be listed as follows: foeniculated spirit of ammonia, sodium bicarbonate, bromhexine hydrochloride, carbocisteine, ambroxol hydrochloride, methylcysteine hydrochloride, N-acetyl-cysteine, L-ethyl cysteine hydrochloride and tyloxapol.

The examples of the antibacterial agents may be listed as follows: cefuroxime sodium, meropenem trihydrates, netilmicin sulfate, sisomycin sulfate, ceftibuten, PA-1086, IB-367, tobramycin, PA-1420, doxorubicin, astromicin sulfate and cefetamet pivoxil hydrochloride.

The examples of the mediator-free inhibitors may be listed as follows: tranilast, sodium cromoglycate, amlexanox, repirinast, ibudilast, tazanolast, pemirolast potassium and the like.

The examples of the thrombolytic drugs may be listed as follows: alteplase, urokinase, tisokinase, nasaruplase, nateplase, t-PA, pamiteplase, monteplase, protein kinase and streptokinase.

The examples of the heparin analogues may be listed as follows: fondaparinux.

The examples of the low molecular weight heparin may be listed as follows: danaparoid sodium, enoxaparin (sodium), nadroparin calcium, bemiparin (sodium), reviparin (sodium) and tinzaparin (sodium).

The examples of the thrombin inhibitors may be listed as follows: argatroban, ximelagatran, melagatran, dabigatran, bivalirudin, lepirudin, hirudin and desirudin.

The examples of the ADP receptor antagonists may be listed as follows: ticlopidine hydrochloride and clopidogrel sulfate.

The examples of the cyclooxygenase inhibitors may be listed as follows: aspirin.

The examples of the alkylating agents may be listed as follows: chlormethine hydrochloride-N-oxides, cyclophosphamide, ifosfamide, melphalan, thiotepum, kabakun, busulfan, nimustine hydrochloride, dacarbazine, ranimustine and the like.

The examples of the metabolic antagonists may be listed as follows: methotrexate, mercaptopurine, 6-mercaptopurine, fluorouracil, tegafur, tifluorouracil, carmofur, doxifluridine, cytosine arabinoside, enocitabine, Tegafur•Gimeracil

•Oteracil potassium, gemcitabine hydrochloride, procarbazine hydrochloride, hydroxyurea and the like.

The examples of the anticancer antibiotics may be listed as follows: actinomycin D, mitomalcin C, daunorubicin hydrochloride, doxorubicin hydrochloride, aclarubicin hydrochloride, neoearcinostatin, pirarubicin hydrochloride, pharmorubicin (hydrochloride), idarubicin hydrochloride, chromomycin A3, bleomycin (hydrochloride), peplomycin sulfate, pirarubicin, zinostatin stimalamer and the like.

The examples of the plant preparations may be listed as follows: vinblastine sulfate, vincristine sulfate, vindesine sulfate, irinotecan hydrochloride, etoposide, flutamide, vinorelbine tartrate, docetaxel hydrate, paclitaxel and the like.

The examples of the hormone preparations may be listed as follows: estramustine sodium phosphate, mepitiostane, epithioandrostanol, goserelin acetate, fosfestrol (diethylstilbestrol diphosphate), tamoxifen citrate, toremifene citrate, butrozole hydrochloride hydrate, medroxyprogesterone, bicalutamide, leuprolide acetate, anastrozole, exemestane and the like.

The examples of the platinum compounds may be listed as follows: paraplatin, cis-platinum, nedaplatin and the like.

The examples of the anti-CD20 antibodies may be listed as follows: rituximab, ibritumomab and ocrelizumab.

The examples of other anticancer agents may be listed as follows: L-asparaginase, octreotide acetate, porfimer sodium and mitoxantrone acetate.

In addition, the drug combination combined with the compounds in the present invention not only includes drugs that have emerged till now, but also includes drugs that will emerge in future.

The compounds in the present invention generally are systematically or locally administered as effective components of drugs in an oral or non-oral form. The oral formulations may be listed as follows: oral liquid formulations (such as elixirs, syrup, pharmaceutically acceptable aqueous solution, suspensions and emulsion), oral solid formulations (such as tablets (including sublingual tablets and orally disintegrating tablets), pills, capsules (including hard capsules, soft capsules, gelatin capsules and microcapsules), powder, granules and dragee, and the like. The non-oral preparations may be listed as follows: liquid formulations (such as, injection (subcutaneous injection, intravenous injection, intramuscular injection, intraperitoneal injection, drips and the like), guttae ophthalmicae (such as aqueous guttae ophthalmicae (aqueous eye drops, aqueous tear eye drops, sticky eye drops, soluble eye drops and the like), non-aqueous guttae ophthalmicae (non-aqueous eye drops, non-aqueous tear eye drops and the like), and the like), topical agents (such as ointments (eye ointments)), auristilla and the like. These formulations may also be quick release preparations, sustained release preparations and other release control agents. These formulations may be prepared by known methods.

The oral liquid formulations as the oral agents may be prepared by dissolving, suspending or emulsifying active ingredients in commonly used diluents (such as purified water, ethanol or mixed liquor thereof). However, the liquid formulations may further include wetting agents, suspending agents, emulsifier, sweetening agents, flavoring agents, aromatics, preservatives, buffer agents and the like.

The oral solid formulations as the oral agents may be prepared by mixing active ingredients with excipients (such as lactose, mannitol, glucose, microcrystalline cellulose and starch), adhesives (such as hydroxy propyl cellulose, polyvinylpyrrolidone and magnesium aluminate metasilicate), disintegrating agents (such as calcium cellulose gluconate), lubricating agents (such as magnesium stearate), stabilizers, cosolvents (glutamic acid, ascorbic acid and the like) according to conventional methods. In addition, the oral solid formulations may also be coated with coating materials (such as white sugar, gelatin, hydroxy propyl cellulose and hydroxypropyl methyl cellulose phthalate) according to demands, and can be coated by more than two layers.

The external agents as the non-oral formulations may be prepared by known methods or commonly used formulas. For example, the ointments may be prepared by grinding or fusing the active ingredients in base agents. The base agents of the ointments may be well known or selected from the commonly used base agents. For example, one or more than one of a mixture of the materials selected from the following can be used: higher fatty acids or higher fatty acid esters (such as adipic acid, myristic acid, palmitic acid, stearic acid, oleic acid, adipate, myristate, palmitic acid, stearate, oleate and the like), waxes (such as beeswax, spermaceti wax and mineral wax), surfactants (such as polyoxyethylene alkyl ether phosphate), higher alcohols (such as cetyl alcohol, stearyl alcohol and cetostearyl alcohol), silicone oil (such as dimethyl polysiloxane), hydrocarbons (such as hydrophilic vaseline, vaseline white, purified lanolin and liquid paraffin), glycols (such as ethylene glycol, diethylene glycol, propylene glycol, polyethylene glycol and polyethylene glycol), vegetable oil (such as castor oil, olive oil, sesame oil and turpentine), animal oil (such as mink oil, egg oil, squalane and squalene), water, absorption promoters and anti-swelling agents. Further, the external agents may also include moisturizers, preservatives, stabilizers, antioxidants, flavor enhancers and the like.

The injections as the non-oral preparations include solid injections dissolved or suspended in solutions, suspensions, emulsion and solvents for use. For example, the injections may be injections prepared by dissolving, suspending or emulsifying the active ingredients in the solvents. The solvents may be distilled water for injection, normal saline, vegetable oil, propylene glycol, polyethylene glycol, ethanol, other alcohols and combinations thereof. Further, the injections may also include stabilizers, cosolvents (such as glutamic acid, ascorbic acid and polysorbate 80), suspending agents, emulsifiers, painless agents, buffer agents, preservatives and the like. The injections may be prepared by sterilization or sterile operation methods in the final process. In addition, sterile solid formulations may also be prepared. For example, before use, freeze dried products may be dissolved into sterilized or sterile distilled water for injection or other solvents for use.

The dosage of the compounds in the present invention used as the active ingredients of the drugs may be appropriately selected according to symptoms, ages, formulations and the like. If the compounds are the oral formulations, preferably 1-500 mg of the oral formulation is administered one to several times (such as 1-3 times) per day. If the compounds are the eye drops, eye drops having a concentration of 0.000001-5% (w/v), preferably 0.00001-0.05% (w/v), are dropped to eyes by 1 to several drops each time and one to several times per day (such as 1-8 times). In addition, if the compounds are eye ointments, eye ointments having a concentration of 0.000001-5% (w/w), preferably 0.00001-0.05% (w/w), are applied one to several times per day (such as 1-4 times).

Certainly, as mentioned above, the dosage may change according to various conditions. Therefore, both conditions exist: a dosage less than the above dosage is sufficient and the dosage must exceed the above scope.

DESCRIPTION OF THE DRAWINGS

FIG. 8(A) and FIG. 8(B) are relative expression levels of p-PLCgamma/t-PLCgamma of DOHH2 cells treated by a test sample and stimulated with anti-lgG;

DETAILED DESCRIPTION OF PREFERRED EMBODIMENTS

Figure 1:
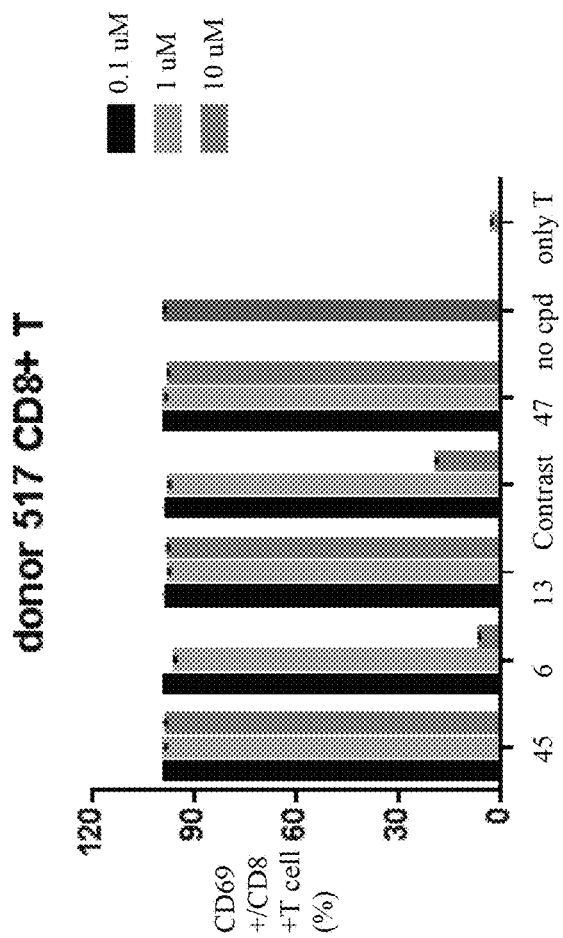
FIG. 1(A) and FIG. 1(B) are inhibitory effects of a test sample on activation of donor 517 T cells.
Figure 1:
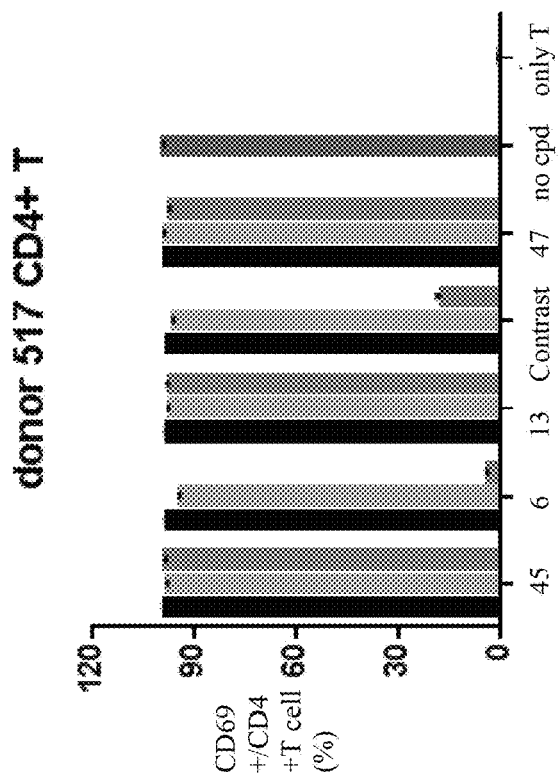

In The present invention will be described below in detail through the embodiments. However, the present invention is not limited to the embodiment.

Separation positions are obtained by chromatography, solvents in brackets represented by TLC represent used elution solvent or developing solvents, and proportions represent volume ratios.

Names of compounds used in the description generally adopt ACD/Name (registered trademark) in computer program-Advanced Chemistry Development Company named based on IUPAC rules, or named according to IUPAC nomenclature.

Embodiment 1: 3-bromo-1H-pyrazolo[3,4-D]pyrimidine-4-amine

Compounds of 4-aminopyrazolo[3,4-d]pyrimidine (50 g, 0.37 mol) and N,N-dimethylformamide (200 mL) were added into a three-mouthed flask, a solution composed of N-bromosuccinimide (78.1 g, 0.44 mol) and N,N-dimethylformamide (150 mL) was dropped at a room temperature, the temperature was raised to 65° C. after dropping completion, and stirring and reacting were performed for 4 h; the reaction solution was evaporated to dryness, water (500 mL) was added, stirring was performed at 0° C. for 1 h, an earthy yellow solid was separated out, a pH value was regulated to 7, filtration was performed, a filter cake was washed with water (250 mL) and cold ethanol (250 mL) in sequence, and vacuum drying was performed so as to obtain 65 g of the earthy yellow solid, wherein yield was 82%.

Embodiment 2: 3-bromo-1-(3-piperidyl)-1H-pyrazolo[3,4-D]pyrimidine-4-amine

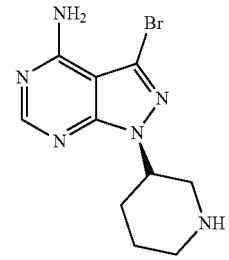

Under nitrogen protection, the compound (20 g, 0.093 mol) prepared in the embodiment 1, compounds of N—BOC-3-hydroxypiperidine (28.21 g, 0.14 mol) and triphenylphosphine (85.79 g, 0.33 mol) were added into anhydrous tetrahydrofuran (200 mL) so as to obtain light brown turbid liquid; the liquid was cooled to 0° C.; diisopropyl azodicarboxylate (66.14 g, 0.33 mol) was dropped; the temperature was maintained at 5° C. or below in the dropping process; the solution was gradually turned into light yellow liquor; the liquor was gradually heated to 0-10° C. after dropping completion and stirred and reacted for 3 h; concentrated hydrochloric acid (78 mL) was added; the liquid was heated to 50° C. and stirred and reacted for 2 h; the temperature was reduced to a room temperature; filtration was performed; the filter cake was dissolved with water; the pH value was regulated to 8 with 6N sodium hydroxide solution; dichloromethane extraction was performed; an organic phase was dried with anhydrous sodium sulfate; filtration was performed; vacuum concentration was performed until 19.5 g of an off-white solid was obtained, wherein the yield was 70%. m/z (MH$^+$) 297, 1H NMR (400 MHz, DMSO)δ1.94-2.11, 2.92-2.98, 3.01-3.36, 3.45-3.47, 5.12-5.19, 8.50-8.51, 9.61-9.87.

Embodiment 3: 3-(4-phenoxyphenyl)-1-(3-piperidyl)-1H-pyrazolo[3,4-d]pyrimidine-4-amine

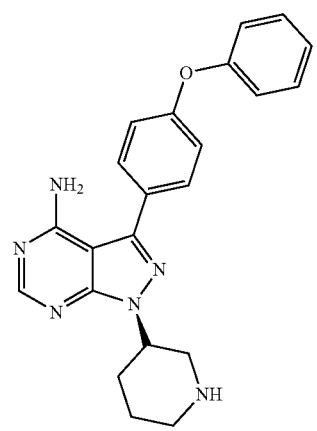

The compound (1.0 g, 1.0 eq) prepared in the embodiment 2, 4-benzyloxybenzeneboronic acid (1.7 g, 1.3 eq) and potassium carbonate (1.6 g, 4.0 eq) were suspended in dioxane (21 ml)/$H_2O$ (9 ml), and nitrogen bubbling deoxygenation was performed for 10 min; tetraphenylphosphine palladium (0.1 g, 0.05 eq) was added, and bubbling was continuously performed for 5 min; the suspension was heated to a reflux state, and TLC sampling was performed within 4 h (a ratio of dichloromethane to methanol is 9:1); the solution was cooled to a room temperature after reaction completion, liquid separation was performed, and an organic layer was concentrated to obtain an oily matter; 10 ml of water and 15 ml of ethyl acetate were added, and an insoluble substance existed; the pH value was regulated to 2-3 with 4N hydrochloric acid, and dissolved clarification was performed; liquid separation was performed, the organic layer was removed, and the water layer was washed with ethyl acetate 10 ml×2; the pH value was regulated to 8-9 with a 4N sodium hydroxide solution, 20 ml of ethyl acetate was added for performing dissolved clarification, and extraction was performed; and the liquor was washed with 10 ml of a saturated salt solution and then dried with 3 g of anhydrous sodium sulfate; and vacuum concentration was performed so as to obtain 0.5 g of a light yellow solid.

Embodiment 4: 1-3-(1-nitrosopiperidyl))-3-(4-phenoxyphenyl)-1H-pyrazolo[3,4-d]pyrimidine-4-amine

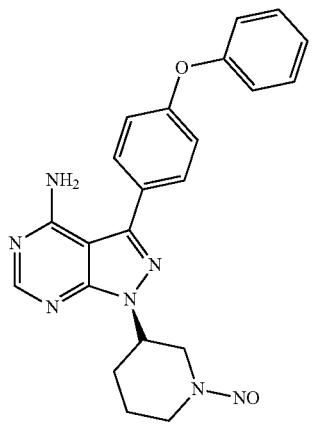

The compound (4.5 g) prepared in the embodiment 3 was suspended in 20 ml of water, acetic acid was added, and dissolved clarification was performed; 20 ml of a $NaNO_2$ solution was dropped under $N_2$ and 10° C., and a solid was separated out; the solution was stirred at 0-10° C. for 6 h, TLC sampling was performed (a ratio of ethyl acetate to methanol is 10:1), a sodium carbonate solid was added to consume excessive acetic acid after reaction completion, and 40 ml of ethyl acetate was added; liquid separation was performed, the water layer was extracted with 10 ml×2 ethyl acetate, the organic layer was merged, and the solution was washed with a saturated salt solution; and vacuum concentration was performed to dryness so as to obtain 4.5 g of a light yellow solid.

δ8.25-8.3 (d, 1H), 7.38-7.47 (m, 4H), 7.18-7.21 (m, 2H), 7.13-7.22 (m, 5H), 5.79-5.82 (s, 2H), 5.03-5.08 (m, 1H), 4.84-4.91 (m, 1H), 4.47-4.56 (m, 1H), 4.11-4.15 (m, 1H), 2.65-2.74 (m, 1H), 2.60-2.64 (m, 1H) 1.99-2.09 (m, 1H), 1.72-1.75 (m, 1H)

Embodiment 5: 1-3-(1-nitrosopiperidyl))-3-(4-phenoxyphenyl)-1H-pyrazolo[3,4-d]pyrimidine-4-amine

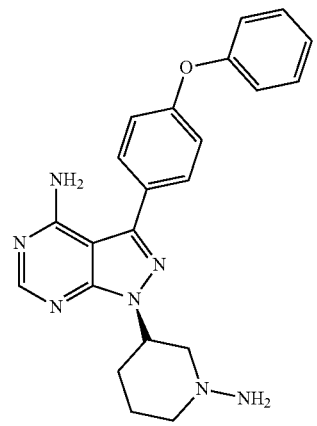

Lithium aluminum hydride (4 eq) was added into anhydrous tetrahydrofuran (20 vol) under $N_2$ and −10° C., and the temperature was maintained at −10° C. or below; the compound (2 g) prepared in the embodiment 4 was suspended in anhydrous tetrahydrofuran (10 vol), the suspension was slowly dropped into a reaction bottle, and the temperature was maintained to be less than 0° C.; the temperature was maintained for 4 h after dropping completion, and TLC sampling was performed (a ratio of ethyl acetate to methanol is 2:1); the reaction solution was quenched with $Na_2SO4.10H_2O$, diatomite filtration was performed, the filter cake was leached with 10 ml of tetrahydrofuran, vacuum concentration was performed to dryness, and the obtained white foamed solid was enabled to pass through a silica gel column so as to obtain a target product (1 g).

Embodiment 6: N-(3-(4-amino-3-(4-phenoxyphenyl)-1H-pyrazolo[3,4-D]pyrimidine-1-yl)-1-piperidyl)-acrylamide (compound DD001-1)

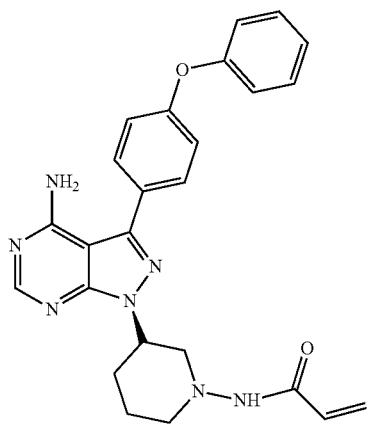

The compound (0.1 g) prepared in the embodiment 5 was dissolved into 5 ml of 2-methyltetrahydrofuran under N₂, and 7% of a NaHCO₃ solution was added; acryloyl chloride (1.1 eq) was dissolved into 2-methyltetrahydrofuran, and the liquid was slowly dropped into a reaction bottle; the reaction solution was stirred at 0° C. or below for 2 h, TLC sampling was performed (a ratio of ethyl acetate to dichloromethane to methanol is 10:5:1) for performing standing and liquid separating, the water layer was extracted with 5 ml×2 ethyl acetate, the organic layer was merged, and the solution was washed with a saturated salt solution; vacuum concentration was performed, and the eluant was enabled to pass through a silica gel column (a ratio of ethyl acetate to dichloromethane to methanol is 10:5:1) so as to obtain a white solid DD001-1 (0.1 g). δ8.51-8.54 (d, 1H), 8.41-8.42 (m, 2H), 8.11-8.32 (m, 2H), 7.85-7.89 (m, 2H), 7.78-7.82 (m, 2H), 7.18-7.21 (m, 2H), 6.52-6.63 (m, 1H), 6.13-6.21 (m, 1H), 5.69-5.77 (m, 1H), 3.81-3.87 (m, 1H), 3.60-3.3.63 (m, 1H), 3.19-3.33 (m, 2H), 1.78-2.08 (m, 2H), 1.47-1.58 (m, 2H).

Embodiment 7: 1-(3-(1-methylaminopiperidyl))-3-(4-phenoxyphenyl)-1H-pyrazolo[3,4-d]pyrimidine-4-amine

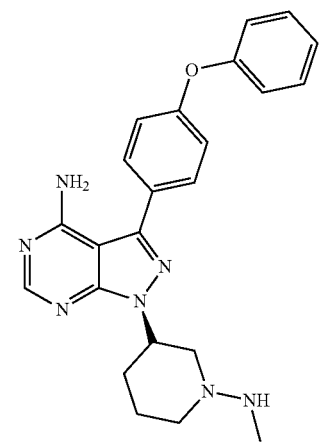

The compound (0.2 g) prepared in the embodiment 5 was suspended in methanol (5 ml); paraformaldehyde (1.0 eq) was added under N₂, a reflux reaction was carried out at 64° C. for 4 h, and TLC sampling was performed (a ratio of ethyl acetate to methanol is 2:1); the temperature was reduced to a room temperature, and a sodium cyanoborohydride/ethanol solution was added; a reflux reaction was carried out at 64° C. for 2 h after adding completion, and TLC sampling was performed (a ratio of ethyl acetate to methanol is 2:1); and vacuum concentration was performed to dryness, and the obtained eluant was enabled to pass through a silica gel column (a ratio of ethyl acetate to dichloromethane to methanol is 10:5:1) so as to obtain a white foamed solid (0.1 g).

Embodiment 8: N-(3-(4-amino-3-(4-phenoxyphenyl)-1H-pyrazolo[3,4-D]pyrimidine-1-yl)-1-piperidyl)-N-methacrylamide (DD001-2)

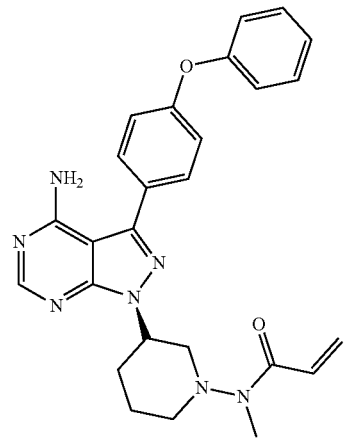

The compound prepared in the embodiment 7 was subjected to operations in the embodiment 6 so as to obtain the compound DD001-2. δ8.47-8.55 (d, 1H), 8.39-8.40 (m, 2H), 8.09-8.27 (m, 2H), 7.81-7.85 (m, 2H), 7.75-7.81 (m, 2H), 7.16-7.19 (m, 1H), 6.49-6.61 (m, 1H), 6.09-6.15 (m, 1H), 5.66-5.73 (m, 1H), 3.79-3.85 (m, 1H), 3.58-3.61 (m, 1H), 3.11-3.26 (m, 2H), 2.57-2.65 (s, 3H), 1.76-2.06 (m, 2H), 1.43-1.55 (m, 2H).

Embodiment 9: N-(3-(4-amino-3-(4-phenoxyphenyl)-1H-pyrazolo[3,4-D]pyrimidine-1-yl)-1-piperidyl)-N-ethylacrylamide (DD001-3)

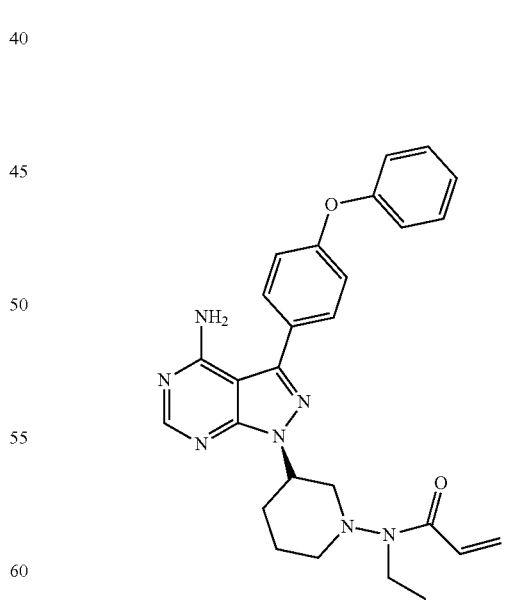

Exact Mass: 483.24

Paraformaldehyde was replaced with acetaldehyde, and operations from the embodiment 7 to the embodiment 8 were performed so as to obtain the compound DD001-3.

Embodiment 10: N-(3-(4-amino-3-(4-phenoxyphenyl)-1H-pyrazolo[3,4-D]pyrimidine-1-yl)-1-piperidyl)-N-isopropylacrylamide (DD001-4)

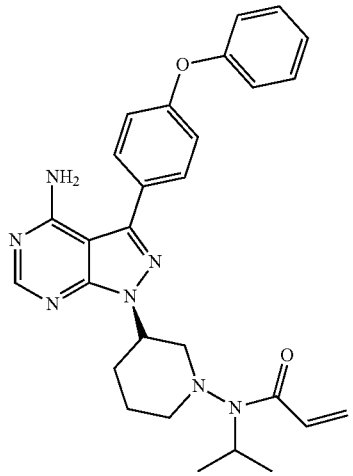

Paraformaldehyde was replaced with acetone, and operations from the embodiment 7 to the embodiment 8 were performed so as to obtain the compound DD001-4.

Embodiment 11: 3-styryl-1-(3-piperidyl)-1H-pyrazolo[3,4-D]pyrimidine-4-amine

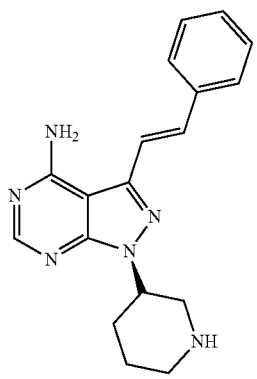

The compound (0.2 g) prepared in the embodiment 2 was dissolved into N,N-dimethylformamide (5 ml), and styrene (1.2 eq) and N,N-diisopropylethylamine (2.5 eq) were added; tris(2-methylphenyl)-phosphine (0.1 eq) and palladium acetate (0.1 eq) were added under nitrogen; the temperature was maintained at 100° C. for 10 h; and vacuum concentration was performed after reaction completion, and the product was enabled to pass through a silica gel column so as to obtain 0.1 g of a light yellow solid.

Embodiment 12: 1-(3-(4-amino-3-styryl)-1H-pyrazolo[3,4-D]pyrimidine-1-yl)-piperidyl)-2-propylene-1-one (DD001-5)

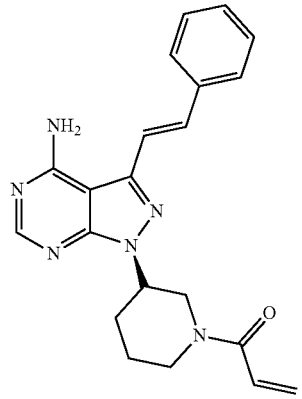

The compound prepared in the embodiment 11 was subjected to operations in the embodiment 6 so as to obtain the compound DD001-5.

Embodiment 13: 1-(3-(4-amino-3-(2-2-pyridyl)vinyl-1H-pyrazolo[3,4-D]pyrimidine-1-yl)-piperidyl)-2-propylene-1-one (DD001-6)

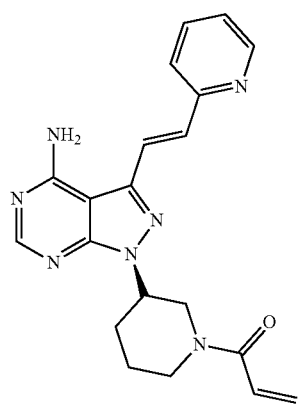

Styrene was replaced with 2-vinylpyridine and subjected to operations from the embodiment 11 to the embodiment 12 so as to obtain the compound DD001-6.

$\delta$8.57-8.61 (d, 1H), 8.19-8.21 (s, 1H), 7.98-8.01 (d, 1H), 7.83-7.79 (d, 1H), 7.55-7.60 (brs, 2H), 7.53-7.57 (m, 1H), 7.49-7.51 (m, 1H), 7.31-7.34 (m, 1H), 6.71-6.91 (m, 1H), 6.07-6.15 (m, 1H), 5.60-5.72 (m, 1H), 4.07-4.24 (m, 2H), 3.70-3.76 (m, 1H), 2.30-2.33 (m, 1H), 2.10-2.18 (m, 1H), 1.61-1.62 (m, 1H), 1.23-1.38 (m, 1H)

Embodiment 14: 1-(3-(4-amino-3-(4-chlorophenyl-vinyl)-1H-pyrazolo[3,4-D]pyrimidine-1-yl)-piperidyl)-2-propylene-1-one (DD001-7)

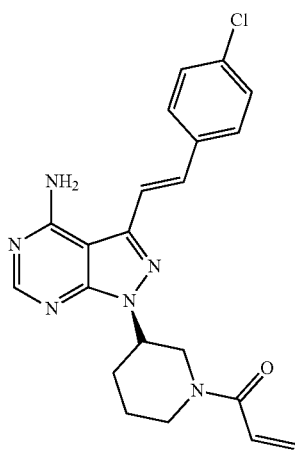

Styrene was replaced with 4-chlorostyrene and subjected to operations from the embodiment 11 to the embodiment 12 so as to obtain the compound DD001-7.

Embodiment 15: 1-(3-(4-amino-3-(3-chlorophenyl-vinyl)-1H-pyrazolo[3,4-D]pyrimidine-1-yl)-piperidyl)-2-propylene-1-one (DD001-8)

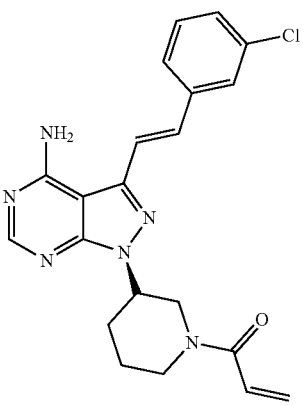

Styrene was replaced with 3-chlorostyrene and subjected to operations from the embodiment 11 to the embodiment 12 so as to obtain the compound DD001-8.

Embodiment 16: 1-(3-(4-amino-3-(2-chlorophenyl-vinyl)-1H-pyrazolo[3,4-D]pyrimidine-1-yl)-piperidyl)-2-propylene-1-one (DD001-9)

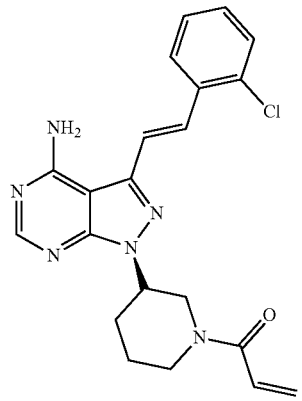

Styrene was replaced with 2-chlorostyrene and subjected to operations from the embodiment 11 to the embodiment 12 so as to obtain the compound DD001-9.

Embodiment 17: 3-bromo-1-(3-(1-tert-butoxycarbonyl)-piperidyl-1H-pyrazolo[3,4-D]pyrimidine-4-amine

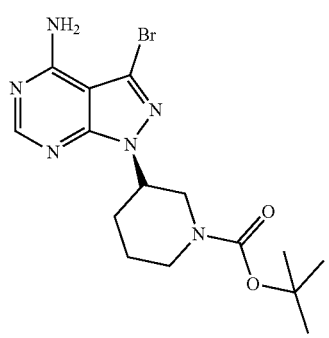

The compound (10 g) prepared in the embodiment 2 was dissolved into dichloromethane (100 ml) under nitrogen, triethylamine (2.1 eq) was added, di-tert-butyl dicarbonate ester (1.3 eq) was added at about 10° C., temperature maintaining and stirring were performed for 4-5 h, and the reaction was ended; the solution was washed with 10% of citric acid, and liquid separation was performed; and an organic layer was washed with a saturated sodium carbonate solution, and the solution was washed with a saturated salt solution, dried and subjected to vacuum concentration so as to obtain 12 g of a white solid.

Embodiment 18: 3-(4-cyanophenyl)-1-(3-(1-tert-butoxycarbonyl)-piperidyl-1H-pyrazolo[3,4-D]pyrimidine-4-amine

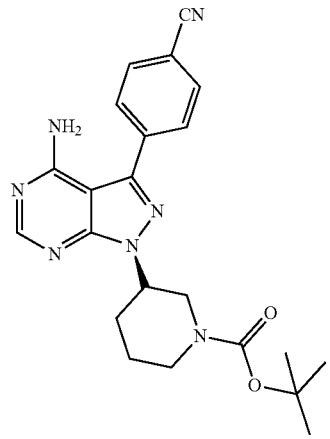

The compound (12 g) prepared in the embodiment 17, 4-cyanophenylboronic acid (1.2 eq) and potassium carbonate (2.5 eq) were dissolved into dioxane/water (120 ml/40 ml), and nitrogen bubbling deoxygenation was performed for 20 min; tetraphenylphosphine palladium (0.05 eq) was added, and nitrogen bubbling deoxygenation was continuously performed for 10 min; the solution was heated to a reflux state, the temperature was maintained for 4-5 h, and the reaction was ended; and the temperature was reduced to about 40° C. for performing liquid separation when hot, and the organic layer was subjected to vacuum concentration to dryness so as to obtain a white compound (10 g).

Embodiment 19: 3-(4-(amino(hydroxyimino)methyl)phenyl)-1-(3-(1-tert-butoxycarbonyl)-piperidyl-1H-pyrazolo[3,4-D]pyrimidine-4-amine

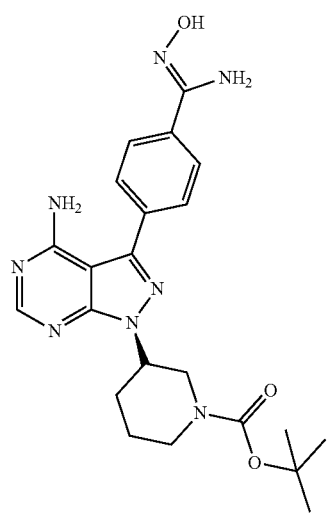

The compound (10 g, 1.0 eq) prepared in the embodiment 18 was suspended in ethanol, triethylamine (2.1 eq) and hydroxylamine hydrochloride (2.0 eq) were added in sequence, the suspension was heated to a reflux state, and TLC sampling was performed within 3 h (a ratio of ethyl acetate to methanol is 10:1); the solution was subjected to vacuum concentration to dryness after reaction completion so as to obtain a white solid, water and ethyl acetate were added, dissolved clarification and liquid separation were performed, a water layer was removed, an organic layer was washed with a saturated salt solution, and liquid separation was performed; and vacuum concentration was performed so as to obtain 10 g of the white solid.

Embodiment 20: 3-(4-(5-methyl-1,2,4-oxadiazole)phenyl)-1-(3-(1-tert-butoxycarbonyl)-piperidyl-1H-pyrazolo[3,4-D]pyrimidine-4-amine

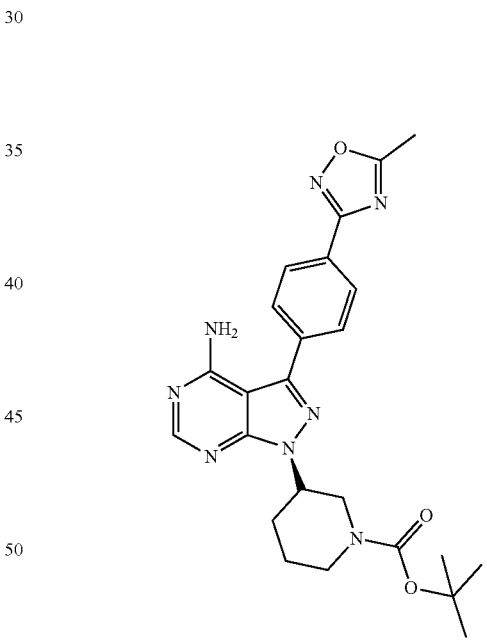

The compound (0.5 g, 1.0 eq) prepared in the embodiment 19 was suspended in toluene, triethylamine (2.0 eq) was added, acetyl chloride was dropped, a solid is separated out, and the solution stayed overnight at 100° C.; 6 vol of H₂O and 6 vol of ethyl acetate were added after reaction completion; liquid separation was performed, an organic layer was taken and washed with 10% of citric acid, and the liquid was washed with saturated sodium bicarbonate and a saturated salt solution, and vacuum concentration was performed to dryness; and the product was enabled to pass through a silica gel column so as to obtain a light white solid (0.2 g).

Embodiment 21: 3-(4-(5-methyl-1,2,4-oxadiazole)phenyl)-1-(3-piperidyl)-1H-pyrazolo[3,4-D]pyrimidine-4-amine

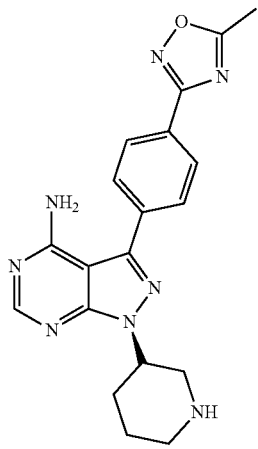

The compound (0.2 g) prepared in the embodiment 20 was dissolved into tetrahydrofuran (10 ml), concentrated hydrochloric acid (1 ml) was added, and the temperature was maintained at 50° C. for 2 h; the pH value was regulated to 7-8 with sodium carbonate after reaction completion, and the liquid was extracted with ethyl acetate (10 ml×2); and the solution was dried with anhydrous sodium sulfate and subjected to vacuum concentration to dryness so as to obtain a white solid (0.1 g).

Embodiment 22: 1-(3-(4-amino-3-(4-(5-methyl-1,2,4-oxadiazole-3-yl)phenyl)-1H-pyrazolo[3,4-D]pyrimidine-1-yl)-1-piperidyl)-2-propylene-1-one (DD001-10)

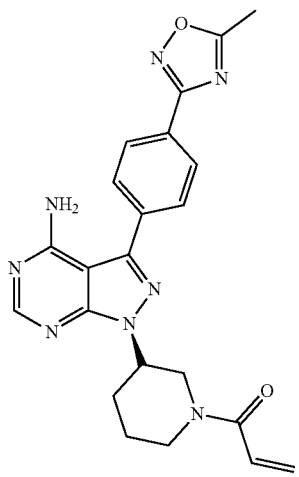

The compound prepared in the embodiment 21 was subjected to operations in the embodiment 6 so as to obtain the compound DD001-10.

Embodiment 23: 1-(3-(4-amino-3-(4-(5-vinyl-1,2,4-oxadiazole-3-yl)phenyl)-1H-pyrazolo[3,4-D]pyrimidine-1-yl)-1-piperidyl)-2-propylene-1-one (DD001-11)

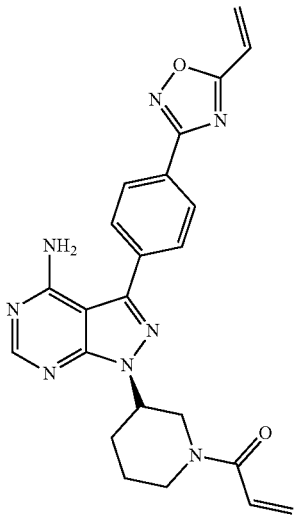

Acetyl chloride was replaced with acryloyl chloride, and the product prepared in the embodiment 19 was subjected to operations from the embodiment 20 to the embodiment 21 and the embodiment 22 so as to obtain the compound DD001-11.

Embodiment 24: 1-(3-(4-amino-3-(4-(5-(3-chloropropyl)-1,2,4-oxadiazole-3-yl)phenyl)-1H-pyrazolo[3,4-D]pyrimidine-1-yl)-1-piperidyl)-2-propylene-1-one (DD001-12)

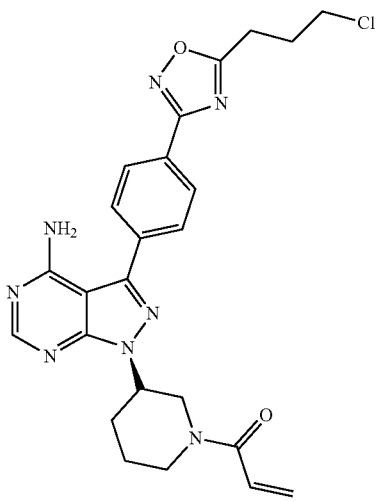

Acetyl chloride was replaced with 4-chlorobutyryl chloride, and the product prepared in the embodiment 19 was subjected to operations from the embodiment 20 to the embodiment 21 and the embodiment 22 so as to obtain the compound DD001-12.

Embodiment 25: 1-(3-(4-amino-3-(4-(5-phenyl-1,2,4-oxadiazole-3-yl)phenyl)-1H-pyrazolo[3,4-D]pyrimidine-1-yl)-1-piperidyl)-2-propylene-1-one (DD001-13)

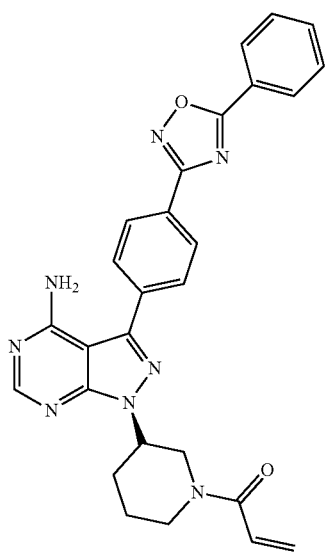

Acetyl chloride was replaced with benzoyl chloride, and the product prepared in the embodiment 19 was subjected to operations from the embodiment 20 to the embodiment 21 and the embodiment 22 so as to obtain the compound DD001-13.

Embodiment 26: 3-(6-amino-8-oxo-7,8-dihydro-9H-purine-9-yl)piperidine-1-tert-butyl formate

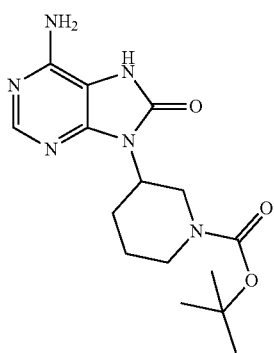 [SMILES: CC(C)(C)OC(=O)N1CCCC(n2c(=O)[nH]c3c(N)ncnc32)C1]

4,6-dichloro-5-nitropyrimidine served as an initial raw material, and 30.6 g of a target compound was prepared with reference to a synthetic method in Patent CN201180026837.

Embodiment 27: 3-(6-amino-8-oxo-7-(4-phenoxyphenyl)-7,8-dihydro-9H-purine-9-yl)piperidine-1-tert-butyl formate

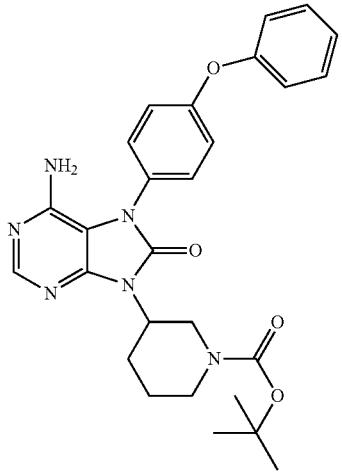 [SMILES: CC(C)(C)OC(=O)N1CCCC(n2c(=O)n(-c3ccc(Oc4ccccc4)cc3)c3c(N)ncnc32)C1]

The compound (9.0 g) prepared in the embodiment 26 was suspended in dichloromethane (200 ml), 4-phenoxyphenylboronic acid (13.3 g, 2.3 eq) was added to pass through a 4 A molecular sieve (9.0 g), pyridine (2.0 eq) was added for dissolved clarification, copper acetate (2.0 eq) was added, a reaction was carried out at 8-10° C. in an open mode, and TLC sampling was performed within 72 h (a ratio of ethyl acetate to PE is 1:2); the liquid was washed with 10% of a citric acid solution after reaction completion; liquid separation was performed, a water layer was removed, an organic layer was washed with a saturated sodium carbonate solution, the solution was washed with a saturated salt solution, and the obtained solution was directly used for the next step.

Embodiment 28: 6-amino-7-(4-phenoxyphenyl)-9-(piperidine-3-yl)-7,9-dihydro-8H-purine-8-one

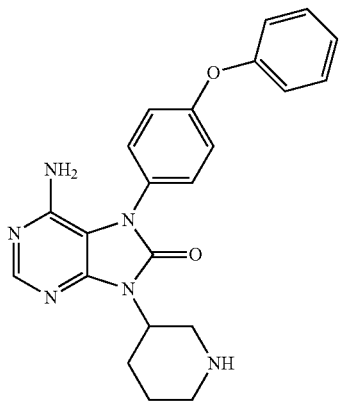 [SMILES: Nc1ncnc2c1n(-c1ccc(Oc3ccccc3)cc1)c(=O)n2C1CCCNC1]

10 ml of concentrated hydrochloric acid was dropped into the solution prepared in the embodiment 27, the solution was stirred at 25-30° C. for 4 h, and TLC sampling was performed (a ratio of ethyl acetate to methanol is 10:1); 20 ml of water was added after reaction completion, and liquid separation was performed to obtain a water layer; the pH value was regulated to 9-10 with a 4N sodium hydroxide solution, and the liquid was extracted with 50 ml of ethyl acetate; liquid separation was performed, and the water layer was extracted with 25 ml×2 ethyl acetate; and the organic layer was merged, the liquid was washed with a saturated salt solution and dried with anhydrous sodium sulfate so as to obtain 6.0 g of a solid.

Embodiment 29: N-3-(6-amino-8-oxo-7-(4-phenoxyphenyl)-7,8-dihydro-9H-purine-9-yl)piperidine-1-yl)acrylamide DD001-14

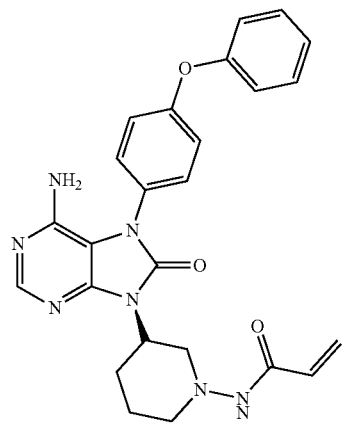

The compound (1.0 g) prepared in the embodiment 28 was subjected to operations from the embodiment 4 to the embodiment 5 and the embodiment 6 so as to obtain the compound DD001-14 (0.1 g).

Embodiment 30: N-3-(6-amino-8-oxo-7-(4-phenoxyphenyl)-7,8-dihydro-9H-purine-9-yl)piperidine-1-yl)-N-methacrylamide DD001-15

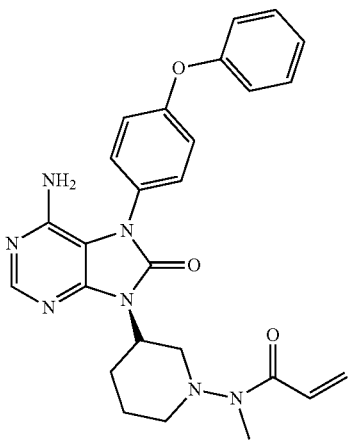

The compound (1.0 g) prepared in the embodiment 28 was subjected to operations from the embodiment 4 to the embodiment 5, the embodiment 7 and the embodiment 8 so as to obtain the compound DD001-15 (50 mg).

Embodiment 31: N-3-(6-amino-8-oxo-7-(4-phenoxyphenyl)-7,8-dihydro-9H-purine-9-yl)piperidine-1-yl)-N-ethylacrylamide DD001-16

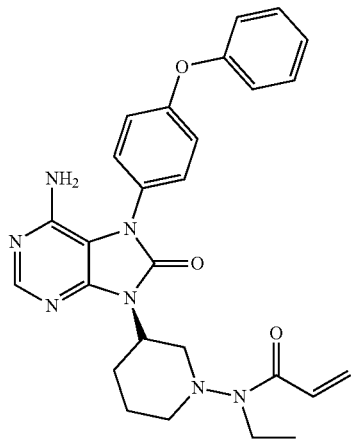

The compound (1.0 g) prepared in the embodiment 28 was subjected to operations from the embodiment 4 to the embodiment 5 and the embodiment 9 so as to obtain the compound DD001-16 (40 mg).

Embodiment 32: N-3-(6-amino-8-oxo-7-(4-phenoxyphenyl)-7,8-dihydro-9H-purine-9-yl)piperidine-1-yl)-N-isopropylacrylamide DD001-17

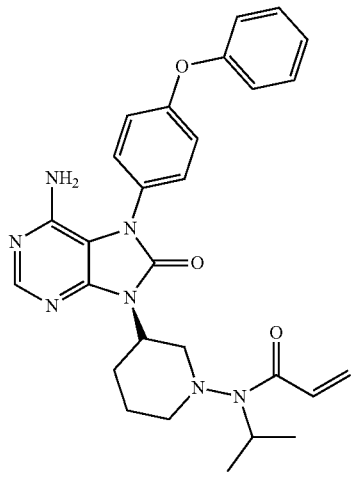

The compound (1.0 g) prepared in the embodiment 28 was subjected to operations from the embodiment 4 to the embodiment 5 and the embodiment 10 so as to obtain the compound DD001-17 (60 mg).

Embodiment 33: 3-[6-amino-7-(4-cyanophenyl)-8-oxo-7,8-dihydro-9H-purine-9-yl]piperidine-1-tert-butyl formate Embodiment 35: 9-(1-allylpropionylpiperidine-3-yl)-6-amino-7-(4-(5-vinyl-1,2,4-oxadiazole-3-yl)phenyl)-7,9-dihydro-8H-purine-8-one DD001-19

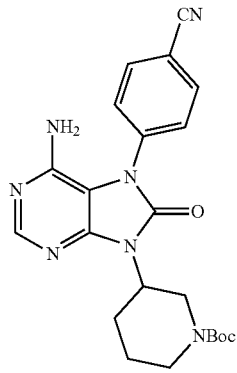 [SMILES: CC(C)(C)OC(=O)N1CCCC(n2c(=O)n(-c3ccc(C#N)cc3)c3c(N)ncnc32)C1]

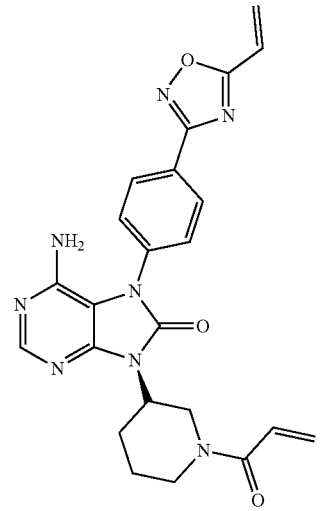

The compound (10 g) prepared in the embodiment 26 was dissolved into dioxane (150 ml), and 4-bromoxynil (1.3 eq), BINAP (1,1'-binaphthyl-2,2'-bis(diphosphino)) (0.2 eq), potassium tert-butoxide (3.0 eq) and palladium acetate (2.0 eq) were added; nitrogen deoxygenization was performed, the solution was heated to a reflux state, and the temperature was maintained for 4-6 h; the solution was subjected to vacuum concentration to dryness after reaction completion; ethyl acetate (100 ml) and water (30 ml) were added into concentrate; liquid separation was performed, and the water layer was extracted with ethyl acetate (20 ml); the organic layer was merged, and the solution was washed with a saturated salt solution and dried with anhydrous sodium sulfate; and the solution was subjected to vacuum concentration to dryness so as to obtain a light yellow solid.

The compound prepared in the embodiment 33 was subjected to operations in the embodiments 19 to 23 so as to obtain the compound DD001-19.

Embodiment 36: 9-(1-allylpropionylpiperidine-3-yl)-6-amino-7-(4-(5-(3-chloropropyl)-1,2,4-oxadiazole-3-yl)phenyl)-7,9-dihydro-8H-purine-8-one DD001-20

Embodiment 34: 9-(1-allylpropionylpiperidine-3-yl)-6-amino-7-(4-(5-methyl-1,2,4-oxadiazole-3-yl)phenyl)-7,9-dihydro-8H-purine-8-one DD001-18

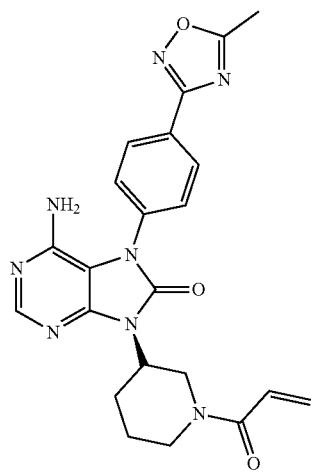

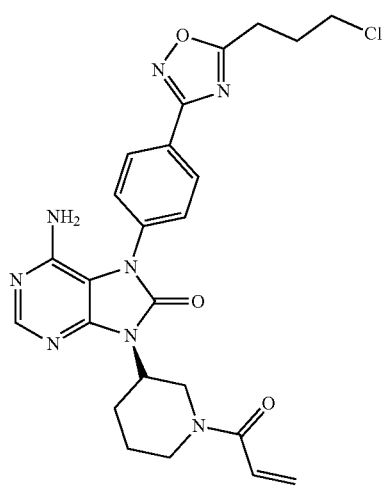

The compound prepared in the embodiment 33 was subjected to operations from the embodiment 19 to the embodiment 20, the embodiment 21 and the embodiment 22 so as to obtain the compound DD001-18.

The compound prepared in the embodiment 33 was subjected to operations in the embodiments 19 to 24 so as to obtain the compound DD001-20.

Embodiment 37: 9-(1-allylpropionylpiperidine-3-yl)-6-amino-7-(4-(5-phenyl-1,2,4-oxadiazole-3-yl)phenyl)-7,9-dihydro-8H-purine-8-one DD001-21

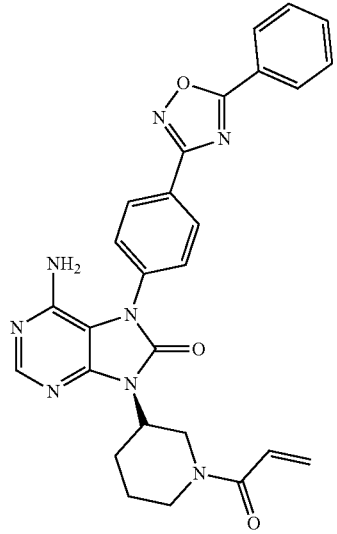

The compound prepared in the embodiment 33 was subjected to operations in the embodiments 19 to 25 so as to obtain the compound DD001-21.

Embodiment 38:
4-bromo-N-(pyridin-2-yl)benzamide

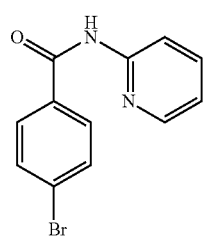 [SMILES: O=C(Nc1ccccn1)c1ccc(Br)cc1]

2-aminopyridine (0.65 g, 1.0 eq) and pyridine (0.8 g, 1.5 eq) were dissolved into dichloromethane (15 ml), 4-bromobenzoyl chloride (1.5 g) was slowly dropped, the liquid was stirred at a room temperature for 4 h after dropping completion, and the reaction was ended; the solution was washed with water and 10% of citric acid in sequence; and drying was performed under reduced pressure so as to obtain 1.5 g of a solid 4-bromo-N-(2-pyridyl)benzamide (79%).

Embodiment 39: N-(pyridin-2-yl)-4-(4,4,5,5-tetramethyl-1,3,2-dioxaborolan-2-yl)benzamide

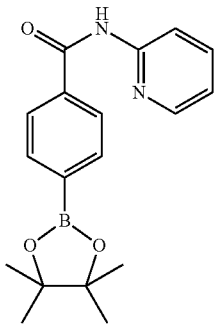 [SMILES: CC1(C)OB(c2ccc(C(=O)Nc3ccccn3)cc2)OC1(C)C]

The compound (1.0 eq) prepared in the embodiment 38 was dissolved into dioxane, and bis(pinacolato)diboron (1.3 eq) and potassium acetate (1.6 eq) were added; a reaction mixture was degassed with nitrogen, and then 1,1'-bis(diphenylphosphino)ferrocene-palladium dichloride dichloromethane (0.05 eq) was added; a reflux reaction was carried out for 8 h, most solvents were subjected to vacuum concentration after reaction completion, the liquid was dissolved with ethyl acetate, washed with water and salt and dried with anhydrous sodium sulfate, and then vacuum concentration was performed; and column chromatography was performed (a ratio of the eluent dichloromethane to methanol is 20:1) so as to obtain a white solid N-(pyridin-2-yl)-4-(4,4,5,5-tetramethyl-1,3,2-dioxaborolan-2-yl)benzamide (75.3%).

Embodiment 40: 4-(9-(1-acrylamidepiperidine-3-yl)-6-amino-8-oxo-8,9-dihydro-7H-purine-7-yl)-N-(pyridin-2-yl)benzamide DD001-22

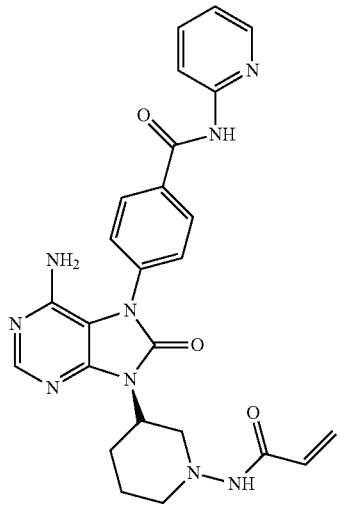

4-bromoxynil was replaced with the compound prepared in the embodiment 38, operations in the embodiment 33 were performed, and the prepared product was subjected to operations from the embodiment 28 to the embodiment 29 so as to obtain the compound DD001-22.

Embodiment 41: 4-(1-(1-acrylamidepiperidine-3-yl)-4-amino-1H-pyrazolo[3,4-d]pyrimidine-3-yl)-N-(pyridin-2-yl)benzamide DD001-23

Embodiment 43: 1-(3-(4-amino-3-(4-(fluoro-styryl)-1H-pyrazolo[3,4-d]pyrimidine-1-yl)(1-pyridyl)-2-propylene-1-one DD001-25

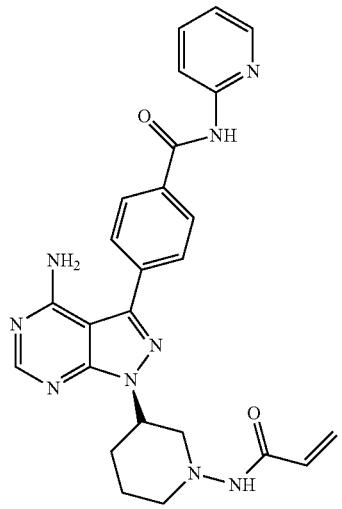

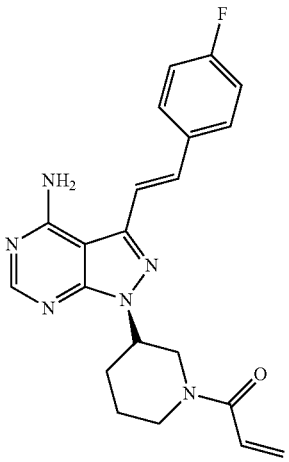

4-phenoxyphenylboronic acid was replaced with the compound prepared in the embodiment 39, and operations from the embodiment 3 to the embodiment 4, the embodiment 5 and the embodiment 6 were performed so as to obtain the compound DD001-23.

Styrene was replaced with 5-fluoro-2-vinylpyridine, and operations from the embodiment 11 to the embodiment 12 were performed so as to obtain the compound DD001-25.

Embodiment 42: N-(3-(4-amino-3-(4-(2-fluoro-phenoxy)phenyl)-1H-pyrazolo[3,4-d]pyrimidine-1-yl)(1-pyridyl)acrylamide DD001-24

Embodiment 44: N-(3-(4-amino-3-(4-(phenoxyphenyl)-1H-pyrazolo[3,4-d]pyrimidine-1-yl)(1-pyridyl)-4-(dimethylamino)-2-butyl-acrylamide DD001-26

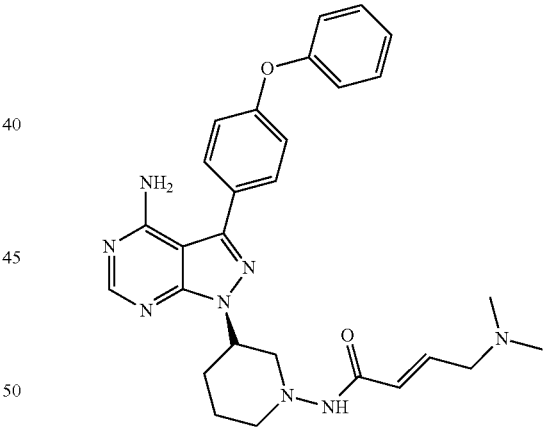

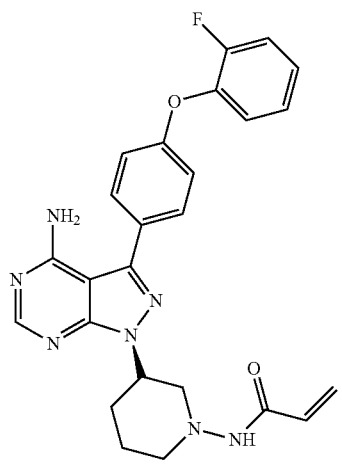

4-phenoxyphenylboronic acid was replaced with 4-(2-fluorophenoxy)phenylboronic acid, and operations from the embodiment 3 to the embodiment 4 to the embodiment 5 to the embodiment 6 were performed so as to obtain the compound DD001-24.

2-(7-azobenzotriazol)-N,N,N',N'-tetramethyluronium hexafluorophosphate (0.47 g, 1.0 eq) was added into a dichloromethane solution of the compound 1-3-(1-nitrosopiperidyl))-3-(4-phenoxyphenyl)-1H-pyrazolo[3,4-d]pyrimidine-4-amine (0.5 g, 1.0 eq) prepared in the embodiment 5, triethylamine (0.38 g, 3.0 eq) and 4-(dimethylamino)but-2-enoic acid hydrochloride (0.21 g, 1.0 eq); the solution was stirred at a room temperature for 1.5 h; the mixture was washed with water after reaction completion and then dried with magnesium sulfate, and the obtained product was subjected to vacuum concentration; and the residue was purified by a silica gel column (a ratio of eluant dichloromethane to methanol is 10:1 to 5:1) so as to obtain the target compound N-(3-(4-amino-3-(4-(phenoxyphenyl)-1H- pyrazolo[3,4-d]pyrimidine-1-yl)(1-pyridyl)-4-(dimethyl-amino)-2-butyl-acrylamide (40%) DD001-26.

Embodiment 45: N-(3-(4-amino-3-(4-(phenoxyphe-nyl)-1H-pyrazolo[3,4-d]pyrimidine-1-yl)(1-pyridyl)-4-(dimethylamino)-2-butynoic amide DD001-27

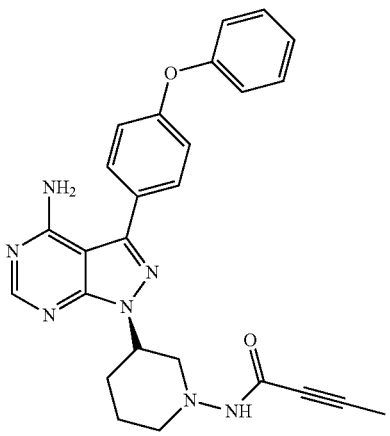

4-(dimethylamino)but-2-enoic acid was replaced with but-2-ynoic acid to perform operations in the embodiment 44 so as to obtain the target compound DD001-27. δ8.6 (d, 1H), 8.21 (d, 1H), 7.98 (d, 1H), 7.83 (d, 1H), 7.6 (brs, 2H), 7.53 (m, 1H), 7.49 (m, 1H), 7.31 (m, 1H), 6.71-6.91 (m, 1H), 6.07-6.15 (m, 1H), 5.60-5.72 (m, 1H), 4.07-4.24 (m, 2H), 3.70-3.76 (m, 1H), 2.30-2.33 (m, 1H), 2.10-2.18 (m, 1H), 1.61-1.62 (m, 1H), 1.23-1.38 (m, 1H).

Embodiment 46: 1-(3-(4-amino-3-(2-(pyridin-2-yl)vinyl)-1H-pyrazolo[3,4-d]pyrimidine-1-yl)(1-pyridyl)-4-(dimethylamino)-2-propylene-1-butanone DD001-28

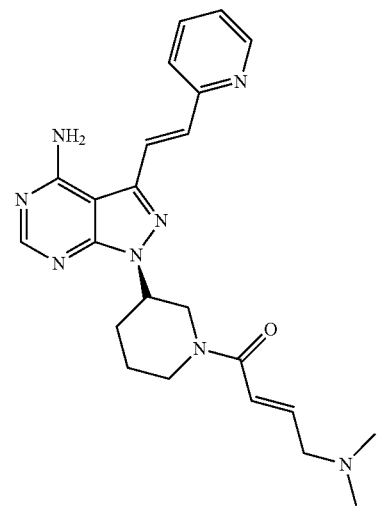

Acryloyl chloride was replaced with 4-(dimethylamino) but-2-enoic acid to perform operations similar to the embodiments 13 and 14 so as to obtain the compound 1-(3-(4-amino-3-(2-(pyridin-2-yl)vinyl)-1H-pyrazolo[3,4-d]pyrimidine-1-yl)(1-pyridyl)-4-(dimethylamino)-2-propyl-ene-1-butanone DD001-28.

Embodiment 47: 1-(3-(4-amino-3-(2-(pyridin-2-yl)vinyl)-1H-pyrazolo[3,4-d]pyrimidine-1-yl)(1-pyridyl)-2-yne-1-butanone DD001-29

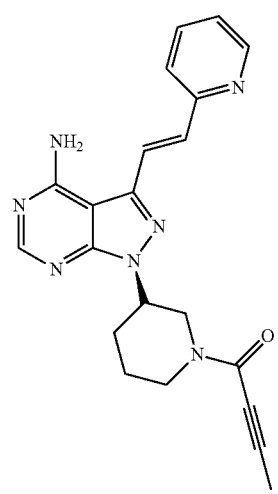

4-(dimethylamino)but-2-enoic acid was replaced with but-2-ynoic acid to perform operations in the embodiment 46 so as to obtain the target compound 1-(3-(4-amino-3-(2-(pyridin-2-yl)vinyl)-1H-pyrazolo[3,4-d]pyrimidine-1-yl)(1-pyrid yl)-2-yne-1-butanone DD001-29. δ8.51-8.55 (d, 1H), 8.21-8.27 (s, 1H), 7.83-7.79 (d, 1H), 7.68-7.72 (d, 1H), 7.55-7.60 (m, 2H), 7.53-7.57 (m, 1H), 7.49-7.51 (m, 1H), 7.31-7.34 (m, 1H), 6.71-6.91 (m, 1H), 6.07-6.15 (m, 1H), 5.60-5.72 (m, 1H), 4.07-4.24 (m, 2H), 3.70-3.76 (m, 1H), 1.92-1.95 (m, 3H), 1.61-1.62 (m, 1H).

Embodiment 48: 3-(8-amino-1-iodo-imidazo[1,5-a]pyrazine-3-yl)piperidine-1-benzyl formate

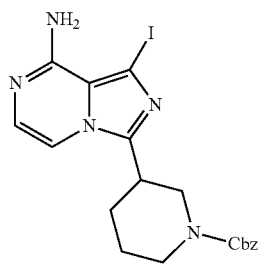 [SMILES: Nc1nccn2c(C3CCCN(C(=O)OCc4ccccc4)C3)nc(I)c12]

Z-Pro-OH was replaced with 1-[(benzyloxy)carbonyl]piperidine-3-carboxylic acid, N-bromosuccinimide was replaced with N-iodosuccinimide, and the compound 3-(8-amino-1-iodo-imidazo[1,5-a]pyrazine-3-yl)piperidine-1-benzyl formate was produced with reference to a synthetic method of an intermediate 1 in Patent CN201280045383.

Embodiment 49: 3-(8-amino-1-(4-phenoxyphenyl)-imidazo[1,5-a]pyrazine-3-yl)piperidine-1-benzyl formate

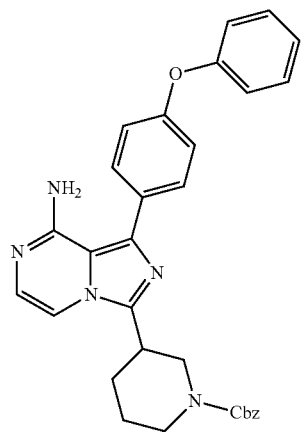 [SMILES: Nc1nccn2c(C3CCCN(C(=O)OCc4ccccc4)C3)nc(-c3ccc(Oc4ccccc4)cc3)c12]

3-(8-amino-1-iodo-imidazo[1,5-a]pyrazine-3-yl)piperidine-1-benzyl formate (5 g, 10.48 mmol), 4-phenoxyphenylboronic acid (2.69, 1.2 eq) and potassium carbonate (5.07 g, 3.5 eq) were suspended in dioxane (21 ml)/H$_2$O (9 ml), and nitrogen bubbling deoxygenation was performed for 10 min; tetraphenylphosphine palladium (0.24 g, 0.02 eq) was added, and bubbling was continuously performed for 5 min; the suspension was heated to a reflux state, and TLC sampling was performed within 4 h (a ratio of dichloromethane to methanol is 9:1); the solution was cooled to a room temperature after reaction completion, liquid separation was performed, and an organic layer was concentrated to obtain an oily matter; 10 ml of water and 15 ml of ethyl acetate were added, and an insoluble substance existed; the pH value was regulated to 2-3 with 4N hydrochloric acid, and dissolved clarification was performed; liquid separation was performed, the organic layer was removed, and the water layer was washed with ethyl acetate 10 ml×2; the pH value was regulated to 8-9 with a 4N sodium hydroxide solution, 20 ml of ethyl acetate was added for performing dissolved clarification, and extraction was performed; and the liquor was washed with 10 ml of a saturated salt solution and then dried with 3 g of anhydrous sodium sulfate; and vacuum concentration was performed so as to obtain 4.2 g of the 3-(8-amino-1-(4-phenoxyphenyl)-imidazo[1,5-a]pyrazine-3-yl)piperidine-1-benzyl formate.

Embodiment 50: 1-(4-phenoxyphenyl)-3-piperidine-3-yl-imidazo[1,5-a]pyrazine-8-amine

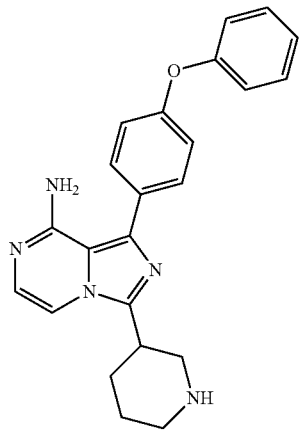 [SMILES: Nc1nccn2c(C3CCCNC3)nc(-c3ccc(Oc4ccccc4)cc3)c12]

33% of hydrobromic acid/acetic acid solution (38.5 mmol, 7 ml) was added into the 3-(8-amino-1-(4-phenoxyphenyl)-imidazo[1,5-a]pyrazine-3-yl)piperidine-1-benzyl formate (2 g, 3.85 mmol), and the solution was stirred at a room temperature for 2 h; water/dichloromethane (1:1, 30 ml) was added into the mixture; the pH value was regulated to 8-9 with a 2N sodium hydroxide solution, liquid separation was performed, and a water phase was extracted with dichloromethane (10 ml); and an organic layer was merged, and the solution was dried with anhydrous magnesium sulfate and then filtered and concentrated so as to obtain the 1-(4-phenoxyphenyl)-3-piperidine-3-yl-imidazo[1,5-a]pyrazine-8-amine.

Embodiment 51: N-(3-(8-amino-1-(4-phenoxyphenyl)imidazo[1,5-a]pyrazine-3-yl)-1-piperidyl) acrylamide

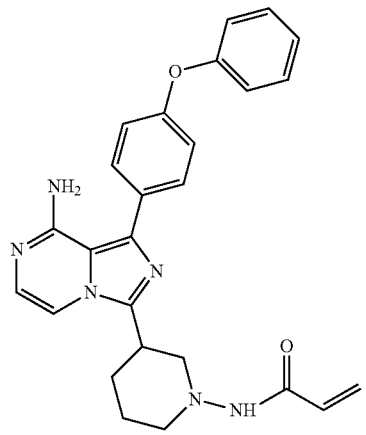

Exact Mass: 454.21

The compound 1-(4-phenoxyphenyl)-3-piperidine-3-yl-imidazo[1,5-a]pyrazine-8-amine was subjected to operations from the embodiment 4 to the embodiment 5 to the embodiment 6 so as to obtain the compound N-(3-(8-amino-1-(4-phenoxyphenyl)imidazo[1,5-a]pyrazine-3-yl)-1-piperidyl) acrylamide.

List of target compounds

| Embodiment | Classification | Structure | Name | (M + H)+ m/z |
|---|---|---|---|---|
| 6 | Ia | 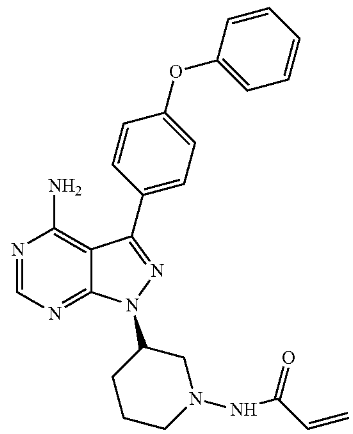 | N-(3-(4-amino-3-(4-phenoxyphenyl)-1H-pyrazolo[3,4-D]pyrimidine-1-yl)-1-piperidyl)-acrylamide | 456.2 |
| 8 | Ia | 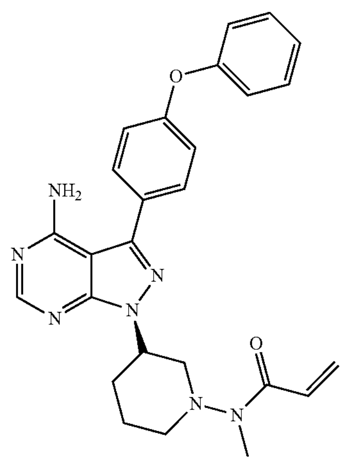 | N-(3-(4-amino-3-(4-phenoxyphenyl)-1H-pyrazolo[3,4-D]pyrimidine-1-yl)-1-piperidyl)-N-methacrylamide | 470.2 |
| 9 | Ia | 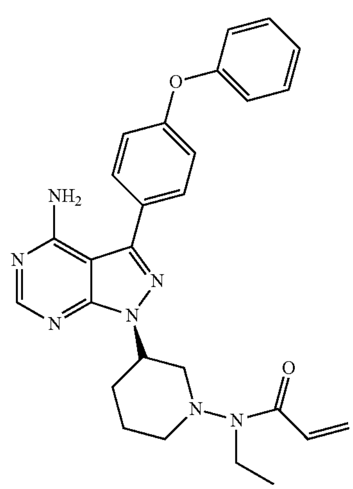 | N-(3-(4-amino-3-(4-phenoxyphenyl)-1H-pyrazolo[3,4-D]pyrimidine-1-yl)-1-piperidyl)-N-ethylacrylamide | 484.2 |

-continued

| Embodiment | Classification | Structure | Name | (M + H)+ m/z |
|---|---|---|---|---|
| 10 | Ia | 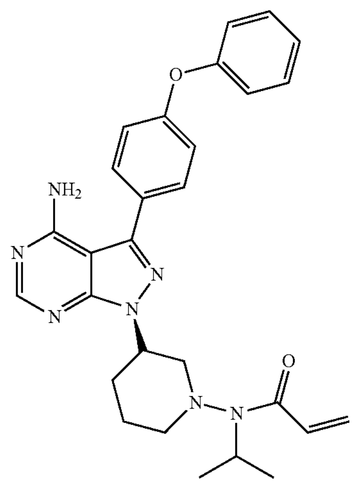 | N-(3-(4-amino-3-(4-phenoxyphenyl)-1H-pyrazolo[3,4-D]pyrimidine-1-yl)-1-piperidyl)-N-isopropylacrylamide | 498.2 |
| 12 | Ig | 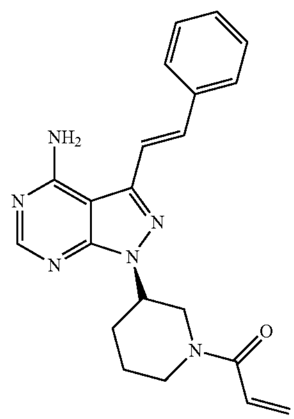 | 1-(3-(4-amino-3-styryl)-1H-pyrazolo[3,4-D]pyrimidine-1-yl)-piperidyl)-2-propylene-1-one | 375.1 |
| 13 | Ig | 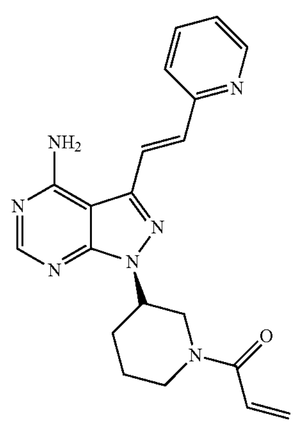 | 1-(3-(4-amino-3-(2-2-pyridyl)vinyl-1H-pyrazolo[3,4-D]pyrimidine-1-yl)-piperidyl)-2-propylene-1-one | 376.1 |

-continued

| Embodiment | Classification | Structure | Name | (M + H)+ m/z |
|---|---|---|---|---|
| 14 | Ig | 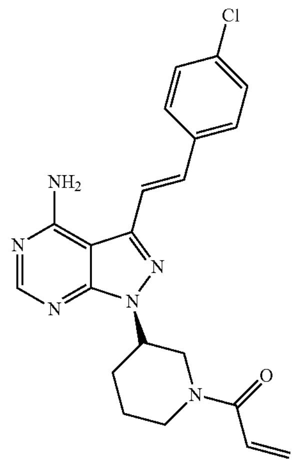 | 1-(3-(4-amino-3-(4-chlorophenylvinyl)-1H-pyrazolo[3,4-D]pyrimidine-1-yl)-piperidyl)-2-propylene-1-one | 410.1 |
| 15 | Ig | 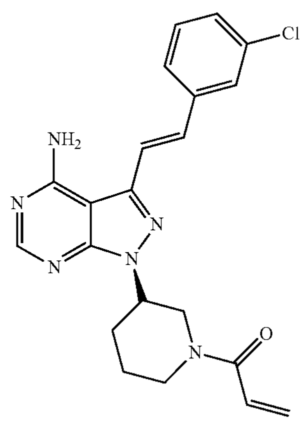 | 1-(3-(4-amino-3-(3-chlorophenylvinyl)-1H-pyrazolo[3,4-D]pyrimidine-1-yl)-piperidyl)-2-propylene-1-one | 410.1 |
| 16 | Ig | 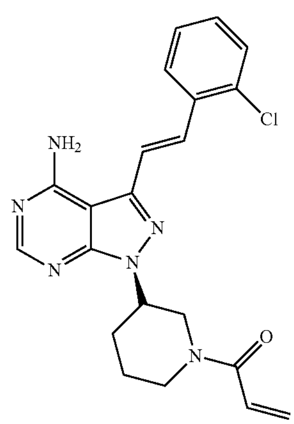 | 1-(3-(4-amino-3-(2-chlorophenylvinyl)-1H-pyrazolo[3,4-D]pyrimidine-1-yl)-piperidyl)-2-propylene-1-one | 410.1 |

-continued

| Embodiment | Classification | Structure | Name | (M + H)+ m/z |
|---|---|---|---|---|
| 22 | Ib | 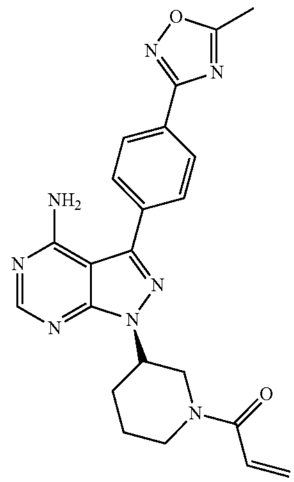 | 1-(3-(4-amino-3-(4-(5-methyl-1,2,4-oxadiazole-3-yl)phenyl)-1H-pyrazolo[3,4-D]pyrimidine-1-yl)-1-piperidyl)-2-propylene-1-one | 431.2 |
| 23 | Ib | 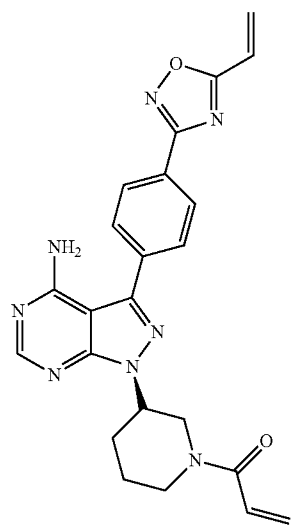 | 1-(3-(4-amino-3-(4-(5-vinyl-1,2,4-oxadiazole-3-yl)phenyl)-1H-pyrazolo[3,4-D]pyrimidine-1-yl)-1-piperidyl)-2-propylene-1-one | 443.2 |
| 24 | Ib | 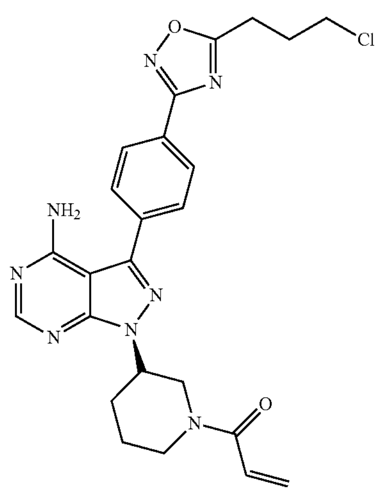 | 1-(3-(4-amino-3-(4-(5-(3-chloropropyl)-1,2,4-oxadiazole-3-yl)phenyl)-1H-pyrazolo[3,4-D]pyrimidine-1-yl)-1-piperidyl)-2-propylene-1-one | 494.2 |

-continued

| Embodiment | Classification | Structure | Name | (M + H)⁺ m/z |
|---|---|---|---|---|
| 25 | Ib | 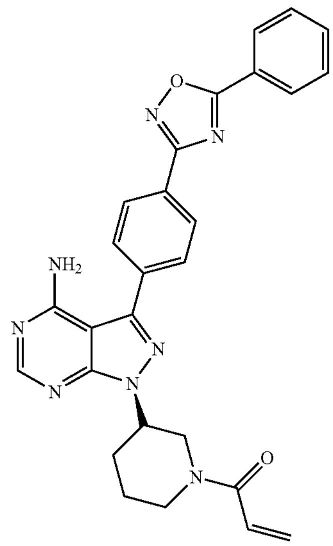 | 1-(3-(4-amino-3-(4-(5-phenyl-1,2,4-oxadiazole-3-yl)phenyl)-1H-pyrazolo[3,4-D]pyrimidine-1-yl)-1-piperidyl)-2-propylene-1-one | 493.21 |
| 29 | Ic | 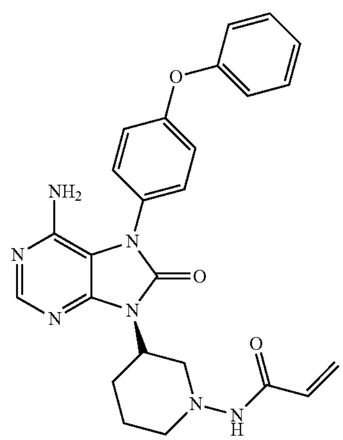 | N-3-(6-amino-8-oxo-7-(4-phenoxyphenyl)-7,8-dihydro-9H-purine-9-yl)piperidine-1-yl)acrylamide | 472.21 |
| 30 | Ic | 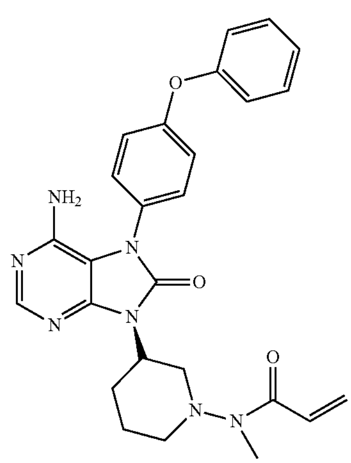 | N-3-(6-amino-8-oxo-7-(4-phenoxyphenyl)-7,8-dihydro-9H-purine-9-yl)piperidine-1-yl)-N-methacrylamide | 486.22 |

-continued

| Embodiment | Classification | Structure | Name | (M + H)+ m/z |
|---|---|---|---|---|
| 31 | Ic | 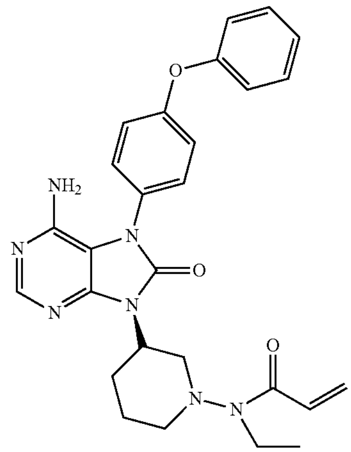 | N-3-(6-amino-8-oxo-7-(4-phenoxyphenyl)-7,8-dihydro-9H-purine-9-yl)piperidine-1-yl)-N-ethylacrylamide | 500.24 |
| 32 | Ic | 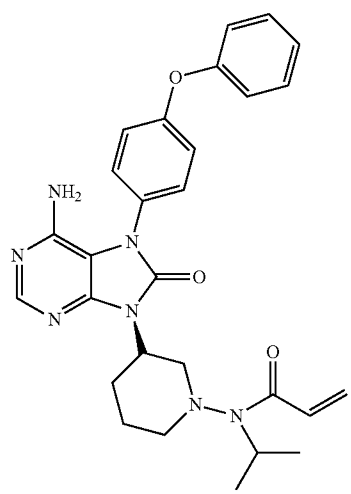 | N-3-(6-amino-8-oxo-7-(4-phenoxyphenyl)-7,8-dihydro-9H-purine-9-yl)piperidine-1-yl)-N-isopropylacrylamide | 514.25 |
| 34 | Id | 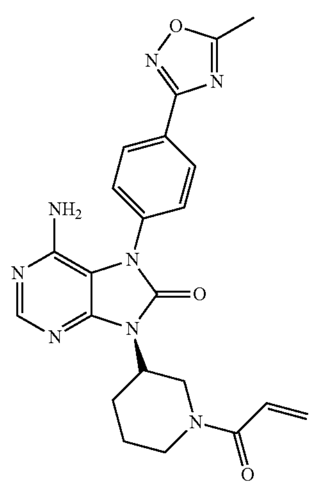 | 9-(1-allylpropionylpiperidine-3-yl)-6-amino-7-(4-(5-methyl-1,2,4-oxadiazole-3-yl)phenyl)-7,9-dihydro-8H-purine-8-one | 447.18 |

| Embodiment | Classification | Structure | Name | (M + H)+ m/z |
|---|---|---|---|---|
| 35 | Id | 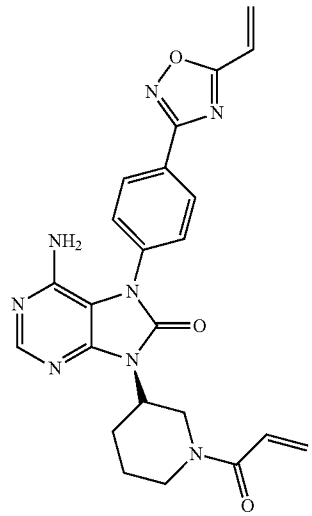 | 9-(1-allylpropionylpiperidine-3-yl)-6-amino-7-(4-(5-vinyl-1,2,4-oxadiazole-3-yl)phenyl)-7,9-dihydro-8H-purine-8-one | 459.18 |
| 36 | Id | 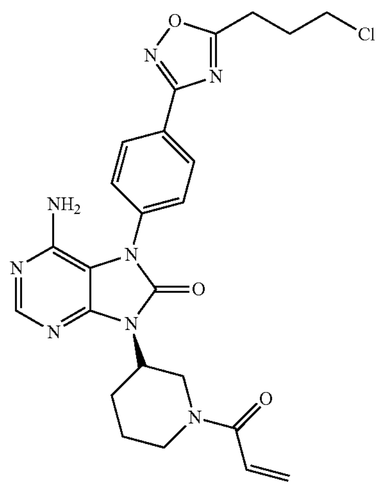 | 9-(1-allylpropionylpiperidine-3-yl)-6-amino-7-(4-(5-(3-chloropropyl)-1,2,4-oxadiazole-3-yl)phenyl)-7,9-dihydro-8H-purine-8-one | 510.17 |
| 37 | Id | 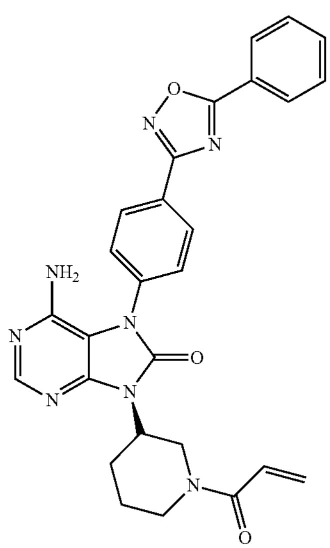 | 9-(1-allylpropionylpiperidine-3-yl)-6-amino-7-(4-(5-phenyl-1,2,4-oxadiazole-3-yl)phenyl)-7,9-dihydro-8H-purine-8-one | 509.20 |

-continued

| Embodiment | Classification | Structure | Name | (M + H)+ m/z |
|---|---|---|---|---|
| 40 | Ie | 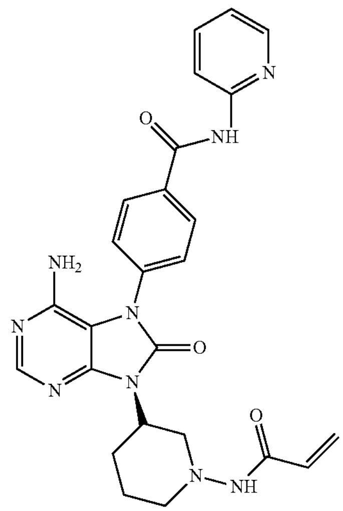 | 4-(9-(1-acrylamidepiperidine-3-yl)-6-amino-8-oxo-8,9-dihydro-7H-purine-7-yl)-N-(pyridin-2-yl)benzamide | 500.21 |
| 41 | Ie | 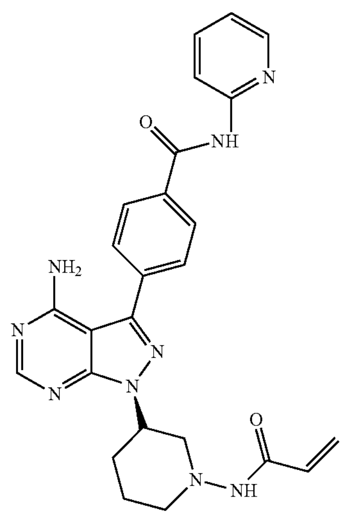 | 4-(1-(1-acrylamidepiperidine-3-yl)-4-amino-1H-pyrazolo[3,4-d]pyrimidine-3-yl)-N-(pyridin-2-yl)benzamide | 484.22 |
| 42 | Ia | 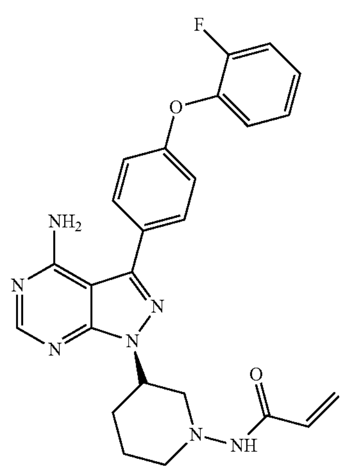 | N-(3-(4-amino-3-(4-(2-fluorophenoxy)phenyl)-1H-pyrazolo[3,4-d]pyrimidine-1-yl)(1-pyridyl)acrylamide | 474.20 |

-continued

| Embodiment | Classification | Structure | Name | (M + H)⁺ m/z |
|---|---|---|---|---|
| 43 | Ig | 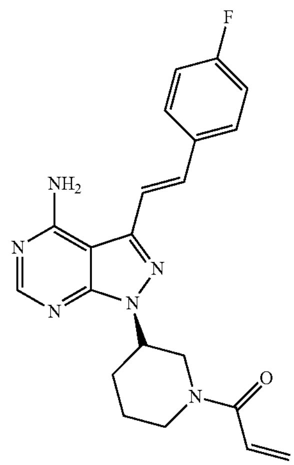 | 1-(3-(4-amino-3-(4-(fluorostyryl)-1H-pyrazolo[3,4-d]pyrimidine-1-yl)(1-pyridyl)-2-propylene-1-one | 393.18 |
| 44 | Ia | 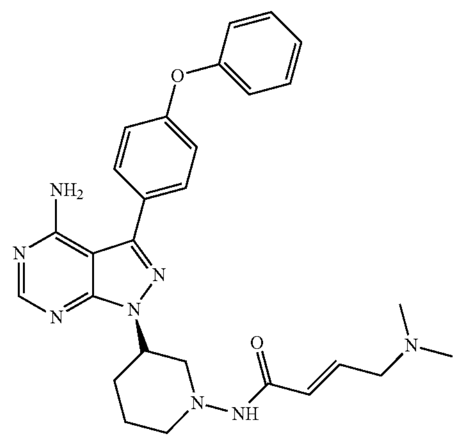 | N-(3-(4-amino-3-(4-(phenoxyphenyl)-1H-pyrazolo[3,4-d]pyrimidine-1-yl)(1-pyridyl)-4-(dimethylamino)-2-butyl-acrylamide | 513.27 |
| 45 | Ia | 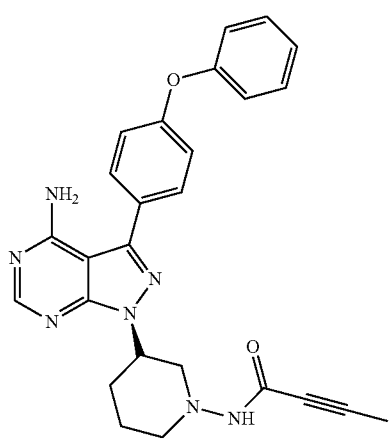 | N-(3-(4-amino-3-(4-(phenoxyphenyl)-1H-pyrazolo[3,4-d]pyrimidine-1-yl)(1-pyridyl)-4-(dimethylamino)-2-butynoicamide | 468.21 |

-continued

| Embodiment | Classification | Structure | Name | (M + H)+ m/z |
|---|---|---|---|---|
| 46 | Ig | 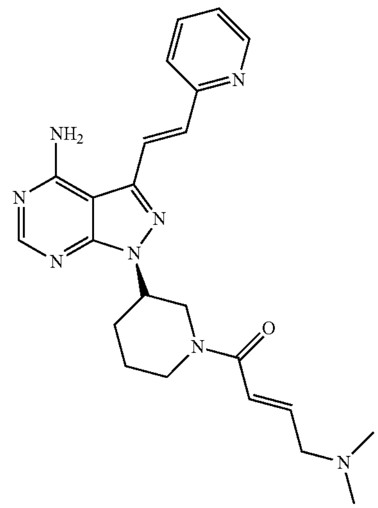 | 1-(3-(4-amino-3-(2-(pyridin-2-yl)vinyl)-1H-pyrazolo[3,4-d]pyrimidine-1-yl)(1-pyridyl)-4-(dimethylamino)-2-propylene-1-butanone | 433.24 |
| 47 | Ig | 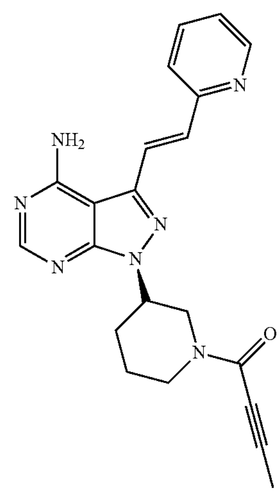 | 1-(3-(4-amino-3-(2-(pyridin-2-yl)vinyl)-1H-pyrazolo[3,4-d]pyrimidine-1-yl)(1-pyridyl)-2-yne-1-butanone | 388.18 |
| 51 | If | 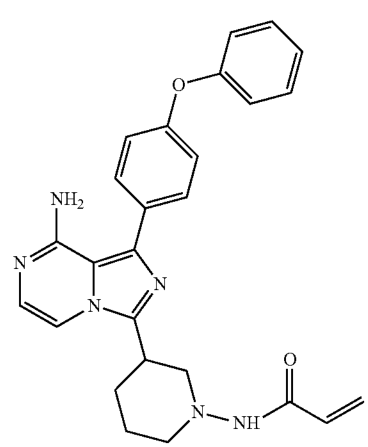 [SMILES: C=CC(=O)NN1CCCC(c2nc(-c3ccc(Oc4ccccc4)cc3)c3c(N)nccn23)C1] | N-(3-(8-amino-1-(4-phenoxyphenyl)imidazo[1,5-a]pyrazine-3-yl)-1-piperidyl)acrylamide | 454.21 |

Biological Embodiment 1: Determination of Btk Inhibitory Activity and Btk Selectivity (In Vitro Test)

Determination of Btk Enzyme Inhibitory Activity
Kinase Reaction:
Buffer solution: 50 mM Hepes pH 7.0, 0.1 mM Orthovanadate, 5 mM $MgCl_2$, 0.01% of BSA;
2 nM BTK;
1 mM TK-peptide, 20 mM ATP, 50 nM SEB;
Pre-incubation for 15 minutes;
Reaction at 23° C. for 90 minutes;
Color Development Reaction:
Developing buffer solution: 50 mM Hepes pH8.0, 0.8 M KF, 20 mM EDTA, 0.01% BSA;
6.7 nM TK-Antibody, 62.5 nM XL665;
Reaction at 23° C. for 60 minutes;
Testing Equipment:
Envision (PerkinElmer #2104)
By virtue of an inhibition curve of inhibition ratios of test compounds under various concentrations, a ratio of 50% of inhibition ratios of the test compounds ($IC_{50}$ value).
Other kinases (e.g., inhibitory activity of Lck and LynA is determined by replacing the Btk with various kinases and performing operations the same as that in the above method).
With respect to the $IC_{50}$ value of the target compounds in the present invention, results are as shown in Table 1 as follows:

TABLE 1

| Embodiment No. | $IC_{50}$ (nM) |
|---|---|
| 6 | 0.27 |
| 8 | 0.64 |
| 13 | 0.46 |
| 14 | 5.82 |
| 15 | 6.90 |
| 16 | 16.7 |
| 22 | 145 |
| 24 | 78 |
| 29 | >1000 |
| 30 | 76.8 |
| 34 | 209 |
| 35 | 176 |
| 36 | >1000 |
| 40 | 23 |
| 42 | 0.9 |
| 51 | 5.1 |
| Ibrutinib | 0.19 |

In addition, the Btk selective inhibitory activity of the compounds in the present invention on the other kinases, particularly Lck and LynA, is calculated based on the $IC_{50}$ value of the various kinases and is shown in Table 2 as follows:

TABLE 2

| Embodiment No. | Lck[$IC_{50}$]/Btk[$IC_{50}$] | LynA[$IC_{50}$]/Btk[$IC_{50}$] |
|---|---|---|
| 6 | 285 | 137 |
| 8 | 139 | 62.5 |
| 13 | 420 | 507 |
| Ibrutinib | 158 | 320 |

It is shown from the results that, the target compounds in the present invention have the Btk inhibitory activity and Btk selective inhibitory activity on the other kinases.

Biological Embodiment 2: Human and Rat Liver Microsome Stability Test

Preparation of Buffer Solution:
1. 100 mM potassium phosphate buffer solution, pH of 7.4
2. 10 mM $MgCl_2$
Preparation of Test Compound Solution:
1. A test compound solution (10 mM, 5 μL) was diluted with a methanol solution (495 μL), and a 100 μM solution was prepared;
2. Preparation of a working solution: the above solution (50 μL) was diluted with the potassium phosphate buffer solution (450 μL, 100 mM) so as to obtain diluents (10 μM).
NADPH Regeneration System (Final Concentration 1 Unit/mL of Isocitrate Dehydrogenase):
1. beta-NADP, supplier: sigma Cat. No. N0505
2. isocitric acid supplier: Sigma Cat. No. 11252
3. isocitrate dehydrogenase, supplier: sigma Cat. No. 12002
Preparation of Liver Microsome Solution (Final Concentration of 0.5 mg Protein/mL)

| Microsome | Information | Source |
|---|---|---|
| Human liver microsome | Cat No. 452117 Lot No. 38290 | BD |
| s rat liver microsome | Cat No. R1000 Lot No. 1310030 | Xenotech |

Stop Solution:
Cold acetonitrile containing 100 ng/mL of tolbutamide and 100 ng/mL of labetalol serves as an internal standard
1. a 10 μL/well of working solution was added into plates (T0, T5, T10, T20, T30, T60, NCF60) beyond the blank;
2. a 80 μL/well of microsome solution was added, and incubation was performed at 37° C. for 10 min;
3. a 10 μL of 100 mM phosphate buffer solution was added into each well of an NCF60 plate, the plate was placed in a warm bath at 37° C., and timing started;

| Time point | Start time | End time |
|---|---|---|
| NCF60 | 1:00:00 | 0:00:00 |

4. a 10 μL/well of NADPH regeneration system was added after preheating, and a reaction started;
5. incubation was performed at 37° C., and timing started

| Time point | Start time | End time |
|---|---|---|
| Blank | 1:00:00 | 0:00:00 |
| T60 | 1:00:00 | 0:00:00 |
| T30 | 0:59:39 | 0:29:39 |
| T20 | 0:59:18 | 0:39:18 |
| T10 | 0:58:53 | 0:48:53 |
| T5 | 0:58:17 | 0:53:17 |
| T0 | Add stop solution first, then add microsome solution and NADPH regenerating system | |

6. a 300 μL/well of stop solution was added (4° C., containing 100 ng/mL of tolbutamide and 100 ng/mL of labetalol) to end the reaction;
7. the plate was shaken for 10 min;
8. centrifugation was performed at 4° C. at a rotation speed of 4000 rpm; and
9. sample LC/MS/MS detection was performed.

Data Analysis Use Equation of First Order Kinetics to Calculate t½ and Clint(Mic):
equation of first order kinetics:

$$C_t = C_0 \cdot e^{-k_e \cdot t} \quad \quad 5$$

when $C_t = \frac{1}{2} C_0$, $$T_{1/2} = \frac{Ln2}{k_e} = \frac{0.693}{k_e} \quad \quad 10$$

$$CL_{int(mic)} = \frac{0.693}{\text{In vitro } T_{1/2}} \cdot \frac{1}{\text{mg/mL microsomal protein in reaction system}}$$

$$CL_{int(liver)} = CL_{int(mic)} \cdot \frac{\text{mg microsomes}}{\text{g liver}} \cdot \frac{\text{g liver}}{\text{kg body weight}}$$

Experimental results are shown in Table 3 as follows:

TABLE 3

| | | | HLM 0.5 | | | |
|---|---|---|---|---|---|---|
| Embodiment No. | $R^2$ | $T_{1/2}$ (min) | $CL_{int(mic)}$ (ul/min/mg) | $CL_{int(liver)}$ (ml/min/kg) | Remaining (T = 60 min) | Remaining (*NCF = 60 min) |
| 6 | 0.98 | 4.3 | 324.7 | 292.2 | 0.2% | 105.9% |
| 8 | 0.99 | 3.7 | 373.9 | 336.5 | 0.0% | 105.8% |
| 13 | 0.97 | 20.5 | 67.6 | 60.8 | 14.0% | 93.1% |
| Reference compound Ibrutinib | 0.9289 | 2.7 | 504.6 | 454.2 | 0.8% | 105.1% |

| | | | RLM 0.5 | | | |
|---|---|---|---|---|---|---|
| Embodiment No. | $R^2$ | $T_{1/2}$ (min) | $CL_{int(mic)}$ (ul/min/mg) | $CL_{int(liver)}$ (ml/min/kg) | Remaining (T = 60 min) | Remaining (*NCF = 60 min) |
| 6 | 0.99 | 8.9 | 155.4 | 279.8 | 1.1% | 105.4% |
| 8 | 0.98 | 3.8 | 365.7 | 658.3 | 0.2% | 111.2% |
| 13 | 0.94 | 13.7 | 101.0 | 181.7 | 5.0% | 94.7% |
| Reference compound Ibrutinib | 0.9995 | 1.3 | 1030.7 | 1855.2 | 0.6% | 110.2% |

*NCF: the abbreviation of no co-factor. No NADPH regenerating system is added into NCF sample (replaced by buffer) during the 60 min-incubation, if the NCF remaining is less than 60%, then Non-NADPH dependent occurs.

$R^2$ is the correlation coefficient of the linear regression for the determination of kinetic constant T½ is half life and CLint (mic) is the intrinsic clearance CLint(liver) = CLint (mic) * mg microsomal protein/g liver weight * g liver weight/kg body weightmg microsomal protein/g liver weight: 45 mg/g for 5 species Liver weight: 88 g/kg, 40g/kg, 32 g/kg, 30 g/kg and 20 g/kg for mouse, rat, dog, monkey and human.

By comparing $CL_{int(liver)}$ (ml/min/kg) values of the various compounds from the experimental results, it is known that, the compounds in the present invention have better stability than Ibrutinib.

Biological Embodiment 3: Influences of In-Vitro Test Compounds on PBMC/B/T Cell Activation 1. Reagents and Instruments
1)

| | Reagents\instrument | Vendor | Catalog # |
|---|---|---|---|
| 1 | RPMI Medium 1640 | Invitrogen | 22400089 |
| 2 | Fetal Bovine Serum | Corning | 35-076-CV |
| 3 | Penicillin-Streptomycin Solution | Hyclone | SV30010 |
| 4 | DPBS | Corning | 21-031-CV |
| 6 | Human T cell Enrichment Kit | STEMCELL | 19051 |
| 7 | Human B cell Enrichment Kit | STEMCELL | 19054 |
| 8 | Dynabeads ® Human T-Activator CD3/CD28 | Gibco | 11132D |

2)

| | Instrument | Vendor | Model # |
|---|---|---|---|
| 1 | BD FACSCanto ™ II | BD | FACSCanto ™ II |

2. Antibody

| | Antibody | Vendor |
|---|---|---|
| 1 | Donkey anti-human IgM | Jackson Immuno Research |
| 2 | FITC Mouse Anti-Human CD4 | BD |
| 3 | PerCP-Cy ™5.5 Mouse Anti-Human CD8 | BD |
| 4 | APC anti-human CD69 | BioLegend |
| 5 | PE Mouse Anti-Human CD20 | BD |
| 6 | LIVE/DEAD Fixable Violet Dead Cell Stain Kit | Invitrogen |

3. Sample Table

| . Cpd NO | weight | DMSO Vol. | Stock concentration |
|---|---|---|---|
| 45 | 6.17 mg | 659.9 ul | 20 mM |
| 6 | 1.4 mg | 153.7 ul | 20 mM |
| 13 | 11.97 mg | 1594 ul | 20 mM |
| Contrast (Ibrutinib) | 5.26 mg | 597 ul | 20 mM |
| 47 | 7.58 mg | 978.3 ul | 20 mM |

4. Method
4.1 Sample Preparation

| ID | concentration |
|---|---|
| C1 | 40 uM |
| C2 | 4 uM |
| C3 | 0.4 uM |
| C4 | 20 uM |
| C5 | 2 uM |
| C6 | 0.2 uM |

Note:
C1, C2, C3 is used for PBMC/B cell activation;
C4, C5, C6 is used for T cell activation 4.2 Preparation of Anti-Human IgM

| ID | Concentration | Note |
|---|---|---|
| Stock | 1.3 mg/ml | NA |
| C1 | 20 ug/ml | For B cell activation |
| C2 | 40 ug/ml | For PBMC activation |

4.3 Isolation of B Cells and T Cells
Cell Isolation Programs Shall Refer to STEMCELL Kits
4.4 Co-Culture
4.4.1 Activation of B Cells
The co-culture system is as follows:

| component | Final Concentration |
|---|---|
| Anti-human IgM | 5 ug/ml |
| CPD | 10 uM, 1 uM, 0.1 uM |

4.4.2 Activation of PBMC
The co-culture system is as follows:

| component | Final Concentration |
|---|---|
| Anti-human IgM | 10 ug/ml |
| CPD | 10 uM, 1 uM, 0.1 uM |

4.4.3 Activation of T Cells
The co-culture system is as follows:

| component | Final Concentration |
|---|---|
| CD3/CD28 dynabeads | Beads:T = 1:1 |
| CPD | 10 uM, 1 uM, 0.1 uM |

Figure 2:
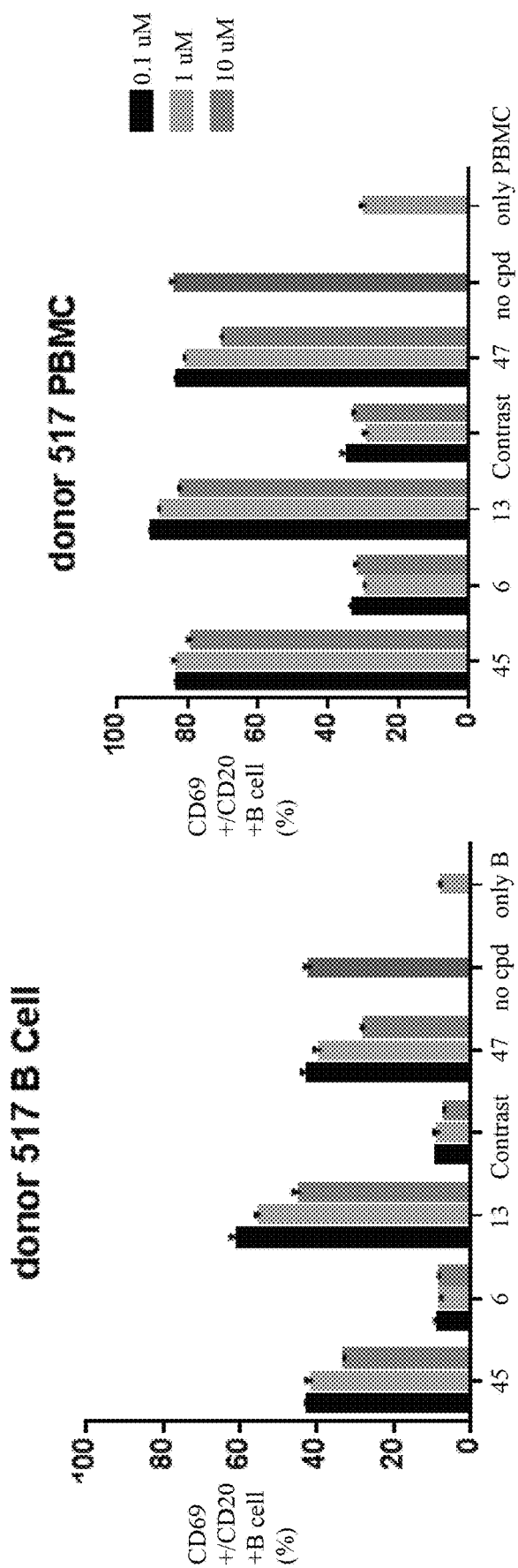
FIG. 2(A) and FIG. 2(B) are inhibitory effects of a test sample on activation of donor 517 B cells and peripheral blood monouclear cells.
Figure 3:
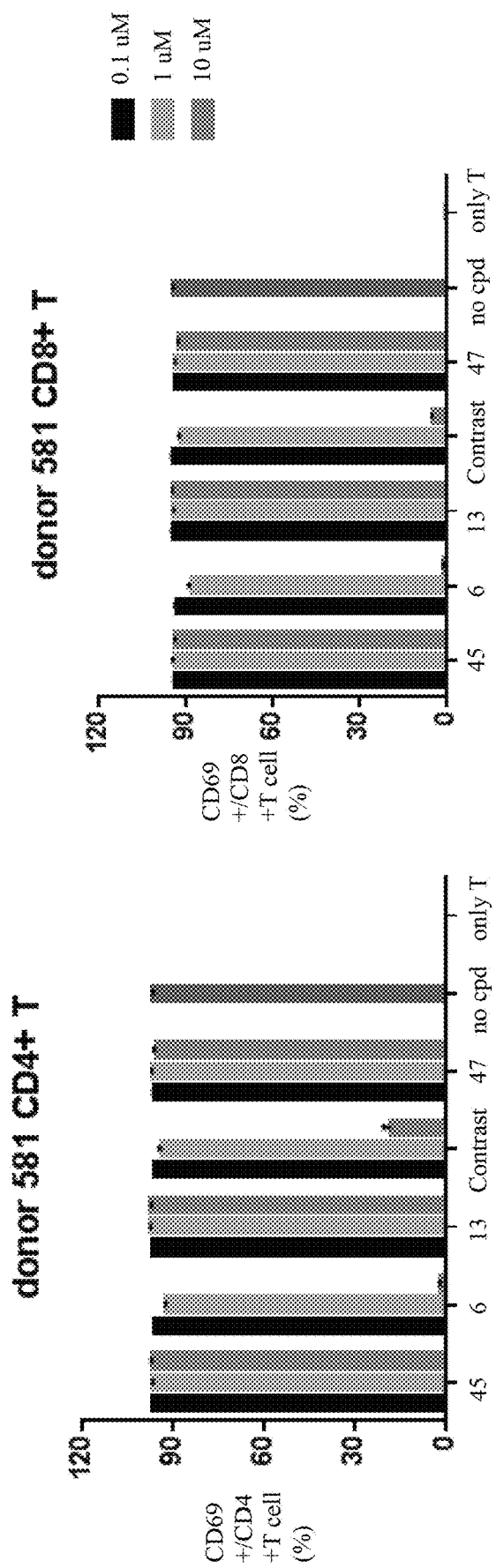
FIG. 3(A) and FIG. 3(B) are inhibitory effects of a test sample on activation of donor 581 T cells.
Figure 4:
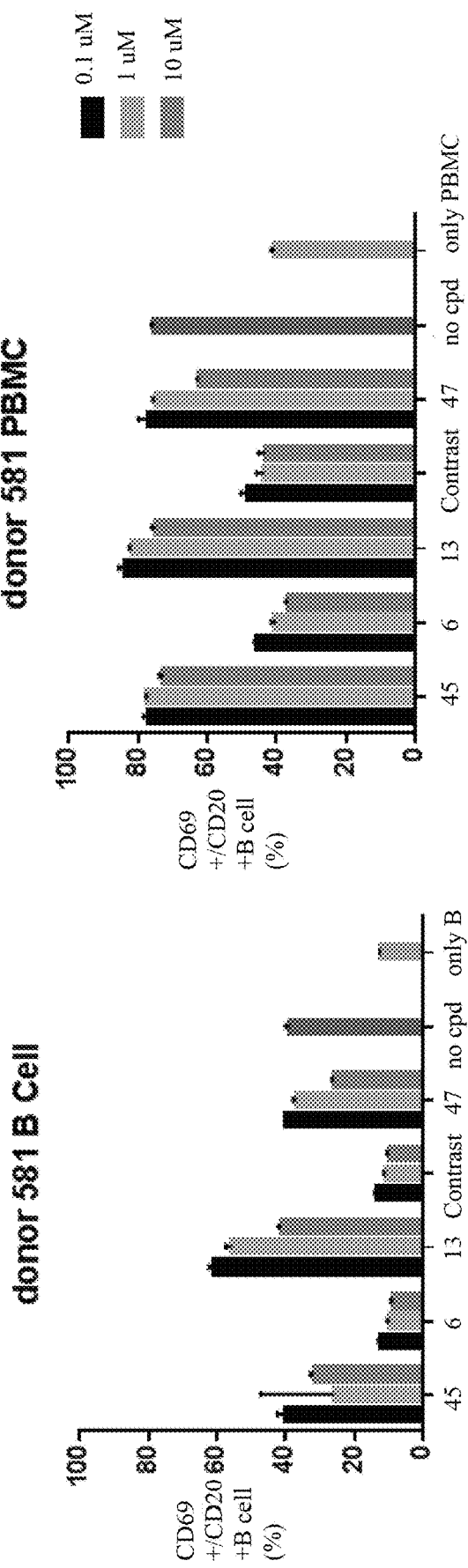
FIG. 4(A) and FIG. 4(B) are inhibitory effects of a test sample on activation of donor 581 B cells and peripheral blood monouclear cells.
Figure 5:
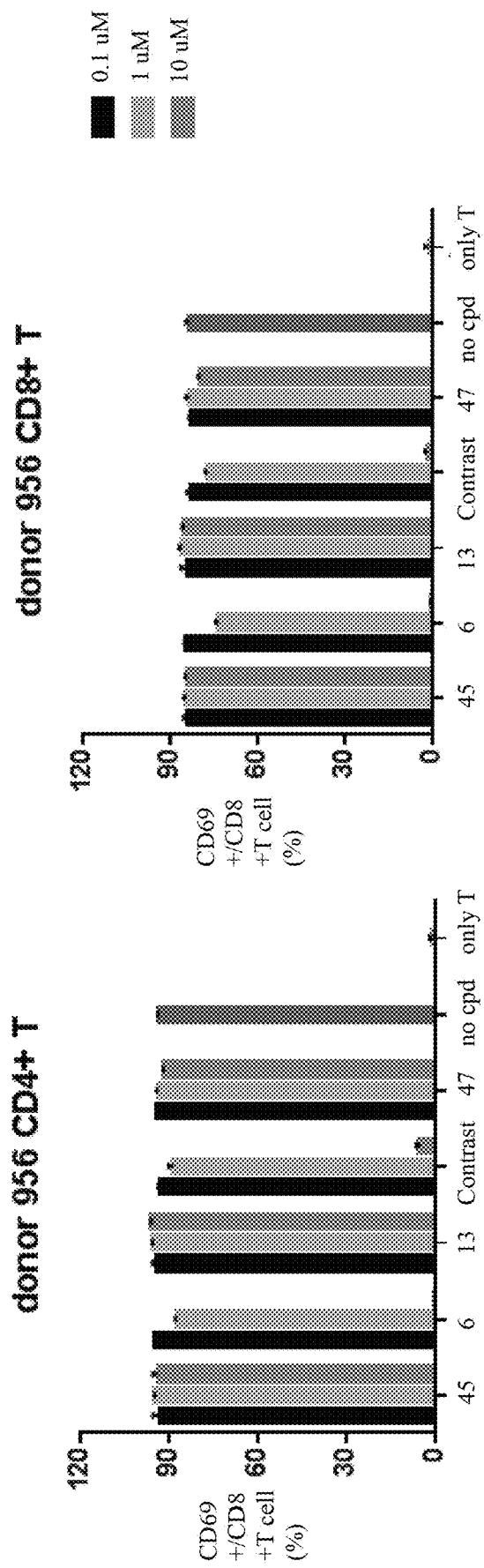
FIG. 5(A) and FIG. 5(B) are inhibitory effects of a test sample on activation of donor 956 T cells.
Figure 6:
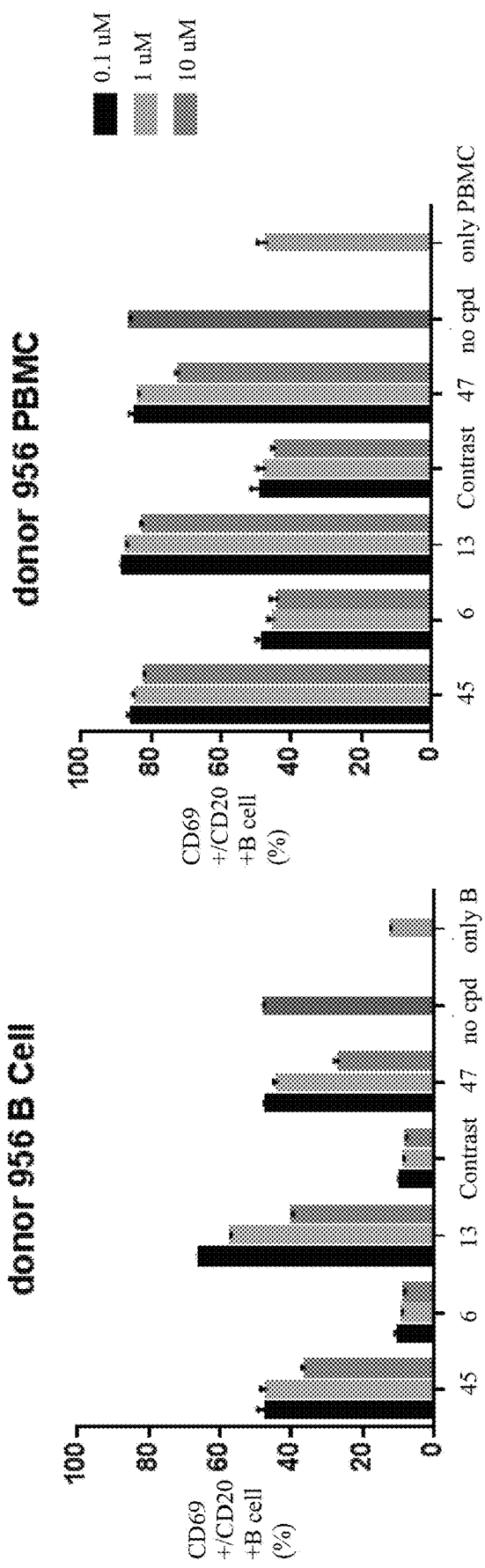
FIG. 6(A) and FIG. 6(B) are inhibitory effects of a test sample on activation of donor 956 B cells and peripheral blood monouclear cells.

Antibody Staining and Data Analysis
Antibody staining was performed within 24 hours before co-culture according to a standard method.
4.5.1 Activation of PBMC and B Cells
PE Mouse Anti-Human CD20
APC Anti-Human CD69
LIVE/DEAD Fixable Violet Dead Cell Stain Kit
4.5.2 Activation of T Cells
FITC Mouse Anti-Human CD4
PerCP-Cy™5.5 Mouse Anti-Human CD8
APC anti-human CD69
LIVE/DEAD Fixable Violet Dead Cell Stain Kit
5. Results
Donor 517
T Cell Activation is shown in FIG. 1(A) and FIG. 1(B).
Donor 517
B and PBMC Activation is shown in FIG. 2(A) and FIG. 2(B).
Donor 581
T Cell Activation is shown in FIG. 3(A) and FIG. 3(B).
Donor 581
B and PBMC Activation is shown in FIG. 4(A) and FIG. 4(B).
Donor 956
T Cell Activation is shown in FIG. 5(A) and FIG. 5(B).
Donor 956
B and PBMC Activation is shown in FIG. 6(A) and FIG. 6(B).
The embodiment compound 6 and the contrast (Ibrutinib) show obvious B cell activity inhibition effects under a concentration of 0.1 uM, and show a T cell activity inhibition effect under a concentration of 10 uM.

Biological Embodiment 4: Analysis of Influences of Test Compounds on p-Btk/t-Btk, p-PLCγ/t-PLCγ and p-Erk/t-Erk Expression Levels of DOHH2 Cells by Virtue of Western Blotting 1. Reagents

| | Reagents\instrument | Vendor | Catalog # |
|---|---|---|---|
| 1 | RIPA Buffer | Sigma | R0278 |
| 2 | Phosphatase Inhibitor Cocktail 2 | Sigma | P5726 |
| 3 | Protease Inhibitor Cocktail | Roche | 04693124001 |
| 4 | Pierce ™ BCA Protein Assay Kit | Thermo Scientific | 23225 |
| 5 | NuPAGE ® LDS Sample Buffer (4X) | Thermo Scientific | NP0008 |
| 6 | NuPAGE ® Sample Reducing Agent (10X) | Thermo Scientific | NP0009 |
| 7 | PageRuler ™ Prestained Protein Ladder | Thermo Scientific | 26616 |
| 8 | NuPAGE ® Novex 4-12% Bis-Tris Gel 1.5 mm, 20 Well | Thermo Scientific | WG1402A |
| 10 | NuPAGE ® Novex 4-12% Bis-Tris Gel 1.0 mm, 26 Well | Thermo Scientific | WG1403BOX |
| 11 | NuPAGE ® MOPS SDS Running Buffer (20X) | Thermo Scientific | B0001 |
| 12 | iBlot ® 2 Transfer Stack Regular | Thermo Scientific | IB23001 |
| 13 | 20XTBS | Bio-Serve | BS-P-15 |
| 14 | Tween 20 | Sigma | P1379 |
| 15 | West Femto Maximum Sensitivity Substrate | Thermo Scientific | 34096 |
| 16 | Bovine Serum Albumin | BBI life sciences & services | A600332 |
| 17 | Nonfat Milk | Guangming | / |

2. Instruments

| | Instrument | Vendor | Model # |
|---|---|---|---|
| 1 | Electro- thermal incubator | Boxun | HPX-9162 MBE |
| 2 | SpectraMax i3x | Molecular Devices | i3x |
| 3 | Digital Dry Baths | Qiling | GL-150B |
| 4 | XCell SureLock ® Mini-cell | Thermo Scientific | Mini-cell |
| 5 | PowerEase ® 500 | Thermo Scientific | 500 |
| 6 | iBlot ® 2 Gel Transfer Device | Thermo Scientific | iBlot2 |
| 7 | 5200multi | Tanon | 5200multi |

3. Antibody

| | Antibody | Vendor | Catalog # | MW(kDa) | Source |
|---|---|---|---|---|---|
| 1 | p-BTK Antibody | Cell Signaling Technology | 87141S | 78 | Rabbit |
| 2 | t-BTKAntibody | Cell Signaling Technology | 8547S | 77 | Rabbit |
| 3 | p-PLCγ Antibody | Cell Signaling Technology | 2821S | 155 | Rabbit |
| 4 | t-PLCγ Antibody | Cell Signaling Technology | 2822S | 155 | Rabbit |
| 5 | p-ERK Antibody | Cell Signaling Technology | 4377S | 42, 44 | Rabbit |
| 6 | t-ERK Antibody | Cell Signaling Technology | 9107S | 42, 44 | Mouse |
| 7 | Actin Antibody | Cell Signaling Technology | 4967S | 45 | Rabbit |

4. Sample Preparation:

| Serial | Sample name |
|---|---|
| 1 | DMSO |
| 2 | DMSO |
| 3 | Compound 6, 5 nM |
| 4 | Compound 6, 5 nM |
| 5 | Compound 6, 100 nM |
| 6 | Compound 6, 100 nM |
| 7 | Compound 6, 2000 nM |
| 8 | Compound 6, 2000 nM |
| 9 | Compound 13, 5 nM |
| 10 | Compound 13, 5 nM |
| 11 | Compound 13, 100 nM |
| 12 | Compound 13, 100 nM |
| 13 | Compound 13, 2000 nM |
| 14 | Compound 13, 2000 nM |
| 15 | Compound 45, 5 nM |
| 16 | Compound 45, 5 nM |
| 17 | Compound 45, 100 nM |
| 18 | Compound 45, 100 nM |
| 19 | Compound 45, 2000 nM |
| 20 | Compound 45, 2000 nM |
| 21 | Compound 47, 5 nM |
| 22 | Compound 47, 5 nM |
| 23 | Compound 47, 100 nM |
| 24 | Compound 47, 100 nM |
| 25 | Compound 47, 2000 nM |
| 26 | Compound 47, 2000 nM |
| 27 | Contrast (Ibrutinib), 5 nM |
| 28 | Contrast (Ibrutinib), 5 nM |
| 29 | Contrast (Ibrutinib), 100 nM |
| 30 | Contrast (Ibrutinib), 100 nM |

-continued

| Serial | Sample name |
|---|---|
| 31 | Contrast (Ibrutinib), 2000 nM |
| 32 | Contrast (Ibrutinib), 2000 nM |

5. Cell Culture

1) DOHH2 cells on a logarithmic phase were collected;

2) a cell concentration was adjusted to a needed concentration;

3) 2 ml of cell suspension was added into a 6-well plate for performing culture, three different concentrations, that is, 5 nM, 100 nM and 2000 nM, of test samples were respectively set, and each concentration was repeated once;

Plate 1:

| DOHH2 |
|---|
| Vehicle, DMSO |
| DOHH2 |
| Vehicle, DMSO |

Plate 2:

| DOHH2 | DOHH2 | DOHH2 |
|---|---|---|
| Compound 6, 5 nM | Compound 6, 100 nM | Compound 6, 2000 nM |
| DOHH2 | DOHH2 | DOHH2 |
| Compound 6, 5 nM | Compound 6, 100 nM | Compound 6, 2000 nM |

Plate 3:

| DOHH2 | DOHH2 | DOHH2 |
|---|---|---|
| Compound 13, 5 nM | Compound 13, 100 nM | Compound 13, 2000 nM |
| DOHH2 | DOHH2 | DOHH2 |
| Compound 13 5 nM | Compound 13, 100 nM | Compound 13, 2000 nM |

Plate 4:

| DOHH2 | DOHH2 | DOHH2 |
|---|---|---|
| Compound 45, 5 nM | Compound 45, 100 nM | Compound 45, 2000 nM |
| DOHH2 | DOHH2 | DOHH2 |
| Compound 45, 5 nM | Compound 45, 100 nM | Compound 45, 2000 nM |

Plate 5:

| DOHH2 | DOHH2 | DOHH2 |
|---|---|---|
| Compound 47, 5 nM | Compound 47, 100 nM | Compound 47, 2000 nM |
| DOHH2 | DOHH2 | DOHH2 |
| Compound 47, 5 nM | Compound 47, 100 nM | Compound 47, 2000 nM |

Plate 6:

| DOHH2 | DOHH2 | DOHH2 |
|---|---|---|
| Contrast (Ibrutinib), 5 nM | Contrast (Ibrutinib), 100 nM | Contrast (Ibrutinib), 2000 nM |
| DOHH2 | DOHH2 | DOHH2 |
| Contrast (Ibrutinib), 5 nM | Contrast (Ibrutinib), 100 nM | Contrast (Ibrutinib), 2000 nM |

4) test samples were added into plate wells, and DMSO served as control, wherein a final concentration of the DMSO was 0.1%;

5) culture was performed for 1 h; and 6) after cultured for 1 h, the DOHH2 cells and the test samples were washed with a PBS solution in an amount of 10 times of the volume for three times and then stimulated with anti-IgG (30 μg/mL; ab98531) for 2 min.

6. protein extraction and quantification 1) cells were collected, and centrifugation was performed at 1200 rpm for 5 min;

2) the cells were leached once with 1×PBS in an ice bath;

3) 0.5 ml of 1×RIPA buffer solution (containing 1% of protease inhibitor Cocktail and 1% of phosphatase inhibitor Cocktail 2) in an ice bath was added into each bottle, and incubation was performed in the ice bath for 30 min;

4) centrifugation was performed at 4° C. at 14000 rpm for 10 min, and liquid supernatant was collected;

5) a protein concentration was determined by using Pierce™ BCA Protein Assay Kit; and 6) according to BCA protein quantification results, all samples were diluted to the same final concentration by adding 4×LDS sample buffer and 10× sample reducing agent into the RIPA buffer solution, and the solution was heated at 100° C. for 10 min.

6. Western Blotting 1) samples were added into NuPAGE® Novex 4-12% Bis-Tris gel in an amount of 10 μL per well, 80V voltage 30 min, 120V voltage 90 min;

Gel 1:

| Serial | Sample name |
|---|---|
| 1 | DMSO |
| 2 | DMSO |
| 3 | Compound 6, 5 nM |
| 4 | Compound 6, 5 nM |
| 5 | Compound 6, 100 nM |
| 6 | Compound 6, 100 nM |
| 7 | Compound 6, 2000 nM |
| 8 | Compound 6, 2000 nM |
| 9 | Compound 13, 5 nM |
| 10 | Compound 13, 5 nM |
| 11 | Compound 13, 100 nM |
| 12 | Compound 13, 100 nM |
| 13 | Compound 13, 2000 nM |
| 14 | Compound 13, 2000 nM |
| 15 | Compound 45, 5 nM |
| 16 | Compound 45, 5 nM |
| 17 | Compound 45, 100 nM |
| 18 | Compound 45, 100 nM |
| 19 | Compound 45, 2000 nM |
| 20 | Compound 45, 2000 nM |

Gel 2:

| Serial | Sample name |
|---|---|
| 1 | DMSO |
| 2 | DMSO |
| 3 | Compound 47, 5 nM |
| 4 | Compound 47, 5 nM |
| 5 | Compound 47, 100 nM |
| 6 | Compound 47, 100 nM |
| 7 | Compound 47, 2000 nM |
| 8 | Compound 47, 2000 nM |

| Serial | Sample name |
|---|---|
| 9 | Contrast (Ibrutinib), 5 nM |
| 10 | Contrast (Ibrutinib, 5 nM |
| 11 | Contrast (Ibrutinib, 100 nM |
| 12 | Contrast (Ibrutinib, 100 nM |
| 13 | Contrast (Ibrutinib, 2000 nM |
| 14 | Contrast (Ibrutinib, 2000 nM |

2) proteins were transferred to a nitrocellulose membrane by an iBlot®2 Gel transfer device for 7 min;

3) the proteins and 1×TBST containing 5% of skim milk were cultured at a room temperature for 1 h;

4) 1×TBST was washed for three times for 5 min each time;

5) the membrane and 5-10 mL of diluted initial antibody were cultured at 4° C. and then slowly shaken to stay overnight;

6) 1×TBST was washed for three times for 10 min each time;

7) the membrane and an HRP-conjugated secondary antibody were cultured at a room temperature and then slowly shaken for 1 h;

8) 1×TBST was washed for three times for 10 min each time;

9) an HRP substrate in a West Femto Maximum Sensitivity kit was added; and 10) chemiluminiscence was detected by Tanon 5200 multi.

7. Quantification of strip intensity

Intensity of each strip was quantified by using Image quant densitometry software.

Results

Figure 7:
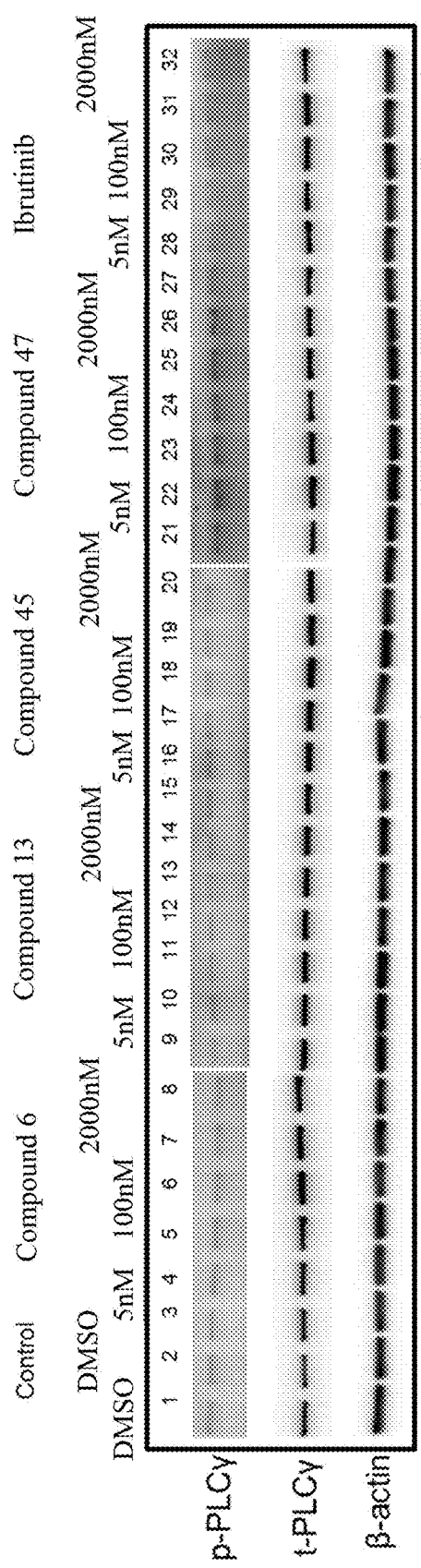
FIG. 7(A) and FIG. 7(B) are relative expression levels of p-Btk/t-Btk of DOHH2 cells treated by a test sample and stimulated with anti-lgG.
Figure 7:
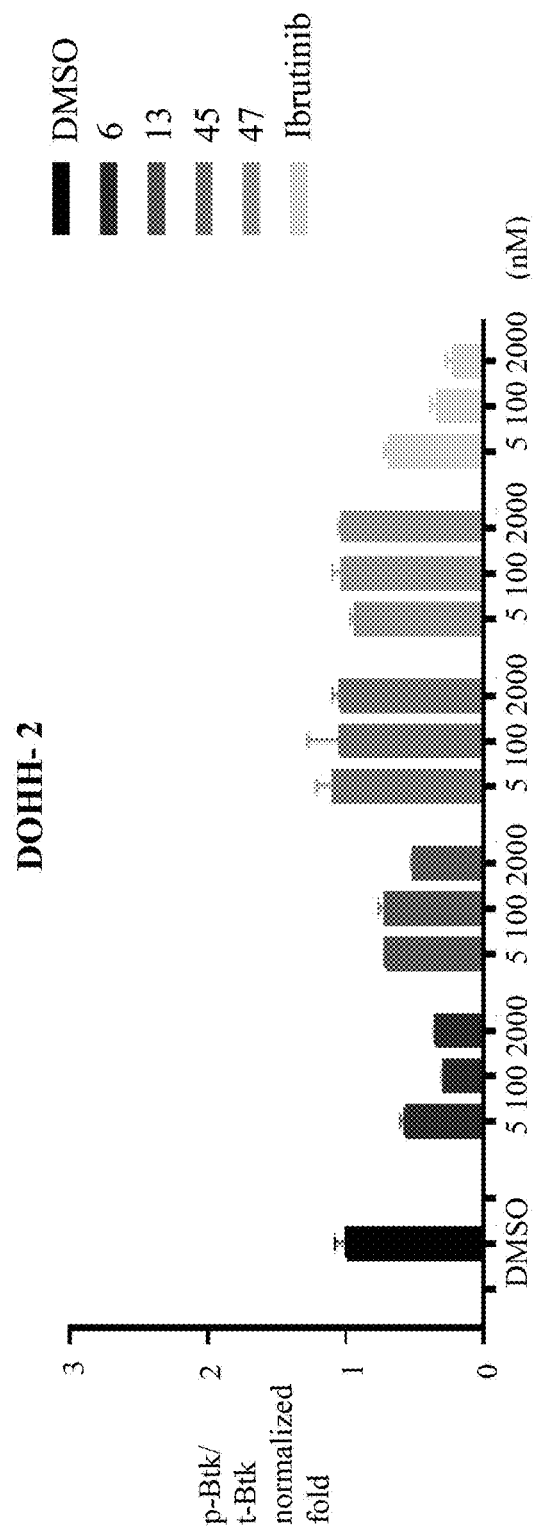

After treated by test samples, the DOHH2 cells were stimulated with anti-IgG, a relative expression level of p-Btk/t-Btk of the cells was analyzed by Western blotting, and results are shown in FIG. 7(A) and FIG. 7(B).

After treated by test samples, the DOHH2 cells were stimulated with anti-IgG, a relative expression level of p-PLCγ/t-PLCγ of the cells was analyzed by Western blotting, and results are shown in FIG. 8(A) and FIG. 8(B).

Figure 9:
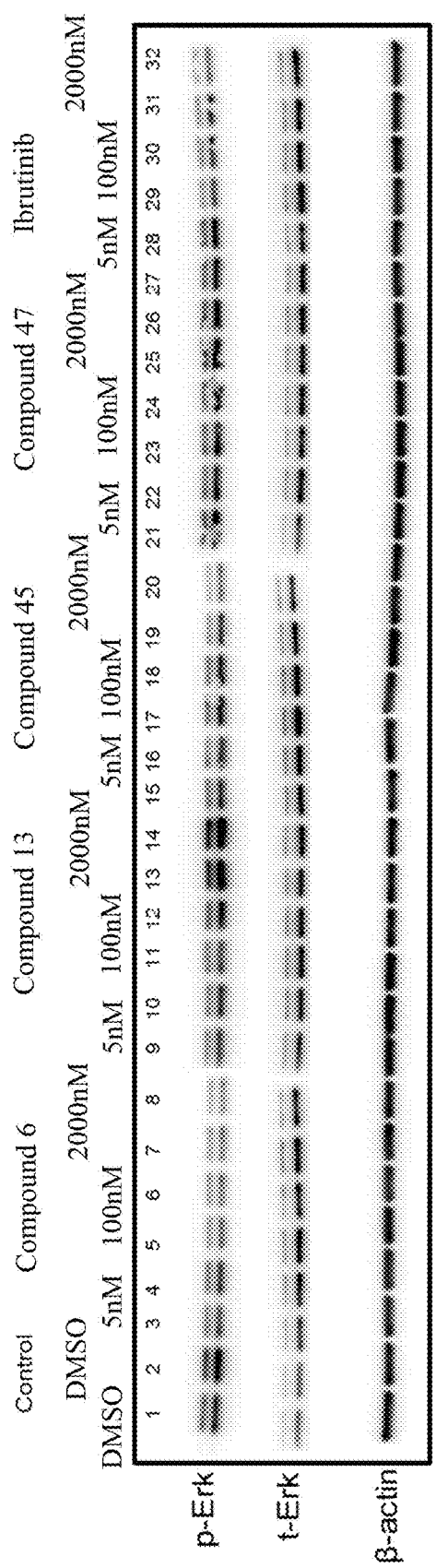
FIG. 9(A) and FIG. 9(B) are relative expression levels of p-Erk/t-Erk of DOHH2 cells treated by a test sample and stimulated with anti-lgG.
Figure 9:
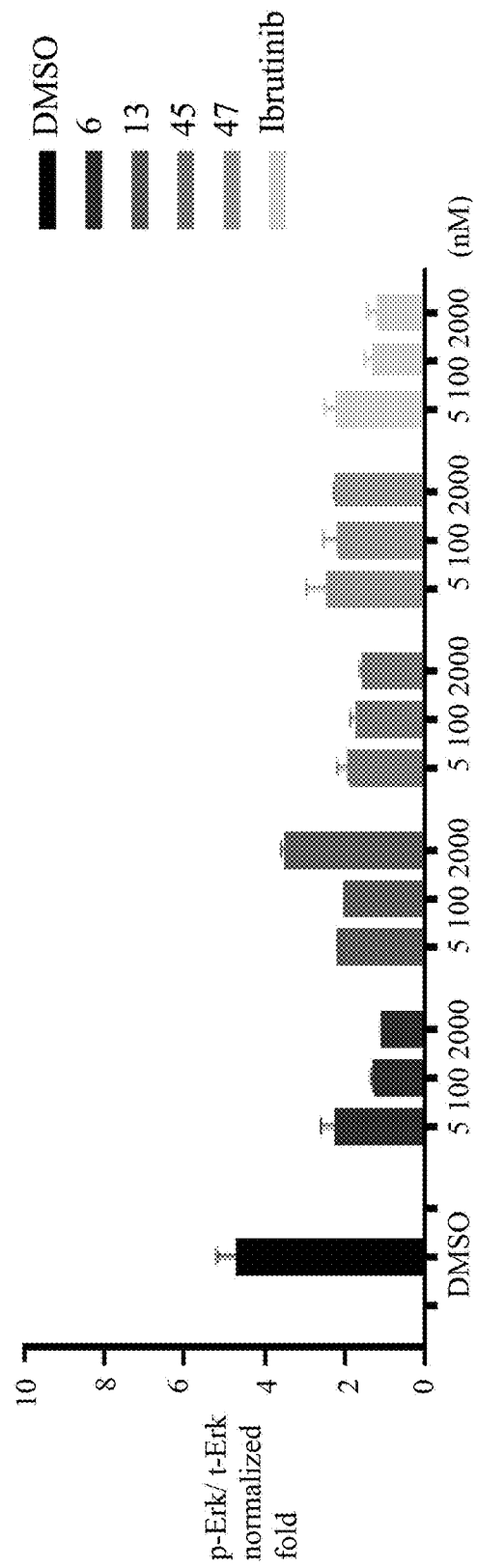
Figure 10:
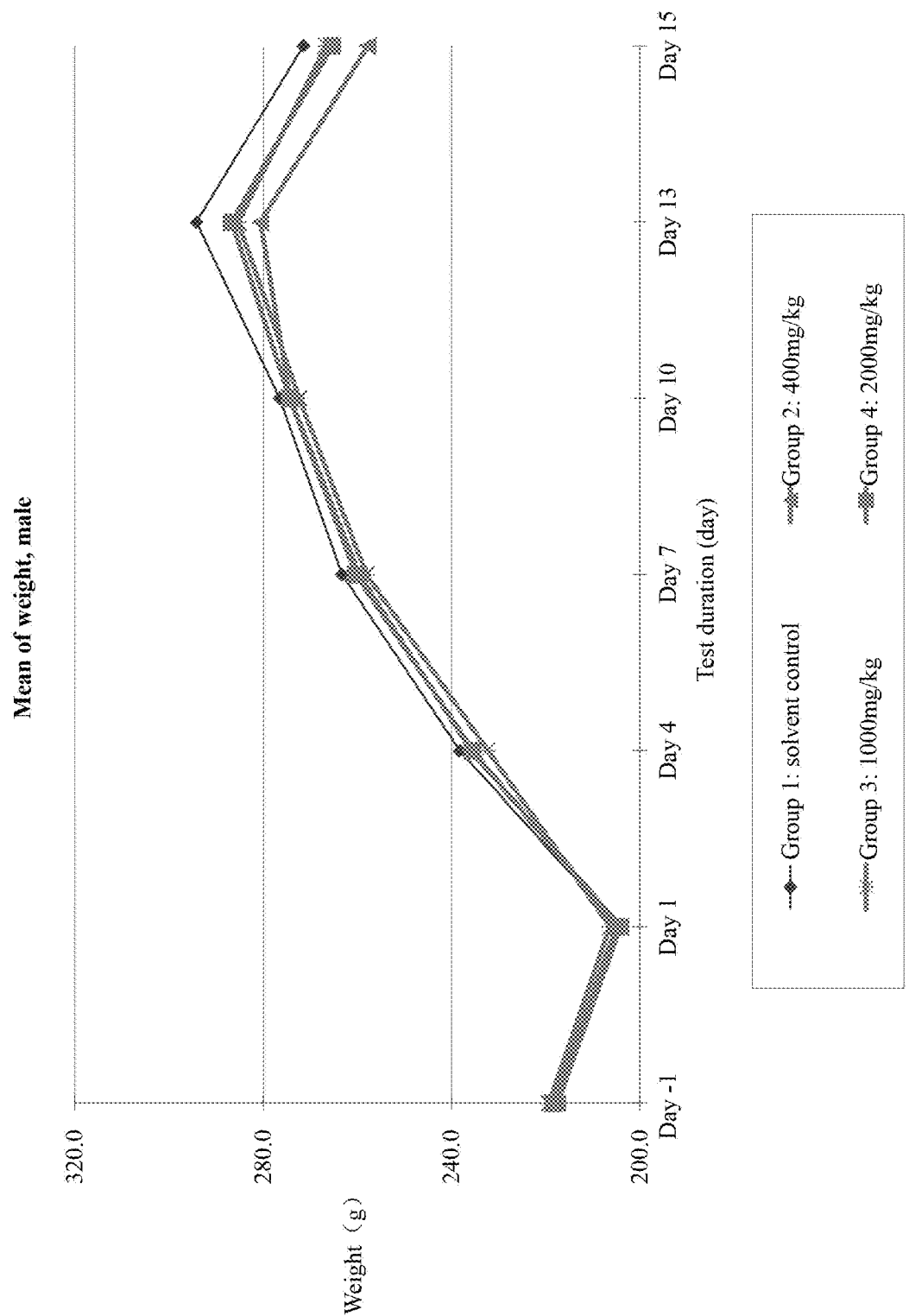
FIG. 10 is a body weight change of male SD rats taking a test sample.
Figure 11:
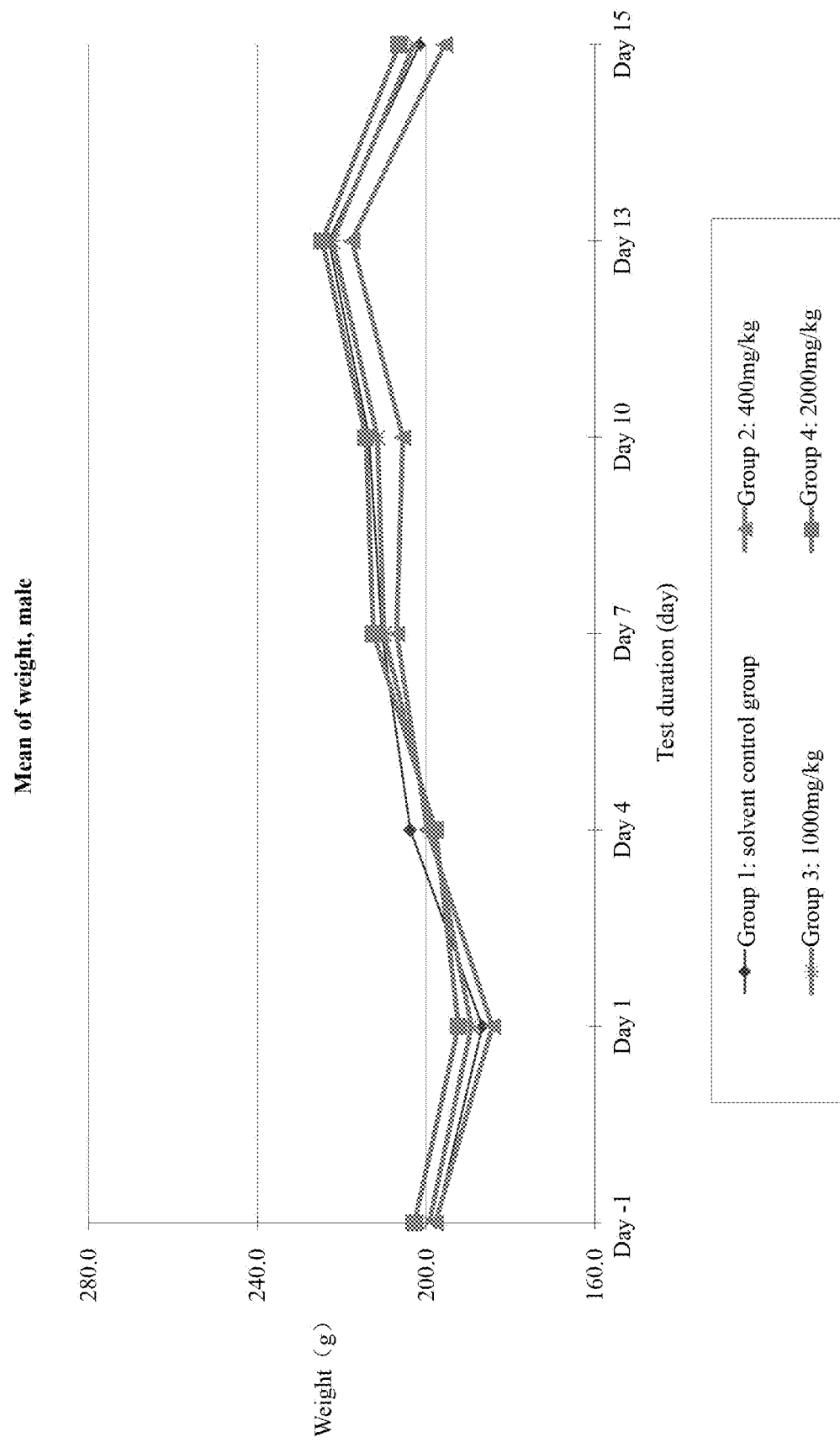
FIG. 11 is a body weight change of female SD rats taking a test sample.
Figure 12:
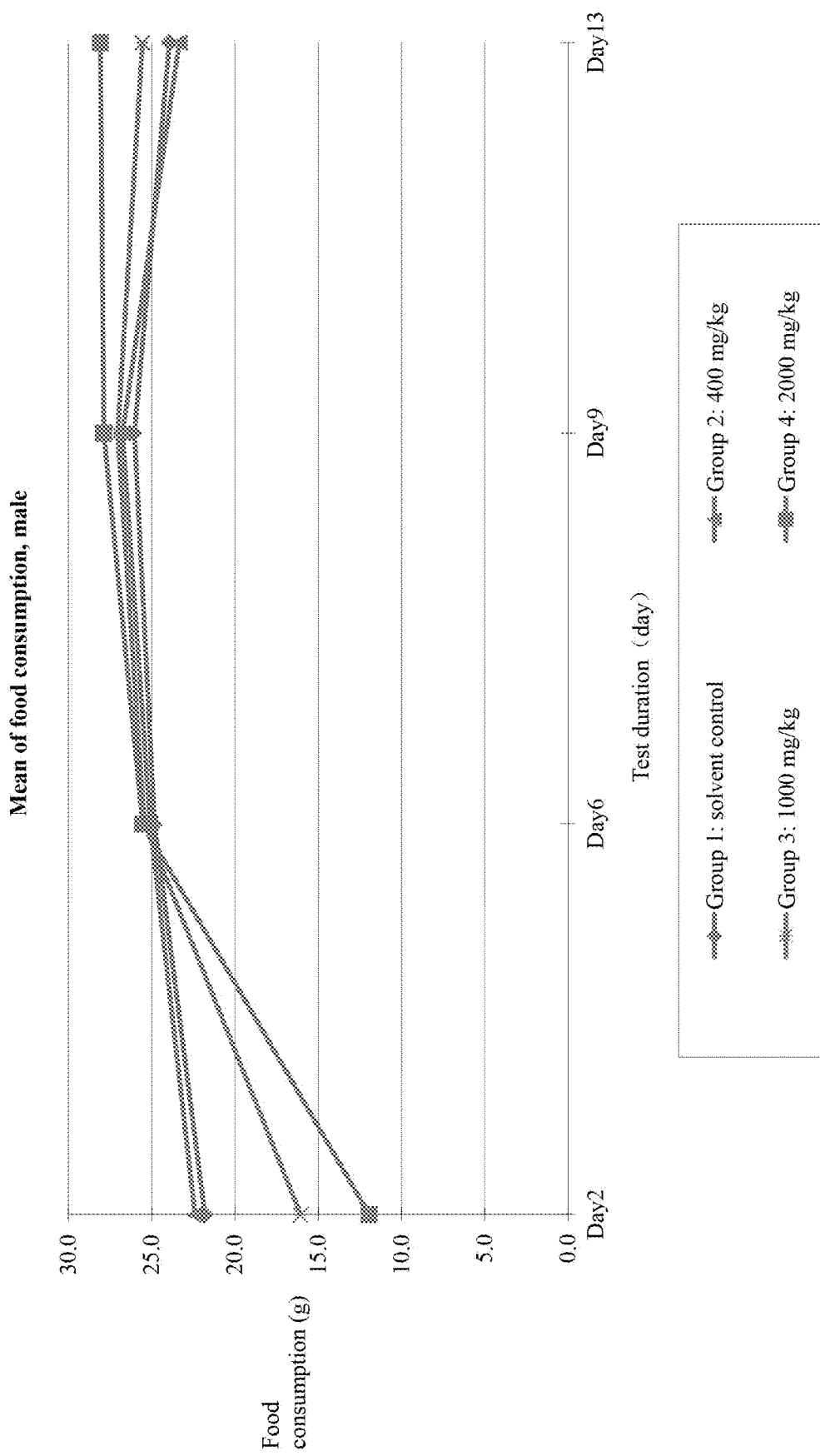
FIG. 12 is a change of food intake of male SD rats taking a test sample.
Figure 13:
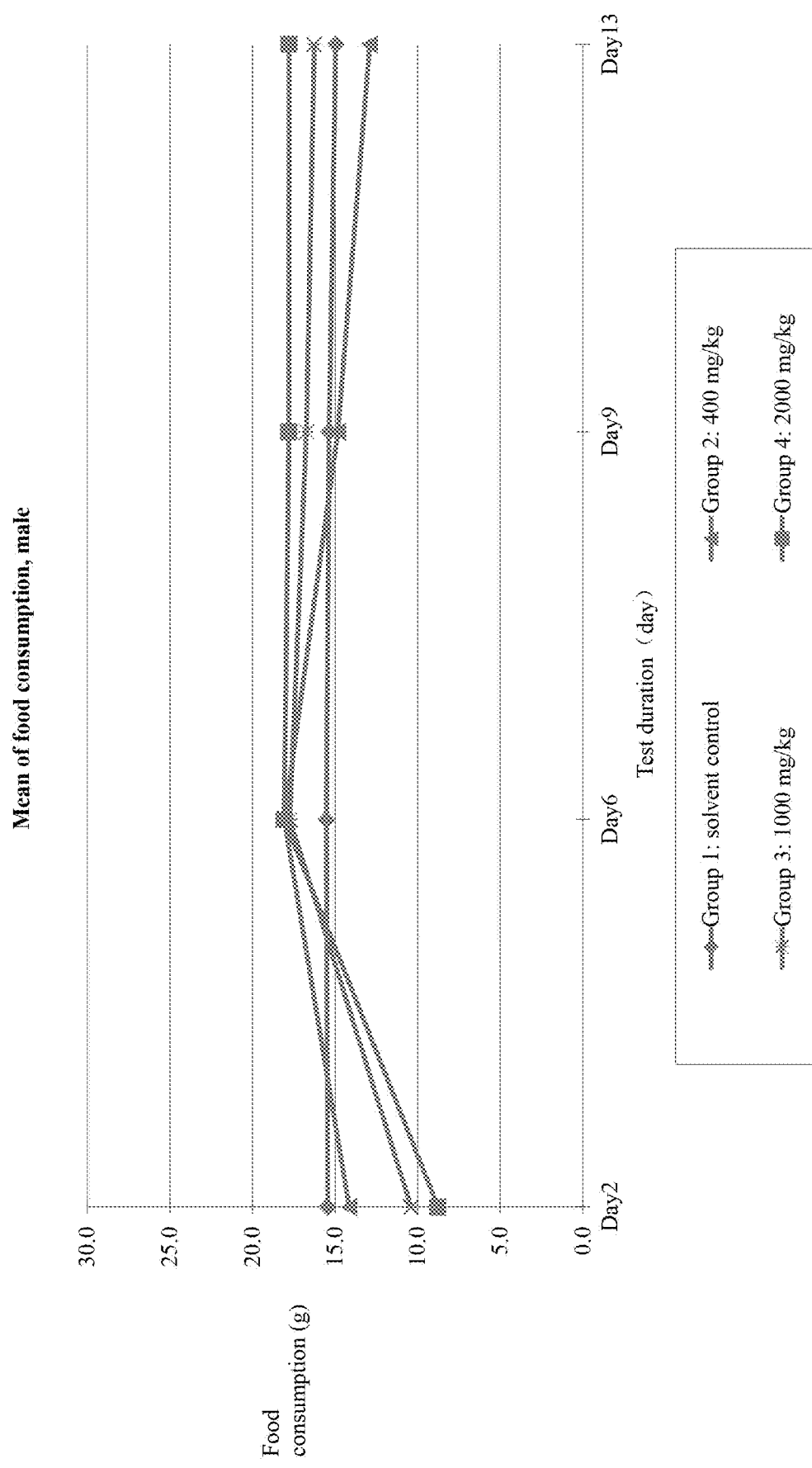
FIG. 13 is a change of food intake of female SD rats taking a test sample.

After treated by test samples, the DOHH2 cells were stimulated with anti-IgG, a relative expression level of p-Erk/t-Erk of the cells was analyzed by Western blotting, and results are shown in FIG. 9(A) and FIG. 9(B).

Experimental results show that, the relative levels of the p-Btk/t-Btk, p-PLCγ/t-PLCγ and p-Erk/t-Erk of the DOHH2 cells treated by the compound 6 and Ibrutinib are obviously decreased.

Biological Embodiment 5: hERG Current Blocking Test

1. Positive Control Drug: Amitriptyline Hydrochloride (Sigma-Aldrich, an International Standard hERG Channel Blocker)

2. Preparation of Solutions and Compounds

Extracellular fluid (mM): HEPES 10, NaCl 145, KCl 4, CaCl2 2, MgCl2 1, Glucose 10, the pH value was regulated to 7.4 with 1N sodium hydroxide; an osmotic pressure was regulated to 290-300 mOsm, filtration was performed, and the fluid was preserved at 4° C.;

pippette solution (in mM): HEPES 10, KOH 31.25, KCl 120, CaCl2 5.374, MgCl2 1.75, EGTA 10, Na2-ATP 4, the pH value was regulated to 7.2 with 1N sodium hydroxide; an osmotic pressure was regulated to 280-290 mOsm, filtration was performed, and the fluid was preserved at −20° C.;

compound preparation: the positive control drug amitriptyline hydrochloride, the compound 6 and Ibrutinib were dissolved into 100% of DMSO (Sigma-Aldrich, D2650) first and then prepared into a 30 mM of stock solution. Before the experiment, the above stock solution was diluted into a solution that is 1000 times that of each test concentration with the DMSO, and then diluted by 1000 times to reach the needed concentration with the extracellular fluid. The final concentration of the DMSO in the extracellular fluid was 0.1%.

Cell Strain

A stable cell strain CHO-hERG was purchased from Company AVIVA. In order to control quality, the minimum seal resistance was not less than 500M Ω, and hERG current was not less than 0.4 nA.

4. Electrophysiological Test hERG current was recorded by adopting a whole-cell patch clamp technique; cell suspension was added into a 35 mm of culture dish, and the culture dish was placed on an inverted microscope stage; perfusion of cells was performed with the extracellular fluid at flow velocity of 1-2 mL/min after cell adherence; a glass microelectrode was controlled in two steps by a pipette puller, wherein a water inlet resistance value is 2-5 M Ω; after whole-cell recording was established, a holding potential was −80 mV; depolarization was performed to reach +60 mV while applying voltage stimulation, and repolarization was performed to reach −50 mV so as to lead out hERG tail current; all records were performed after the current was stabilized; and extracellular perfusion dosing started from a low concentration, perfusion dosing lasted for 5-10 min at each concentration until the current was stabilized, and then perfusion dosing was performed at the next concentration.

5. Data Acquisition and Analysis

Stimulus release and signal acquisition were performed by virtue of Digidata 1440 (Molecular Devices) and pCLAMP software (10.2 version, Molecular Devices)A/D-D/A digital-to-analogue conversion; and signal amplification was performed by a patch clamp amplifier (Multiclamp 700B, Molecular Devices).

Further data analysis and curve fitting were performed by using Clampfit (10.2 version, Molecular Devices), EXCEL (2013 version, Microsoft) and GraphPad Prism. The data are represented by mean±standard deviation.

In data processing, when an hERG blocking effect was judged, a peak value of tail current and a baseline of the current were corrected; an inhibition ratio of the tail current represented the effect of each compound under different concentrations, and the numerical value IC50 was obtained by performing fitting on Hill equation as follows:

$$y = \left[\frac{\max - \min}{1 + \left(\frac{[\text{drug}]}{IC_{50}}\right)^{nH}}\right] + \min$$

y: $I/I_{control}$; max: 100%; min: 0%; [drug]: test concentration; nH: Hill slope; $IC_{50}$: maximum median inhibitory concentration of test matter.

6. Results

In the present test, the blocking effects of the compound 6 and the Ibrutinib on the hERG current are detected on the cell strain CHO-K1 capable of stably expressing the hERG channel by utilizing the whole-cell patch clamp technique.

The median inhibitory concentration (IC50) of the tested compound is obtained by best fitting of a Logistic equation. The blocking effect of the compound on the hERG is as shown in the following table. Amitriptyline is one of the hERG current blocking tool drugs with the most extensive applications, so it served as the positive control drug in the present study, and the results are as shown in the following table:

The numerical value IC50 of the compound recorded on the stable cell strain CHO-K1 on the hERG current

| Sample | IC50(uM) |
|---|---|
| Amitriptyline | 4.48 |
| Embodiment compound 6 | 8.06 |
| Ibrutinib | 0.97 |

Biological Embodiment 6: Single Dose Toxicity Test 20 healthy SD male rats and 20 healthy SD female rats were selected, and the rats were divided into 4 groups according to weight in a simple random manner based on an SPF level, wherein 10 rats existed in each group, including one half of female rats and one half of male rats; on day 1 of the experiment, animals (0 mg/kg) in the first group were subjected to dose delivery with blank solvents via oral gastric perfusion, and animals (400 mg/kg) in the second group, animals (1000 mg/kg) in the third group and animals (2000 mg/kg) in the fourth group were subjected to dose delivery with DD001y via oral gastric perfusion; and the animals were observed for 14 days.

During the experiment, all the animals were subjected to detailed clinical observation once (2 hours after drug administration) on the Day 1 and once every day on Day 2-14; the animals were weighed on the day of animal grouping, on the day of drug administration (before drug administration), Day 4, 7, 10 and 13 after drug administration and on the day of dissection, and weights were recorded; food consumption per cage was weighed within 24 hours on Day 2, 6, 9 and 13 in the experiment and recorded; and all live animals were subjected to gross anatomy examination on Day 15.

1. Preparation of Test and Control Products a solvent control group: 30 ml of solvents (0.5% MC (methylcellulose), 0.4% of cremophor EL and 0.1% of sodium lauryl sulfate) were sucked into a suitable container, the pH value was measured as 7, and a colorless clarified solution was obtained.

Compound 6 (400 mg/kg): 1507.1 mg of the compound 6 was weighed into a suitable container, solvents (0.5% MC (methylcellulose), 0.4% cremophor EL and 0.1% sodium lauryl sulfate) were added into the container to reach a constant volume of 30 ml, ultrasonic treatment was performed for 20 minutes, stirring was performed for 15 minutes, a mixing instrument was used for 5 minutes, the pH value was measured as 7, and white suspension was obtained.

Compound 6 (1000 mg/kg): 3765.5 mg of the compound 6 was weighed into a suitable container, solvents (0.5% MC (methylcellulose), 0.4% cremophor EL and 0.1% sodium lauryl sulfate) were added into the container to reach a constant volume of 30 ml, ultrasonic treatment was performed for 25 minutes, stirring was performed for 21 minutes, a mixing instrument was used for 5 minutes, the pH value was measured as 7, and white suspension was obtained.

Compound 6 (2000 mg/kg): 7530.5 mg of the compound 6 was weighed into a suitable container, solvents (0.5% MC (methylcellulose), 0.4% cremophor EL and 0.1% sodium lauryl sulfate) were added into the container to reach a constant volume of 30 ml, ultrasonic treatment was performed for 30 minutes, stirring was performed for 31 minutes, the pH value was measured as 7, and white suspension was obtained.

Experimental Design Table

| Group | Test sample | Administration dosage (mg/kg) | Administration concentration (mg/mL) | Administration volume (mL/kg) | Number of animals Male | Number of animals Female | Administration route and period |
|---|---|---|---|---|---|---|---|
| 1 | Solvent control group | 0 | 0 | 10 | 5 | 5 | POa, once |
| 2 | Compound 6 | 400 | 40 | 10 | 5 | 5 | POa, once |
| 3 | Compound 6 | 1000 | 100 | 10 | 5 | 5 | POa, once |
| 4 | Compound 6 | 2000 | 200 | 10 | 5 | 5 | POa. once |

The animals were subjected to fasting within 10-16 h before intragastric oral administration, and feeding was restored within 2 h after administration.

3. Results

Specific situations and performances of test objects are shown in FIGS. 10-13.

No animal died in the test process. Weights of all animals surviving until the experiment is ended were gradually increased in the test process. Compared with the solvent control group, no abnormality was shown. Individual animals in the group 400 mg/kg and the group 1000 mg/kg had red dry secretions (perirhinal), individual animals in the group 2000 mg/kg had red dry secretions (perirhinal), red wet secretions (perirhinal) and red dry secretions (a periorbital zone of the left eye), and the above abnormality may be related to administration of test samples. The food consumption of the animals in the group 1000 mg/kg and the group 2000 mg/kg on the Day 2 after administration was lower than that of the solvent control group, and returned to normal on Day 6. Each animal had no abnormality during gross anatomy.

Under the present test conditions, after the SD rats were orally administered with the compound 6 once, the maximum tolerance dosage was 2000 mg/kg.

| | Species | Administration route | Dosage (mg/kg) | Maximum tolerance dosage (mg/kg) | Results |
|---|---|---|---|---|---|
| Compound 6 | Rats | Oral | 0, 400, 1000, 2000 | 2000 | No animal died; all tissues of each animals are normal during anatomy. |
| Ibrutinib (FDA) | Rats | Oral | 0, 400, 1000, 2000 | 400 | Weights of 400 mg/kg rats are decreased, and some 1000 mg/kg rats died |
| | Mice | Oral | 0, 500, 1000, 2000 | 2000 | The 2000 mg/kg mice have decreased activities, decreased body temperatures and respiratory failure |

Ibrutinib data comes from FDA Database. http://www.accessdata.fda.gov/drugsatfda_docs/nda/2013/205552Orig1s000ClinPharmR.pdf (accessed June 2015)

Biological Embodiment 7: Pharmacokinetic Study of Performing Respective Single Intravenous and Oral Dose Delivery with Test Samples on SD Rats and Beagle Dogs 6 male SD rats were selected, and grouped and administered according to an experimental design table; 3 animals in the first group were intravenously administered once on the day of administration, wherein the administration dosage was 2 mg/kg, and the administration volume was 5 mL/kg; 3 animals in the second group were orally intragastrically administered once on the day of administration, wherein the administration dosage was 10 mg/kg, and the administration volume was 10 mL/kg.

All the animals were subjected to cage edge observation twice every day so as to determine whether the animals got ill or had injuries or death and other situations and whether supply of foods and water was sufficient. In the test process, all administered animals were subjected to detailed clinical observation before administration and at blood collection points.

Before administration (0 h) and within 0.083 h, 0.25 h, 0.5 h, 1 h, 2 h, 4 h, 6 h, 8 h and 24 h after administration, blood samples were collected from femoral veins at 10 time points so as to be used for blood concentration test.

6 male beagle dogs were selected, grouped and administered according to an experimental design table; 3 animals in the first group were intravenously administered once on the day of administration, wherein the administration dosage was 2 mg/kg, and the administration volume was 2.5 mL/kg; 3 animals in the second group were orally intragastrically administered once on the day of administration, wherein the administration dosage was 30 mg/kg, and the administration volume was 5 mL/kg.

All the animals were subjected to cage edge observation twice every day so as to determine whether the animals got ill or had injuries or death and other situations and whether supply of foods and water was sufficient. In the test process, all administered animals were subjected to detailed clinical observation before administration and at blood collection points.

Before administration (0 h) and within 0.083 h, 0.25 h, 0.5 h, 1 h, 2 h, 4 h, 6 h, 8 h and 24 h after administration, blood samples were collected from femoral veins at 10 time points so as to be used for blood concentration test. Experimental design table

| Number of animals | | | Drug administration | | | | | |
|---|---|---|---|---|---|---|---|---|
| Group | Male | Test sample | Dosage of test sample (mg/kg) | Concentration of test sample (mg/mL) | Administration volume (mL/kg) | Administration manner | Times of administration | Collected sample |
| 1 | 3 | Compound 6 | 2 | 0.4 | 5 | IV | 1 | Plasma |
| 2 | 3 | Compound 6 | 10 | 1 | 10 | PO* | 1 | Plasma |

*Before oral administration, all the animals are subjected to fasting to stay overnight (10-14 hours) and then fed within 2 hours after administration.

| Number of animals | | | Drug administration | | | | | |
|---|---|---|---|---|---|---|---|---|
| Group | Male | Test sample | Dosage of test sample (mg/kg) | Concentration of test sample (mg/mL) | Administration volume (mL/kg) | Administration manner | Times of administration | Collected sample |
| 1 | 3 | Compound 6 | 2 | 0.8 | 2.5 | IV | 1 | Plasma |
| 2 | 3 | Compound 6 | 30 | 6 | 5 | PO* | 1 | Plasma |

*Before oral administration, all the animals are subjected to fasting to stay overnight (10-18 hours) and then fed within 2 hours after administration.

Results

Partial pharmacokinetic parameters of the SD rats administrated with the compound 6 were shown in the following table. After the SD rats were administered with 2 mg/kg of the compound 6 via intravenous injection, $C_{max}$ was 658.49 ng/mL, and $AUC_{(0-t)}$ was 270.52 h*ng/mL; and after the SD rats were administered with 10 mg/kg of the compound 6 via oral intragastric administration, the $C_{max}$ was 447.09 ng/mL, and $AUC_{(0-t)}$ was 449.18 h*ng/mL.

Partial pharmacokinetic parameters of the beagle dogs administered with the compound 6 were shown in the following table. After the beagle dogs were administered with 2 mg/kg of the compound 6 via intravenous injection, $C_{max}$ was 1225.90 ng/mL, and $AUC_{(0-t)}$ was 888.22 h*ng/mL; and after the beagle dogs were administered with 30 mg/kg of the compound 6 via oral intragastric administration, the $C_{max}$ was 3828.63 ng/mL, and $AUC_{(0-t)}$ was 7419.16 h*ng/mL.

|  | Administration route | Dosage (mg/kg) | $T^{1/2}$ (h) | $T_{max}$ (h) | $C_{max}$ (ng/ml) | AUC (h*ng/ml) |
|---|---|---|---|---|---|---|
| Rat | IV | 2 | 0.18 | 0.083 | 658.49 | 270.52 |
|  | PO | 10 | 1.89 | 0.42 | 447.09 | 449.18 |
| Dog | IV | 2 | 0.8 | 0.083 | 1225.90 | 888.22 |
|  | PO | 30 | 0.75 | 0.83 | 3828.63 | 7419.16 |

|  |  | Compound 6 | Ibrutinib (FDA) |
|---|---|---|---|
| Bioavailability | Rat | 32.17% | 18%-23% |
|  | Dog | 54.64% | 7%-11% |
|  | People | / | 2.9% |

Ibrutinib data comes from FDA Database. http://www.accessdata.fda.gov/drugsatfda_docs/nda/2013/205552Orig1s000ClinPharmR.pdf (accessed June 2015).

Biological Embodiment 8: Study on Effects of Active Compounds for Inhibiting In Vitro Tumor Cell Proliferation 1. Cell Line and Culture Method

| Cell line | Tumor type | Growth characteristic | Culture method |
|---|---|---|---|
| TMD8 | Large B cell lymphoma | Suspension | RPMI-1640 + FBS10% |
| OCI-LY10 | Lymphoma | Suspension | RPMI-1640 + FBS10% |
| OCI-LY3 | Lymphoma | Suspension | DMEM(low glucose) + 10% FBS |
| WSU-NHL | B cell lymphoma | Suspension | RPMI-1640 + 10% HI-FBS |
| DOHH-2 | Lymphoma | Suspension | RPMI 1640 + 10% FBS |
| Mino | Leukemia | Suspension | RPMI-1640 + 15% FBS |
| SU-DHL-6 | Leukemia | Suspension | RPMI-1640 + 10% FBS |
| WSU-DLCL-2 | Leukemia | Suspension | RPMI-1640 + 10% HI-FBS |
| Ramos | Leukemia | Suspension | RPMI-1640 + 10% FBS + 2 mM L-glutamine |
| Raji | Leukemia | Suspension | RPMI-1640 + 10% FBS + 2 mM L-glutamine |
| Granta-519 | Leukemia | Suspension | DMEM+10% H.I. FBS + 2 mM L-glutamine |
| SU-DHL-10 | Leukemia | Suspension | RPMI-1640 + 10% FBS |
| SU-DHL-4 | Leukemia | Suspension | RPMI-1640 + 10% FBS |
| OCI-LY19 | Leukemia | Suspension | RPMI-1640 + 10% FBS |
| DB | Lymphoma | Suspension | RPMI-1640 + 10% FBS |

2. Culture Medium

Table. Culture Medium and Reagent

| Culture medium and reagent | Manufacturer | Item No. |
|---|---|---|
| RPMI 1640 | GIBCO | 22400-089 |
| DMEM | GIBCO | 11995-065 |
| Dulbecco's PBS | Thermo | SH30028.02B |
| FBS | Hyclone | SH30084.03 |
| Antibiotic-antimycotic | GIBCO | 15240-062 |
| DMSO | SIGMA | D2650 |
| L-glutamine | Invitrogen | 25030164 |

3. Reagents and Instruments Used by Cell Activity Experiments

Promega CellTiter-Glo cell activity detection kit by luminescence (Promega-G7573).

2104 EnVision plate reader, PerkinElmer.

4. Experimental Methods and Steps 4.1 Cell Culture

Tumor cell lines were cultured in a 5% of $CO_2$ incubator at 37° C. according to respective culture conditions; and periodic passage was performed, and cells positioned in a logarithmic phase were taken for planking.

4.1.1 Cell Planking 1) cell staining was performed with trypan blue and living cells were counted;

2) the cell concentration was adjusted to an appropriate concentration;

3) 90 μL of cell suspension was added into each well of the culture plate, and a culture solution containing no cell was added into blank control;

4) the culture plate was cultured overnight in the 5% of $CO_2$ incubator having relative humidity of 100% at 37° C.

4.2 Preparation of Compound Storage Plate

Preparation of a 400× compound storage plate: the compound was diluted from the maximum concentration gradient to the lowest concentration with DMSO.

4.3 Preparation of 10× Compound Working Solution and Compound Treated Cells

1) Preparation of 10× compound working solution: 76 μL of a cell culture solution was added into a 96-well plate having a V-shaped bottom, 4 μL of a compound was sucked from the 400× compound storage plate to be added into the cell culture solution of the 96-well plate, 4 μL of DMSO was added into solvent control and blank control; and the added compound or DMSO was blown by a gun and uniformly mixed.

2) Administration: 10 μL of the 10× compound working solution was added into the cell culture plate according to Table 1, and 10 μL of a DMSO-cell culture solution mixed solution was added into the solvent control and the blank control, wherein the final concentration of the DMSO was 0.50%.

3) The 96-well cell plate was cultured in the incubator for 72 h.

4.4 CellTiter-Glo Cell Activity Detection by Luminescence

The following steps were performed according to the specification of the Promega CellTiter-Glo cell activity detection kit by luminescence (Promega-G7573).

1) a CellTiter-Glo buffer solution was molten and placed at room temperature;

2) a CellTiter-Glo substrate was placed at room temperature;

3) the CellTiter-Glo buffer solution was added into a bottle of the CellTiter-Glo substrate so as to dissolve the substrate, thereby preparing a CellTiter-Glo working solution;

4) slow vortex shaking was performed until the substrate was fully dissolved;

5) the cell culture plate was taken out and stilled for 30 minutes so as to balance to the room temperature;

6) 50 μL (equal to one half of volume of the cell culture solution in each well) of the CellTiter-Glo working solution was added into each well, and the cell plate was coated by aluminum-foil paper for shading;

7) the culture plate was shaken on an orbital shaker for 2 minutes so as to induce cell lysis;

8) the culture plate was placed at the room temperature for 10 minutes so as to stabilize a luminescence signal; and 9) the luminescence signal was detected on the 2104 EnVision plate reader.

5. Data analysis

The inhibition rate (IR) of the compound was detected by using the following formula: IR (%)=(1−(RLU compound−RLU blank control)/(RLU solvent control−RLU blank control))*100%.

Inhibition Effect of Compound 6 on In Vitro Tumor Cell Proliferation

| B-Lymphoma Cell Line | Growth $IC_{50}(nM)$ |
|---|---|
| TMD8 | 0.85 |
| DOHH-2 | <3 |
| OCI-LY10 | 6 |
| SU-DHL-4 | 75 |
| WSU-DLCL-2 | 921 |
| WSU-NHL | 1019 |
| Ramos | 1398 |
| Mino | 2174 |
| OCI-LY19 | 6788 |
| Granta-519 | 7065 |
| SU-DHL-10 | >10000 |
| DB | >10000 |
| Raji | >10000 |
| OCI-LY3 | >10000 |
| Jeko-1 | >10000 |
| SU-DHL-6 | >10000 |

We claim:

1. A compound of following general formula D, optical isomers or mixtures of the compounds, salts, or solvates, thereof:

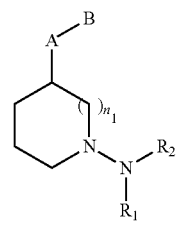

wherein, A comprises the structure of formula D-1:

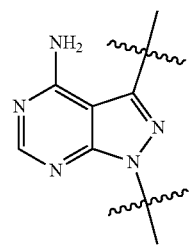

B comprises the structure of formula L-1:

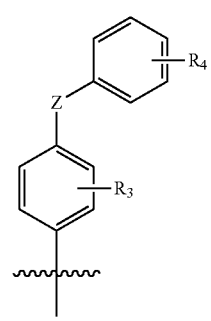

wherein, $R_1$ represents H;

$R_2$ represents $R_6CO$;

$R_3$ represents H;

$R_4$ represents H;

$R_6$ is alkenyl;

Z is O;

$n_1$ represents 0 or 1.

2. A drug composition, comprising the compound with the general formula D and optical isomers or mixtures of the compounds, salts, or solvates, thereof according to claim 1.

3. A Btk inhibitor drug comprising the compound with the general formula D, and the optical isomers or mixtures of the compounds, salts, or solvates, thereof according to claim 1.

4. A method for reducing Btk activities in a subject, comprising:
  administering to the subject an effective amount of the compound with the general formula D, and the optical isomers or mixtures of the compounds, salts, or solvates-thereof according to claim 1.

5. A B cell activation inhibitor comprising the drug composition of claim 2.

* * * * *